US012721858B2

(12) United States Patent
Park et al.

(10) Patent No.: US 12,721,858 B2
(45) Date of Patent: Sep. 1, 2026

(54) DOUBLE-STRANDED OLIGONUCLEOTIDE TARGETING DKK1 GENE, CONSTRUCT INCLUDING SAME, AND HAIR LOSS PREVENTION OR HAIR GROWTH COMPOSITION CONTAINING SAME

(71) Applicant: BIONEER CORPORATION, Daejeon (KR)

(72) Inventors: Han-Oh Park, Sejong-si (KR); Sung Il Yun, Daejeon (KR); Sang-Jin Byun, Daejeon (KR); Pyoung Oh Yoon, Sejong-si (KR); Sang-Kyu Lee, Daejeon (KR); Tae-Rim Kim, Daejeon (KR); Young-Ho Ko, Daejeon (KR); Seung-Seob Son, Chungcheongnam-do (KR); Eun-Ah Goh, Daejeon (KR); Hyung-Jin Kim, Gyeonggi-do (KR)

(73) Assignee: BIONEER CORPORATION, Daejeon (KR)

( * ) Notice: Subject to any disclaimer, the term of this patent is extended or adjusted under 35 U.S.C. 154(b) by 228 days.

(21) Appl. No.: 17/423,372

(22) PCT Filed: Jan. 15, 2020

(86) PCT No.: PCT/KR2020/000750

§ 371 (c)(1),
(2) Date: Jul. 15, 2021

(87) PCT Pub. No.: WO2020/149644

PCT Pub. Date: Jul. 23, 2020

(65) Prior Publication Data

US 2022/0088051 A1 Mar. 24, 2022

(30) Foreign Application Priority Data

Jan. 15, 2019 (KR) ........................ 10-2019-0005277

(51) Int. Cl.
*A61K 31/713* (2006.01)
*A61P 17/14* (2006.01)

(52) U.S. Cl.
CPC ............ *A61K 31/713* (2013.01); *A61P 17/14* (2018.01)

(58) Field of Classification Search
CPC .............................. A61K 31/713; A61P 17/14
See application file for complete search history.

(56) References Cited

U.S. PATENT DOCUMENTS

| | | | |
|---|---|---|---|
| 5,660,985 A | 8/1997 | Pieken | |
| 5,808,023 A | 9/1998 | Sanghvi et al. | |
| 5,958,691 A | 9/1999 | Pieken et al. | |
| 6,175,001 B1 | 1/2001 | Barbas et al. | |
| 6,326,358 B1 | 12/2001 | Manoharan | |
| 6,531,584 B1 | 3/2003 | Cook et al. | |
| 2008/0293053 A1* | 11/2008 | Keller | C12N 15/1135 435/375 |
| 2013/0331342 A1 | 12/2013 | Youngquist et al. | |
| 2016/0122764 A1* | 5/2016 | Chae | A61P 11/06 536/24.5 |

FOREIGN PATENT DOCUMENTS

| | | | |
|---|---|---|---|
| CN | 101643731 | A | 10/2010 |
| JP | 2006217844 | A | 8/2006 |
| JP | 2009517080 | A | 4/2009 |
| KR | 100883471 | B1 | 2/2009 |
| KR | 1020100051195 | A | 5/2010 |
| KR | 1020110062918 | A | 6/2011 |
| KR | 101167675 | B1 | 7/2012 |
| KR | 101224828 | B1 | 1/2013 |
| KR | 1020130057023 | A | 5/2013 |
| KR | 1020150115687 | A | 10/2015 |
| KR | 1020160033125 | A | 3/2016 |
| KR | 1020180123989 | A | 11/2018 |
| WO | 2004045543 | A2 | 6/2004 |
| WO | 2007084344 | A2 | 7/2007 |
| WO | 2009102427 | A2 | 8/2009 |

(Continued)

OTHER PUBLICATIONS

Ui-Tei, Kumiko, et al. "Functional dissection of siRNA sequence by systematic DNA substitution: modified siRNA with a DNA seed arm is a powerful tool for mammalian gene silencing with significantly reduced off-target effect." Nucleic acids research 36.7 (2008):2136-2151. (Year: 2008).*

Akhtar, S., et al., "Nonviral delivery of synthetic siRNAs in vivo", The Journal of Clinical Investigation, Dec. 2007, pp. 3623-3632, vol. 117, No. 12, Publisher: http://www.jci.org.

Amarzguioui, M., et al., "Tolerance for mutations and chemical modifications in a siRNA", Nucleic Acide Research, 2003, pp. 589-595, vol. 31, No. 2, Publisher: Oxford University Press.

Barik, S., "Silence of the transcripts: RNA interference in medicine", J Mol Med, 2005, pp. 764-773, vol. 83, Publisher: Springer-Verlag 2005.

Behlke, M., "Progress Towards in Vivo Use of siRNAs", Molecular Therapy, Apr. 2006, pp. 644-670, vol. 13, No. 4, Publisher: The American Society of Gene Therapy.

(Continued)

*Primary Examiner* — Jennifer Dunston
*Assistant Examiner* — Christina Tran
(74) *Attorney, Agent, or Firm* — HULTQUIST, PLLC; Steven J. Hultquist

(57) ABSTRACT

A double-stranded oligonucleotide construct is described in which a hydrophilic substance and a hydrophobic substance are conjugated by a simple covalent bond or a linker-mediated covalent bond at both ends of a DKK1-specific double-stranded oligonucleotide for delivery of the double-stranded oligonucleotide into cells, as well as a nanoparticle produced by self-assembly of the double-stranded oligonucleotide construct via hydrophobic interaction in an aqueous solution, and a hair-loss-preventing and hair-growth-promoting composition containing the double-stranded oligonucleotide construct or nanoparticle, and effective to suppress the expression of DKK1 without side effects.

20 Claims, 6 Drawing Sheets

Specification includes a Sequence Listing.

(56) References Cited

FOREIGN PATENT DOCUMENTS

| | | | |
|---|---|---|---|
| WO | 2012135230 | A2 | 10/2012 |
| WO | 2015002511 | A1 | 1/2015 |

OTHER PUBLICATIONS

Bertrand, J-R, et al., "Comparison of antisense oligonucleotides and siRNAs in cell culture and in vivo", Biochemical and Biophysical Communications, 2002, pp. 1000-1004, vol. 296.

Braasch, D.A., et al., "Biodistribution of phosphodiester and phosphorothioate siRNA", Bioorganic & Medicinal Chemistry Letters, 2004, pp. 1139-1143, vol. 14, Publisher: Elsevier.

Bramsen, J.B., et al., "A screen of chemical modifications identifies position-specific modification by UNA to most potently reduce siRNA off-target effects", Nucleic Acids Research, 2010, pp. 5761-5773, vol. 38, No. 17, Publisher: Oxford University Press.

Caricasole, A., et al., "Induction of Dickkopf-1, a Negative Modulator of the Wnt Pathway, Is Associated with Neuronal Degeneration in Alzheimer's Brain", The Journal of Neuroscience, Jun. 30, 2004, pp. 6021-6027, vol. 24, No. 26.

Chiu, Y.-L., et al., "siRNA Function in RNAi: A chemical modification analysis", RNA, 2003, pp. 1034-1048, vol. 9, Publisher: Cold Spring Harbor Laboratory Press.

Crooke, S., "Progress in Antisense Technology", Annu. Rev. Med., 2004, pp. 61-95, vol. 55, Publisher: Annual Reviews.

Dallob, A.L., et al., "The Effect of Finasteride, a 5-Reductase Inhibitor, on Scalp Skin Testerone and Dihydrotestosterone Concentrations in Patients with Male Pattern Baldness", Journal of Clinical Endocrinology and Metabolism, 1994, pp. 703-709, vol. 79, No. 3, Publisher: The Endocrine Society.

Ellsworth, K., et al., "Expression of the Type 1 And 2 Steroid 5-Reductases in Human Fetal Tissues", Biochemical and Biophysical Communications, Oct. 13, 1995, pp. 774-780, vol. 215, No. 2, Publisher: Academic Press, Inc.

Kaufman, K.D., "Androgens and alopecia", Molecular and Cellular Endocrinology, 2002, pp. 89-95, vol. 198, Publisher: Elsevier.

Kwack, M.H., et al., "Dickkopf 1 Promotes Regression of Hair Follicles", Journal of Investigative Dermatology, 2012, pp. 1554-1560, vol. 132, Publisher: Society for Investigative Dermatology.

Mao, B., et al., "LDL—receptor-related protein 6 is a receptor for Dickkopf proteins", Nature, May 17, 2001, pp. 321-325, vol. 411, Publisher: Macmillan Magazines Limited.

Mcdonagh, A. J. G., et al., "The Pathogenesis of Alopecia Areata", Dermatologic Clinics, Oct. 1996, pp. 661-670, vol. 14, No. 4.

Naito, A., et al., "Dihydrotestosterone inhibits murine hair growth via the androgen receptor", British Journal of Dermatology, 2008, pp. 300-305, vol. 159, Publisher: 2008 British Association of Dermatologists.

Niida, A., et al., "DKK1, a negative regulator of Wnt signalling, is a target of the—catenin/TCF pathway", Oncogene, 2004, pp. 8520-8526, vol. 23, Publisher: Nature Publishing Group.

Opalinska, J., et al., "Nucleic-Acid Therapeutics: Basic Principles and Recent Applications", Nature Reviews Drug Discovery, 2002, pp. 503-514, vol. 1.

Passchier, J., "Quality of Life Issues in Male Pattern Hair Loss", Dermatology, 1998, pp. 217-218, vol. 197, Publisher: Karger.

Shigeta, K., et al., "Novel histidine-conjugated galactosylated cationic liposomes for efficient hepatocyte-selective gene transfer in human hepatoma HepG2 cells", Journal of Controlled Release, 2007, pp. 262-270, vol. 118, Publisher: Elsevier.

Vaish, N., et al., "Improved specificity of gene silencing by siRNAs containining unlocked nucleobase analogs", Nucleic Acids Research, 2011, pp. 1823-1832, vol. 39, No. 5, Publisher: Oxford University Press.

Veronese, F., "Peptide and protein PEGylation: a review of problems and solutions", Biomaterials, 2001, pp. 405-417, vol. 22, Publisher: Elsevier.

Veronese, F.M., et al., "PEGylation, successful aproach to drug delivery", Drug Discovery Today, Dec. 2005, pp. 1451-1458, vol. 10, No. 21, Publisher: Elsevier.

Xie, F., et al., "Harnessing in vivo siRNA delivery for drug discovery and therapeutic development", Drug Discovery Today, 2006, pp. 67-73, vol. 11, No. 1/2, Publisher: Elsevier.

Yamaguchi, Y., et al., "Mesenchymal-epithelial interactions in the skin: increased expression of dickkopf1 by palmoplanter fibroblasts inhibits melanocyte growth and differentiation", Journal of Cell Biology, Apr. 26, 2004, pp. 275-285, vol. 165, No. 2.

Zelphati, O., et al., "Mechanism of oligonucleotide release from cationic liposomes", Biochemistry, Oct. 1996, pp. 11493-11498, vol. 93, Publisher: Proc. Natl. Acad. Sci. USA.

Search Report Issued in Chinese Patent Application No. 202080014857.2, Feb. 1, 2023.

EESR Issued in European Patent Application No. 20742087.8 on Aug. 25, 2023.

Lim, Y.Y., et al., "Potential relationship between the canonical Wnt signalling pathway and expression of the Vitamin D receptor in alopecia", Clinical and Experimental Dermatology, 2014, pp. 368-375, vol. 39, Publisher: British Association of Dermatologists.

Zhang, Y., et al., "Homologous recombination was used to construct DKK1, BMP4 Eukaryotic expression vectors and co-transfection of fibroblasts for expression studies", DeepL Pro, 2018, doi: 10. 7668 /hbnxb. 2018. 05. 017, Publisher: www.deepL.com/pro.

Zhong, S., "wbt/beta-catenin", China Academic Journal, 2021, English translation of Abstract; http/www.cnki.net, Publisher: Electronic Publishing House.

Office Action issued in counterpart Japanese Patent Application No. 2021-541051 on Feb. 17, 2023.

English Translation of Office Action issued in counterpart Japanese Patent Application No. 2021-541051 on Feb. 17, 2023.

* cited by examiner

FIG. 1

```
          90        100       110       120       130       140       150       160       170       180
GTGGCGGTGGCGGCGCAGAGCTCTGTGCTCCCTGCAGTCAGGACTCTGGGACCGCAGGGGGCTCCCGGACCCTGACTCTGCAGCCGAACCGGCACGGTTTC
                                     TCAGGACTCTGGGACCGCA
                                      CAGGACTCTGGGACCGCAG
                                       AGGACTCTGGGACCGCAGG
                                        GGACTCTGGGACCGCAGGG
                                         GACTCTGGGACCGCAGGGG
                                          ACTCTGGGACCGCAGGGGG
                                           CTCTGGGACCGCAGGGGGC
                                            TCTGGGACCGCAGGGGGCT
                                             CTGGGACCGCAGGGGGCTC
                                              TGGGACCGCAGGGGGCTCC
                                               GGGACCGCAGGGGGCTCCC
```

FIG. 6
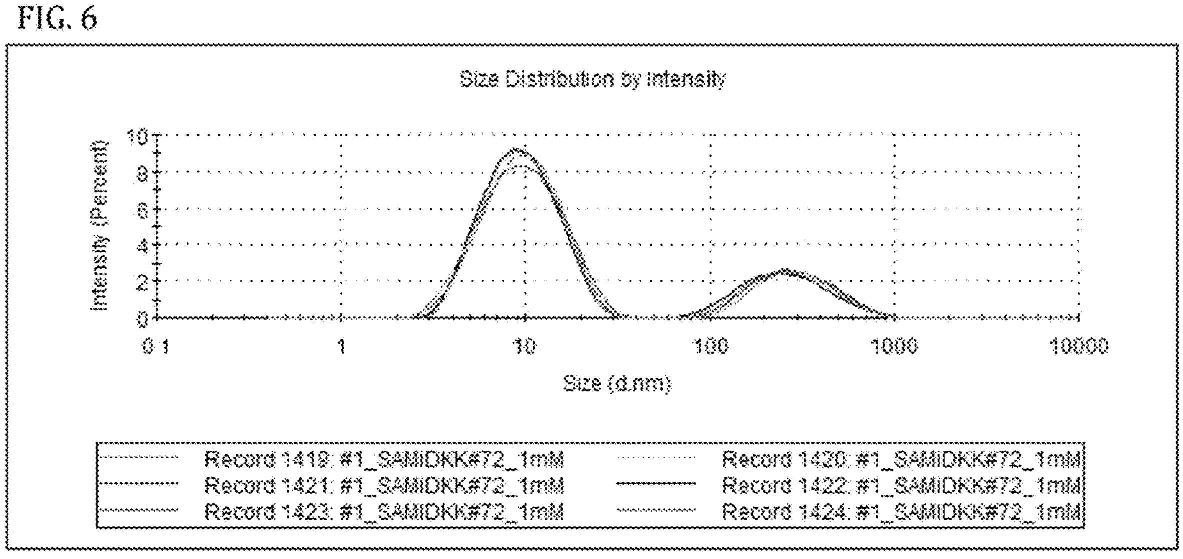
FIG. 7
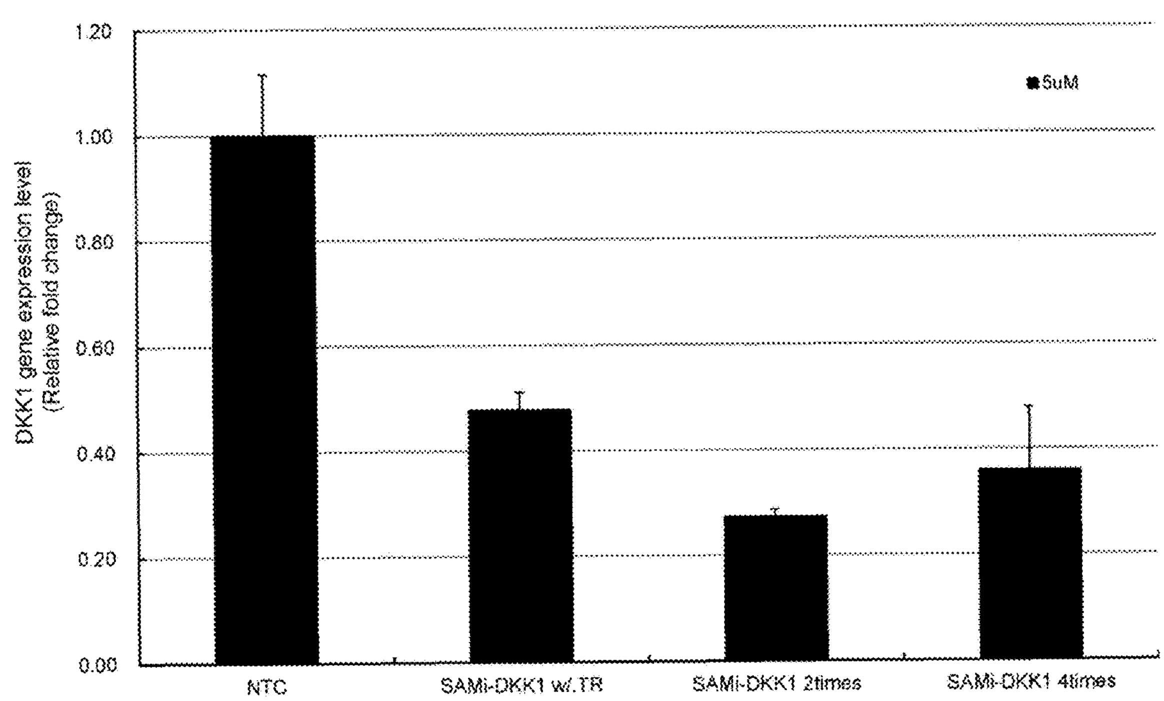

```
                         SEQUENCE LISTING

<160> NUMBER OF SEQ ID NOS: 325

<210> SEQ ID NO 1
<211> LENGTH: 19
<212> TYPE: DNA
<213> ORGANISM: Artificial Sequence
<220> FEATURE:
<223> OTHER INFORMATION: SAMi-hDKK1#001

<400> SEQUENCE: 1

tcaggactct gggaccgca                                                   19


<210> SEQ ID NO 2
<211> LENGTH: 19
<212> TYPE: DNA
<213> ORGANISM: Artificial Sequence
<220> FEATURE:
<223> OTHER INFORMATION: SAMi-hDKK1#002

<400> SEQUENCE: 2

caggactctg ggaccgcag                                                   19


<210> SEQ ID NO 3
<211> LENGTH: 19
<212> TYPE: DNA
<213> ORGANISM: Artificial Sequence
<220> FEATURE:
<223> OTHER INFORMATION: SAMi-hDKK1#003

<400> SEQUENCE: 3

aggactctgg gaccgcagg                                                   19


<210> SEQ ID NO 4
<211> LENGTH: 19
<212> TYPE: DNA
<213> ORGANISM: Artificial Sequence
<220> FEATURE:
<223> OTHER INFORMATION: SAMi-hDKK1#004

<400> SEQUENCE: 4

ggactctggg accgcaggg                                                   19
```

<210> SEQ ID NO 5
<211> LENGTH: 19
<212> TYPE: DNA
<213> ORGANISM: Artificial Sequence
<220> FEATURE:
<223> OTHER INFORMATION: SAMi-hDKK1#005

<400> SEQUENCE: 5
ctgcagccga accggcacg 19

<210> SEQ ID NO 6
<211> LENGTH: 19
<212> TYPE: DNA
<213> ORGANISM: Artificial Sequence
<220> FEATURE:
<223> OTHER INFORMATION: SAMi-hDKK1#006

<400> SEQUENCE: 6
tgcagccgaa ccggcacgg 19

<210> SEQ ID NO 7
<211> LENGTH: 19
<212> TYPE: DNA
<213> ORGANISM: Artificial Sequence
<220> FEATURE:
<223> OTHER INFORMATION: SAMi-hDKK1#007

<400> SEQUENCE: 7
gcagccgaac cggcacggt 19

<210> SEQ ID NO 8
<211> LENGTH: 19
<212> TYPE: DNA
<213> ORGANISM: Artificial Sequence
<220> FEATURE:
<223> OTHER INFORMATION: SAMi-hDKK1#008

<400> SEQUENCE: 8
cagccgaacc ggcacggtt 19

<210> SEQ ID NO 9
<211> LENGTH: 19
<212> TYPE: DNA
<213> ORGANISM: Artificial Sequence
<220> FEATURE:
<223> OTHER INFORMATION: SAMi-hDKK1#009

<400> SEQUENCE: 9
agccgaaccg gcacggttt 19

<210> SEQ ID NO 10
<211> LENGTH: 19
<212> TYPE: DNA
<213> ORGANISM: Artificial Sequence
<220> FEATURE:
<223> OTHER INFORMATION: SAMi-hDKK1#010

<400> SEQUENCE: 10
gccgaaccgg cacggtttc 19

<210> SEQ ID NO 11
<211> LENGTH: 19
<212> TYPE: DNA
<213> ORGANISM: Artificial Sequence
<220> FEATURE:

-continued

<223> OTHER INFORMATION: SAMi-hDKK1#011

<400> SEQUENCE: 11
ccgaaccggc acggtttcg 19

<210> SEQ ID NO 12
<211> LENGTH: 19
<212> TYPE: DNA
<213> ORGANISM: Artificial Sequence
<220> FEATURE:
<223> OTHER INFORMATION: SAMi-hDKK1#012

<400> SEQUENCE: 12
cgaaccggca cggtttcgt 19

<210> SEQ ID NO 13
<211> LENGTH: 19
<212> TYPE: DNA
<213> ORGANISM: Artificial Sequence
<220> FEATURE:
<223> OTHER INFORMATION: SAMi-hDKK1#013

<400> SEQUENCE: 13
gaaccggcac ggtttcgtg 19

<210> SEQ ID NO 14
<211> LENGTH: 19
<212> TYPE: DNA
<213> ORGANISM: Artificial Sequence
<220> FEATURE:
<223> OTHER INFORMATION: SAMi-hDKK1#014

<400> SEQUENCE: 14
aaccggcacg gtttcgtgg 19

<210> SEQ ID NO 15
<211> LENGTH: 19
<212> TYPE: DNA
<213> ORGANISM: Artificial Sequence
<220> FEATURE:
<223> OTHER INFORMATION: SAMi-hDKK1#015

<400> SEQUENCE: 15
accggcacgg tttcgtggg 19

<210> SEQ ID NO 16
<211> LENGTH: 19
<212> TYPE: DNA
<213> ORGANISM: Artificial Sequence
<220> FEATURE:
<223> OTHER INFORMATION: SAMi-hDKK1#016

<400> SEQUENCE: 16
ccggcacggt ttcgtgggg 19

<210> SEQ ID NO 17
<211> LENGTH: 19
<212> TYPE: DNA
<213> ORGANISM: Artificial Sequence
<220> FEATURE:
<223> OTHER INFORMATION: SAMi-hDKK1#017

<400> SEQUENCE: 17
cggcacggtt tcgtgggga 19

<210> SEQ ID NO 18
<211> LENGTH: 19
<212> TYPE: DNA
<213> ORGANISM: Artificial Sequence
<220> FEATURE:
<223> OTHER INFORMATION: SAMi-hDKK1#018

<400> SEQUENCE: 18
ggcacggttt cgtggggac 19

<210> SEQ ID NO 19
<211> LENGTH: 19
<212> TYPE: DNA
<213> ORGANISM: Artificial Sequence
<220> FEATURE:
<223> OTHER INFORMATION: SAMi-hDKK1#019

<400> SEQUENCE: 19
aggcttgcaa agtgacggt 19

<210> SEQ ID NO 20
<211> LENGTH: 19
<212> TYPE: DNA
<213> ORGANISM: Artificial Sequence
<220> FEATURE:
<223> OTHER INFORMATION: SAMi-hDKK1#020

<400> SEQUENCE: 20
ggcttgcaaa gtgacggtc 19

<210> SEQ ID NO 21
<211> LENGTH: 19
<212> TYPE: DNA
<213> ORGANISM: Artificial Sequence
<220> FEATURE:
<223> OTHER INFORMATION: SAMi-hDKK1#021

<400> SEQUENCE: 21
gcttgcaaag tgacggtca 19

<210> SEQ ID NO 22
<211> LENGTH: 19
<212> TYPE: DNA
<213> ORGANISM: Artificial Sequence
<220> FEATURE:
<223> OTHER INFORMATION: SAMi-hDKK1#022

<400> SEQUENCE: 22
gcgcagcggg agctacccg 19

<210> SEQ ID NO 23
<211> LENGTH: 19
<212> TYPE: DNA
<213> ORGANISM: Artificial Sequence
<220> FEATURE:
<223> OTHER INFORMATION: SAMi-hDKK1#023

<400> SEQUENCE: 23
cgcagcggga gctacccgg 19

<210> SEQ ID NO 24
<211> LENGTH: 19
<212> TYPE: DNA
<213> ORGANISM: Artificial Sequence
<220> FEATURE:
<223> OTHER INFORMATION: SAMi-hDKK1#024

-continued

<400> SEQUENCE: 24
gagctacccg ggtctttgt 19

<210> SEQ ID NO 25
<211> LENGTH: 19
<212> TYPE: DNA
<213> ORGANISM: Artificial Sequence
<220> FEATURE:
<223> OTHER INFORMATION: SAMi-hDKK1#025

<400> SEQUENCE: 25
agctacccgg gtctttgtc 19

<210> SEQ ID NO 26
<211> LENGTH: 19
<212> TYPE: DNA
<213> ORGANISM: Artificial Sequence
<220> FEATURE:
<223> OTHER INFORMATION: SAMi-hDKK1#026

<400> SEQUENCE: 26
gctacccggg tctttgtcg 19

<210> SEQ ID NO 27
<211> LENGTH: 19
<212> TYPE: DNA
<213> ORGANISM: Artificial Sequence
<220> FEATURE:
<223> OTHER INFORMATION: SAMi-hDKK1#027

<400> SEQUENCE: 27
ctacccgggt ctttgtcgc 19

<210> SEQ ID NO 28
<211> LENGTH: 19
<212> TYPE: DNA
<213> ORGANISM: Artificial Sequence
<220> FEATURE:
<223> OTHER INFORMATION: SAMi-hDKK1#028

<400> SEQUENCE: 28
tacccgggtc tttgtcgcg 19

<210> SEQ ID NO 29
<211> LENGTH: 19
<212> TYPE: DNA
<213> ORGANISM: Artificial Sequence
<220> FEATURE:
<223> OTHER INFORMATION: SAMi-hDKK1#029

<400> SEQUENCE: 29
acccgggtct ttgtcgcga 19

<210> SEQ ID NO 30
<211> LENGTH: 19
<212> TYPE: DNA
<213> ORGANISM: Artificial Sequence
<220> FEATURE:
<223> OTHER INFORMATION: SAMi-hDKK1#030

<400> SEQUENCE: 30
cccgggtctt tgtcgcgat 19

<210> SEQ ID NO 31
<211> LENGTH: 19

-continued

<212> TYPE: DNA
<213> ORGANISM: Artificial Sequence
<220> FEATURE:
<223> OTHER INFORMATION: SAMi-hDKK1#031

<400> SEQUENCE: 31
ccgggtcttt gtcgcgatg 19

<210> SEQ ID NO 32
<211> LENGTH: 19
<212> TYPE: DNA
<213> ORGANISM: Artificial Sequence
<220> FEATURE:
<223> OTHER INFORMATION: SAMi-hDKK1#032

<400> SEQUENCE: 32
cgggtctttg tcgcgatgg 19

<210> SEQ ID NO 33
<211> LENGTH: 19
<212> TYPE: DNA
<213> ORGANISM: Artificial Sequence
<220> FEATURE:
<223> OTHER INFORMATION: SAMi-hDKK1#033

<400> SEQUENCE: 33
gggtctttgt cgcgatggt 19

<210> SEQ ID NO 34
<211> LENGTH: 19
<212> TYPE: DNA
<213> ORGANISM: Artificial Sequence
<220> FEATURE:
<223> OTHER INFORMATION: SAMi-hDKK1#034

<400> SEQUENCE: 34
ggtctttgtc gcgatggta 19

<210> SEQ ID NO 35
<211> LENGTH: 19
<212> TYPE: DNA
<213> ORGANISM: Artificial Sequence
<220> FEATURE:
<223> OTHER INFORMATION: SAMi-hDKK1#035

<400> SEQUENCE: 35
gtctttgtcg cgatggtag 19

<210> SEQ ID NO 36
<211> LENGTH: 19
<212> TYPE: DNA
<213> ORGANISM: Artificial Sequence
<220> FEATURE:
<223> OTHER INFORMATION: SAMi-hDKK1#036

<400> SEQUENCE: 36
tctttgtcgc gatggtagc 19

<210> SEQ ID NO 37
<211> LENGTH: 19
<212> TYPE: DNA
<213> ORGANISM: Artificial Sequence
<220> FEATURE:
<223> OTHER INFORMATION: SAMi-hDKK1#037

<400> SEQUENCE: 37

-continued ctttgtcgcg atggtagcg 19

<210> SEQ ID NO 38
<211> LENGTH: 19
<212> TYPE: DNA
<213> ORGANISM: Artificial Sequence
<220> FEATURE:
<223> OTHER INFORMATION: SAMi-hDKK1#038

<400> SEQUENCE: 38
tttgtcgcga tggtagcgg 19

<210> SEQ ID NO 39
<211> LENGTH: 19
<212> TYPE: DNA
<213> ORGANISM: Artificial Sequence
<220> FEATURE:
<223> OTHER INFORMATION: SAMi-hDKK1#039

<400> SEQUENCE: 39
ttgtcgcgat ggtagcggc 19

<210> SEQ ID NO 40
<211> LENGTH: 19
<212> TYPE: DNA
<213> ORGANISM: Artificial Sequence
<220> FEATURE:
<223> OTHER INFORMATION: SAMi-hDKK1#040

<400> SEQUENCE: 40
tgtcgcgatg gtagcggcg 19

<210> SEQ ID NO 41
<211> LENGTH: 19
<212> TYPE: DNA
<213> ORGANISM: Artificial Sequence
<220> FEATURE:
<223> OTHER INFORMATION: SAMi-hDKK1#041

<400> SEQUENCE: 41
ggagtgagcg ccaccttga 19

<210> SEQ ID NO 42
<211> LENGTH: 19
<212> TYPE: DNA
<213> ORGANISM: Artificial Sequence
<220> FEATURE:
<223> OTHER INFORMATION: SAMi-hDKK1#042

<400> SEQUENCE: 42
ccaccttgaa ctcggttct 19

<210> SEQ ID NO 43
<211> LENGTH: 19
<212> TYPE: DNA
<213> ORGANISM: Artificial Sequence
<220> FEATURE:
<223> OTHER INFORMATION: SAMi-hDKK1#043

<400> SEQUENCE: 43
caccttgaac tcggttctc 19

<210> SEQ ID NO 44
<211> LENGTH: 19
<212> TYPE: DNA
<213> ORGANISM: Artificial Sequence
<220> FEATURE:
<223> OTHER INFORMATION: SAMi-hDKK1#044

<400> SEQUENCE: 44
accttgaact cggttctca 19

<210> SEQ ID NO 45
<211> LENGTH: 19
<212> TYPE: DNA
<213> ORGANISM: Artificial Sequence
<220> FEATURE:
<223> OTHER INFORMATION: SAMi-hDKK1#045

<400> SEQUENCE: 45
ccttgaactc ggttctcaa 19

<210> SEQ ID NO 46
<211> LENGTH: 19
<212> TYPE: DNA
<213> ORGANISM: Artificial Sequence
<220> FEATURE:
<223> OTHER INFORMATION: SAMi-hDKK1#046

<400> SEQUENCE: 46
cttgaactcg gttctcaat 19

<210> SEQ ID NO 47
<211> LENGTH: 19
<212> TYPE: DNA
<213> ORGANISM: Artificial Sequence
<220> FEATURE:
<223> OTHER INFORMATION: SAMi-hDKK1#047

<400> SEQUENCE: 47
actcggttct caattccaa 19

<210> SEQ ID NO 48
<211> LENGTH: 19
<212> TYPE: DNA
<213> ORGANISM: Artificial Sequence
<220> FEATURE:
<223> OTHER INFORMATION: SAMi-hDKK1#048

<400> SEQUENCE: 48
gttctcaatt ccaacgcta 19

<210> SEQ ID NO 49
<211> LENGTH: 19
<212> TYPE: DNA
<213> ORGANISM: Artificial Sequence
<220> FEATURE:
<223> OTHER INFORMATION: SAMi-hDKK1#049

<400> SEQUENCE: 49
attccaacgc tatcaagaa 19

<210> SEQ ID NO 50
<211> LENGTH: 19
<212> TYPE: DNA
<213> ORGANISM: Artificial Sequence
<220> FEATURE:
<223> OTHER INFORMATION: SAMi-hDKK1#050

<400> SEQUENCE: 50
ttccaacgct atcaagaac 19

<210> SEQ ID NO 51
<211> LENGTH: 19
<212> TYPE: DNA
<213> ORGANISM: Artificial Sequence
<220> FEATURE:
<223> OTHER INFORMATION: SAMi-hDKK1#051

<400> SEQUENCE: 51
aagaacctgc ccccaccgc 19

<210> SEQ ID NO 52
<211> LENGTH: 19
<212> TYPE: DNA
<213> ORGANISM: Artificial Sequence
<220> FEATURE:
<223> OTHER INFORMATION: SAMi-hDKK1#052

<400> SEQUENCE: 52
agaacctgcc cccaccgct 19

<210> SEQ ID NO 53
<211> LENGTH: 19
<212> TYPE: DNA
<213> ORGANISM: Artificial Sequence
<220> FEATURE:
<223> OTHER INFORMATION: SAMi-hDKK1#053

<400> SEQUENCE: 53
gcgccgggaa tcctgtacc 19

<210> SEQ ID NO 54
<211> LENGTH: 19
<212> TYPE: DNA
<213> ORGANISM: Artificial Sequence
<220> FEATURE:
<223> OTHER INFORMATION: SAMi-hDKK1#054

<400> SEQUENCE: 54
cgccgggaat cctgtaccc 19

<210> SEQ ID NO 55
<211> LENGTH: 19
<212> TYPE: DNA
<213> ORGANISM: Artificial Sequence
<220> FEATURE:
<223> OTHER INFORMATION: SAMi-hDKK1#055

<400> SEQUENCE: 55
gccgggaatc ctgtacccg 19

<210> SEQ ID NO 56
<211> LENGTH: 19
<212> TYPE: DNA
<213> ORGANISM: Artificial Sequence
<220> FEATURE:
<223> OTHER INFORMATION: SAMi-hDKK1#056

<400> SEQUENCE: 56
atcctgtacc cgggcggga 19

<210> SEQ ID NO 57
<211> LENGTH: 19
<212> TYPE: DNA
<213> ORGANISM: Artificial Sequence
<220> FEATURE:
<223> OTHER INFORMATION: SAMi-hDKK1#057

<400> SEQUENCE: 57
tcctgtaccc gggcgggaa 19

<210> SEQ ID NO 58
<211> LENGTH: 19
<212> TYPE: DNA
<213> ORGANISM: Artificial Sequence
<220> FEATURE:
<223> OTHER INFORMATION: SAMi-hDKK1#058

<400> SEQUENCE: 58
cctgtacccg ggcgggaat 19

<210> SEQ ID NO 59
<211> LENGTH: 19
<212> TYPE: DNA
<213> ORGANISM: Artificial Sequence
<220> FEATURE:
<223> OTHER INFORMATION: SAMi-hDKK1#059

<400> SEQUENCE: 59
ctgtacccgg gcgggaata 19

<210> SEQ ID NO 60
<211> LENGTH: 19
<212> TYPE: DNA
<213> ORGANISM: Artificial Sequence
<220> FEATURE:
<223> OTHER INFORMATION: SAMi-hDKK1#060

<400> SEQUENCE: 60
tgtacccggg cgggaataa 19

<210> SEQ ID NO 61
<211> LENGTH: 19
<212> TYPE: DNA
<213> ORGANISM: Artificial Sequence
<220> FEATURE:
<223> OTHER INFORMATION: SAMi-hDKK1#061

<400> SEQUENCE: 61
gtacccgggc gggaataag 19

<210> SEQ ID NO 62
<211> LENGTH: 19
<212> TYPE: DNA
<213> ORGANISM: Artificial Sequence
<220> FEATURE:
<223> OTHER INFORMATION: SAMi-hDKK1#062

<400> SEQUENCE: 62
ccgggcggga ataagtacc 19

<210> SEQ ID NO 63
<211> LENGTH: 19
<212> TYPE: DNA
<213> ORGANISM: Artificial Sequence
<220> FEATURE:
<223> OTHER INFORMATION: SAMi-hDKK1#063

<400> SEQUENCE: 63
cgggcgggaa taagtacca 19

<210> SEQ ID NO 64

<211> LENGTH: 19
<212> TYPE: DNA
<213> ORGANISM: Artificial Sequence
<220> FEATURE:
<223> OTHER INFORMATION: SAMi-hDKK1#064

<400> SEQUENCE: 64
gggcgggaat aagtaccag 19

<210> SEQ ID NO 65
<211> LENGTH: 19
<212> TYPE: DNA
<213> ORGANISM: Artificial Sequence
<220> FEATURE:
<223> OTHER INFORMATION: SAMi-hDKK1#065

<400> SEQUENCE: 65
ggcgggaata agtaccaga 19

<210> SEQ ID NO 66
<211> LENGTH: 19
<212> TYPE: DNA
<213> ORGANISM: Artificial Sequence
<220> FEATURE:
<223> OTHER INFORMATION: SAMi-hDKK1#066

<400> SEQUENCE: 66
gcgggaataa gtaccagac 19

<210> SEQ ID NO 67
<211> LENGTH: 19
<212> TYPE: DNA
<213> ORGANISM: Artificial Sequence
<220> FEATURE:
<223> OTHER INFORMATION: SAMi-hDKK1#067

<400> SEQUENCE: 67
cgggaataag taccagacc 19

<210> SEQ ID NO 68
<211> LENGTH: 19
<212> TYPE: DNA
<213> ORGANISM: Artificial Sequence
<220> FEATURE:
<223> OTHER INFORMATION: SAMi-hDKK1#068

<400> SEQUENCE: 68
gggaataagt accagacca 19

<210> SEQ ID NO 69
<211> LENGTH: 19
<212> TYPE: DNA
<213> ORGANISM: Artificial Sequence
<220> FEATURE:
<223> OTHER INFORMATION: SAMi-hDKK1#069

<400> SEQUENCE: 69
ggaataagta ccagaccat 19

<210> SEQ ID NO 70
<211> LENGTH: 19
<212> TYPE: DNA
<213> ORGANISM: Artificial Sequence
<220> FEATURE:
<223> OTHER INFORMATION: SAMi-hDKK1#070

<400> SEQUENCE: 70
gaataagtac cagaccatt 19

<210> SEQ ID NO 71
<211> LENGTH: 19
<212> TYPE: DNA
<213> ORGANISM: Artificial Sequence
<220> FEATURE:
<223> OTHER INFORMATION: SAMi-hDKK1#071

<400> SEQUENCE: 71
aataagtacc agaccattg 19

<210> SEQ ID NO 72
<211> LENGTH: 19
<212> TYPE: DNA
<213> ORGANISM: Artificial Sequence
<220> FEATURE:
<223> OTHER INFORMATION: SAMi-hDKK1#072

<400> SEQUENCE: 72
ataagtacca gaccattga 19

<210> SEQ ID NO 73
<211> LENGTH: 19
<212> TYPE: DNA
<213> ORGANISM: Artificial Sequence
<220> FEATURE:
<223> OTHER INFORMATION: SAMi-hDKK1#073

<400> SEQUENCE: 73
taagtaccag accattgac 19

<210> SEQ ID NO 74
<211> LENGTH: 19
<212> TYPE: DNA
<213> ORGANISM: Artificial Sequence
<220> FEATURE:
<223> OTHER INFORMATION: SAMi-hDKK1#074

<400> SEQUENCE: 74
aagtaccaga ccattgaca 19

<210> SEQ ID NO 75
<211> LENGTH: 19
<212> TYPE: DNA
<213> ORGANISM: Artificial Sequence
<220> FEATURE:
<223> OTHER INFORMATION: SAMi-hDKK1#075

<400> SEQUENCE: 75
agtaccagac cattgacaa 19

<210> SEQ ID NO 76
<211> LENGTH: 19
<212> TYPE: DNA
<213> ORGANISM: Artificial Sequence
<220> FEATURE:
<223> OTHER INFORMATION: SAMi-hDKK1#076

<400> SEQUENCE: 76
ccagaccatt gacaactac 19

<210> SEQ ID NO 77
<211> LENGTH: 19
<212> TYPE: DNA

-continued

<213> ORGANISM: Artificial Sequence
<220> FEATURE:
<223> OTHER INFORMATION: SAMi-hDKK1#077

<400> SEQUENCE: 77
cagaccattg acaactacc 19

<210> SEQ ID NO 78
<211> LENGTH: 19
<212> TYPE: DNA
<213> ORGANISM: Artificial Sequence
<220> FEATURE:
<223> OTHER INFORMATION: SAMi-hDKK1#078

<400> SEQUENCE: 78
agaccattga caactacca 19

<210> SEQ ID NO 79
<211> LENGTH: 19
<212> TYPE: DNA
<213> ORGANISM: Artificial Sequence
<220> FEATURE:
<223> OTHER INFORMATION: SAMi-hDKK1#079

<400> SEQUENCE: 79
cattgacaac taccagccg 19

<210> SEQ ID NO 80
<211> LENGTH: 19
<212> TYPE: DNA
<213> ORGANISM: Artificial Sequence
<220> FEATURE:
<223> OTHER INFORMATION: SAMi-hDKK1#080

<400> SEQUENCE: 80
attgacaact accagccgt 19

<210> SEQ ID NO 81
<211> LENGTH: 19
<212> TYPE: DNA
<213> ORGANISM: Artificial Sequence
<220> FEATURE:
<223> OTHER INFORMATION: SAMi-hDKK1#081

<400> SEQUENCE: 81
ttgacaacta ccagccgta 19

<210> SEQ ID NO 82
<211> LENGTH: 19
<212> TYPE: DNA
<213> ORGANISM: Artificial Sequence
<220> FEATURE:
<223> OTHER INFORMATION: SAMi-hDKK1#082

<400> SEQUENCE: 82
tgacaactac cagccgtac 19

<210> SEQ ID NO 83
<211> LENGTH: 19
<212> TYPE: DNA
<213> ORGANISM: Artificial Sequence
<220> FEATURE:
<223> OTHER INFORMATION: SAMi-hDKK1#083

<400> SEQUENCE: 83
gacaactacc agccgtacc 19

<210> SEQ ID NO 84
<211> LENGTH: 19
<212> TYPE: DNA
<213> ORGANISM: Artificial Sequence
<220> FEATURE:
<223> OTHER INFORMATION: SAMi-hDKK1#084

<400> SEQUENCE: 84
acaactacca gccgtaccc 19

<210> SEQ ID NO 85
<211> LENGTH: 19
<212> TYPE: DNA
<213> ORGANISM: Artificial Sequence
<220> FEATURE:
<223> OTHER INFORMATION: SAMi-hDKK1#085

<400> SEQUENCE: 85
caactaccag ccgtacccg 19

<210> SEQ ID NO 86
<211> LENGTH: 19
<212> TYPE: DNA
<213> ORGANISM: Artificial Sequence
<220> FEATURE:
<223> OTHER INFORMATION: SAMi-hDKK1#086

<400> SEQUENCE: 86
aactaccagc cgtacccgt 19

<210> SEQ ID NO 87
<211> LENGTH: 19
<212> TYPE: DNA
<213> ORGANISM: Artificial Sequence
<220> FEATURE:
<223> OTHER INFORMATION: SAMi-hDKK1#087

<400> SEQUENCE: 87
agccgtaccc gtgcgcaga 19

<210> SEQ ID NO 88
<211> LENGTH: 19
<212> TYPE: DNA
<213> ORGANISM: Artificial Sequence
<220> FEATURE:
<223> OTHER INFORMATION: SAMi-hDKK1#088

<400> SEQUENCE: 88
gccgtacccg tgcgcagag 19

<210> SEQ ID NO 89
<211> LENGTH: 19
<212> TYPE: DNA
<213> ORGANISM: Artificial Sequence
<220> FEATURE:
<223> OTHER INFORMATION: SAMi-hDKK1#089

<400> SEQUENCE: 89
ccgtacccgt gcgcagagg 19

<210> SEQ ID NO 90
<211> LENGTH: 19
<212> TYPE: DNA
<213> ORGANISM: Artificial Sequence
<220> FEATURE:

<223> OTHER INFORMATION: SAMi-hDKK1#090

<400> SEQUENCE: 90
cgtacccgtg cgcagagga 19

<210> SEQ ID NO 91
<211> LENGTH: 19
<212> TYPE: DNA
<213> ORGANISM: Artificial Sequence
<220> FEATURE:
<223> OTHER INFORMATION: SAMi-hDKK1#091

<400> SEQUENCE: 91
gtacccgtgc gcagaggac 19

<210> SEQ ID NO 92
<211> LENGTH: 19
<212> TYPE: DNA
<213> ORGANISM: Artificial Sequence
<220> FEATURE:
<223> OTHER INFORMATION: SAMi-hDKK1#092

<400> SEQUENCE: 92
tacccgtgcg cagaggacg 19

<210> SEQ ID NO 93
<211> LENGTH: 19
<212> TYPE: DNA
<213> ORGANISM: Artificial Sequence
<220> FEATURE:
<223> OTHER INFORMATION: SAMi-hDKK1#093

<400> SEQUENCE: 93
gacgaggagt gcggcactg 19

<210> SEQ ID NO 94
<211> LENGTH: 19
<212> TYPE: DNA
<213> ORGANISM: Artificial Sequence
<220> FEATURE:
<223> OTHER INFORMATION: SAMi-hDKK1#094

<400> SEQUENCE: 94
acgaggagtg cggcactga 19

<210> SEQ ID NO 95
<211> LENGTH: 19
<212> TYPE: DNA
<213> ORGANISM: Artificial Sequence
<220> FEATURE:
<223> OTHER INFORMATION: SAMi-hDKK1#095

<400> SEQUENCE: 95
cgaggagtgc ggcactgat 19

<210> SEQ ID NO 96
<211> LENGTH: 19
<212> TYPE: DNA
<213> ORGANISM: Artificial Sequence
<220> FEATURE:
<223> OTHER INFORMATION: SAMi-hDKK1#096

<400> SEQUENCE: 96
gaggagtgcg gcactgatg 19

<210> SEQ ID NO 97
<211> LENGTH: 19
<212> TYPE: DNA
<213> ORGANISM: Artificial Sequence
<220> FEATURE:
<223> OTHER INFORMATION: SAMi-hDKK1#097

<400> SEQUENCE: 97
aggagtgcgg cactgatga 19

<210> SEQ ID NO 98
<211> LENGTH: 19
<212> TYPE: DNA
<213> ORGANISM: Artificial Sequence
<220> FEATURE:
<223> OTHER INFORMATION: SAMi-hDKK1#098

<400> SEQUENCE: 98
ggagtgcggc actgatgag 19

<210> SEQ ID NO 99
<211> LENGTH: 19
<212> TYPE: DNA
<213> ORGANISM: Artificial Sequence
<220> FEATURE:
<223> OTHER INFORMATION: SAMi-hDKK1#099

<400> SEQUENCE: 99
gagtgcggca ctgatgagt 19

<210> SEQ ID NO 100
<211> LENGTH: 19
<212> TYPE: DNA
<213> ORGANISM: Artificial Sequence
<220> FEATURE:
<223> OTHER INFORMATION: SAMi-hDKK1#100

<400> SEQUENCE: 100
agtgcggcac tgatgagta 19

<210> SEQ ID NO 101
<211> LENGTH: 19
<212> TYPE: DNA
<213> ORGANISM: Artificial Sequence
<220> FEATURE:
<223> OTHER INFORMATION: SAMi-hDKK1#101

<400> SEQUENCE: 101
gtgcggcact gatgagtac 19

<210> SEQ ID NO 102
<211> LENGTH: 19
<212> TYPE: DNA
<213> ORGANISM: Artificial Sequence
<220> FEATURE:
<223> OTHER INFORMATION: SAMi-hDKK1#102

<400> SEQUENCE: 102
tgcggcactg atgagtact 19

<210> SEQ ID NO 103
<211> LENGTH: 19
<212> TYPE: DNA
<213> ORGANISM: Artificial Sequence
<220> FEATURE:
<223> OTHER INFORMATION: SAMi-hDKK1#103

-continued

<400> SEQUENCE: 103
gcggcactga tgagtactg 19

<210> SEQ ID NO 104
<211> LENGTH: 19
<212> TYPE: DNA
<213> ORGANISM: Artificial Sequence
<220> FEATURE:
<223> OTHER INFORMATION: SAMi-hDKK1#104

<400> SEQUENCE: 104
cactgatgag tactgcgct 19

<210> SEQ ID NO 105
<211> LENGTH: 19
<212> TYPE: DNA
<213> ORGANISM: Artificial Sequence
<220> FEATURE:
<223> OTHER INFORMATION: SAMi-hDKK1#105

<400> SEQUENCE: 105
gatgagtact gcgctagtc 19

<210> SEQ ID NO 106
<211> LENGTH: 19
<212> TYPE: DNA
<213> ORGANISM: Artificial Sequence
<220> FEATURE:
<223> OTHER INFORMATION: SAMi-hDKK1#106

<400> SEQUENCE: 106
agtactgcgc tagtcccac 19

<210> SEQ ID NO 107
<211> LENGTH: 19
<212> TYPE: DNA
<213> ORGANISM: Artificial Sequence
<220> FEATURE:
<223> OTHER INFORMATION: SAMi-hDKK1#107

<400> SEQUENCE: 107
ctgcgctagt cccacccgc 19

<210> SEQ ID NO 108
<211> LENGTH: 19
<212> TYPE: DNA
<213> ORGANISM: Artificial Sequence
<220> FEATURE:
<223> OTHER INFORMATION: SAMi-hDKK1#108

<400> SEQUENCE: 108
tgcgctagtc ccacccgcg 19

<210> SEQ ID NO 109
<211> LENGTH: 19
<212> TYPE: DNA
<213> ORGANISM: Artificial Sequence
<220> FEATURE:
<223> OTHER INFORMATION: SAMi-hDKK1#109

<400> SEQUENCE: 109
gcgctagtcc cacccgcgg 19

<210> SEQ ID NO 110
<211> LENGTH: 19

<212> TYPE: DNA
<213> ORGANISM: Artificial Sequence
<220> FEATURE:
<223> OTHER INFORMATION: SAMi-hDKK1#110

<400> SEQUENCE: 110
cgctagtccc acccgcgga 19

<210> SEQ ID NO 111
<211> LENGTH: 19
<212> TYPE: DNA
<213> ORGANISM: Artificial Sequence
<220> FEATURE:
<223> OTHER INFORMATION: SAMi-hDKK1#111

<400> SEQUENCE: 111
aggggacgca ggcgtgcaa 19

<210> SEQ ID NO 112
<211> LENGTH: 19
<212> TYPE: DNA
<213> ORGANISM: Artificial Sequence
<220> FEATURE:
<223> OTHER INFORMATION: SAMi-hDKK1#112

<400> SEQUENCE: 112
ggggacgcag gcgtgcaaa 19

<210> SEQ ID NO 113
<211> LENGTH: 19
<212> TYPE: DNA
<213> ORGANISM: Artificial Sequence
<220> FEATURE:
<223> OTHER INFORMATION: SAMi-hDKK1#113

<400> SEQUENCE: 113
gggacgcagg cgtgcaaat 19

<210> SEQ ID NO 114
<211> LENGTH: 19
<212> TYPE: DNA
<213> ORGANISM: Artificial Sequence
<220> FEATURE:
<223> OTHER INFORMATION: SAMi-hDKK1#114

<400> SEQUENCE: 114
ggacgcaggc gtgcaaatc 19

<210> SEQ ID NO 115
<211> LENGTH: 19
<212> TYPE: DNA
<213> ORGANISM: Artificial Sequence
<220> FEATURE:
<223> OTHER INFORMATION: SAMi-hDKK1#115

<400> SEQUENCE: 115
gacgcaggcg tgcaaatct 19

<210> SEQ ID NO 116
<211> LENGTH: 19
<212> TYPE: DNA
<213> ORGANISM: Artificial Sequence
<220> FEATURE:
<223> OTHER INFORMATION: SAMi-hDKK1#116

<400> SEQUENCE: 116

-continued acgcaggcgt gcaaatctg 19

<210> SEQ ID NO 117
<211> LENGTH: 19
<212> TYPE: DNA
<213> ORGANISM: Artificial Sequence
<220> FEATURE:
<223> OTHER INFORMATION: SAMi-hDKK1#117

<400> SEQUENCE: 117
cgcaggcgtg caaatctgt 19

<210> SEQ ID NO 118
<211> LENGTH: 19
<212> TYPE: DNA
<213> ORGANISM: Artificial Sequence
<220> FEATURE:
<223> OTHER INFORMATION: SAMi-hDKK1#118

<400> SEQUENCE: 118
gcaaatctgt ctcgcctgc 19

<210> SEQ ID NO 119
<211> LENGTH: 19
<212> TYPE: DNA
<213> ORGANISM: Artificial Sequence
<220> FEATURE:
<223> OTHER INFORMATION: SAMi-hDKK1#119

<400> SEQUENCE: 119
caaatctgtc tcgcctgca 19

<210> SEQ ID NO 120
<211> LENGTH: 19
<212> TYPE: DNA
<213> ORGANISM: Artificial Sequence
<220> FEATURE:
<223> OTHER INFORMATION: SAMi-hDKK1#120

<400> SEQUENCE: 120
aaatctgtct cgcctgcag 19

<210> SEQ ID NO 121
<211> LENGTH: 19
<212> TYPE: DNA
<213> ORGANISM: Artificial Sequence
<220> FEATURE:
<223> OTHER INFORMATION: SAMi-hDKK1#121

<400> SEQUENCE: 121
ggaagcgccg aaaacgctg 19

<210> SEQ ID NO 122
<211> LENGTH: 19
<212> TYPE: DNA
<213> ORGANISM: Artificial Sequence
<220> FEATURE:
<223> OTHER INFORMATION: SAMi-hDKK1#122

<400> SEQUENCE: 122
gaagcgccga aaacgctgc 19

<210> SEQ ID NO 123
<211> LENGTH: 19
<212> TYPE: DNA
<213> ORGANISM: Artificial Sequence
<220> FEATURE:
<223> OTHER INFORMATION: SAMi-hDKK1#123

<400> SEQUENCE: 123
aagcgccgaa aacgctgca 19

<210> SEQ ID NO 124
<211> LENGTH: 19
<212> TYPE: DNA
<213> ORGANISM: Artificial Sequence
<220> FEATURE:
<223> OTHER INFORMATION: SAMi-hDKK1#124

<400> SEQUENCE: 124
agcgccgaaa acgctgcat 19

<210> SEQ ID NO 125
<211> LENGTH: 19
<212> TYPE: DNA
<213> ORGANISM: Artificial Sequence
<220> FEATURE:
<223> OTHER INFORMATION: SAMi-hDKK1#125

<400> SEQUENCE: 125
gcgccgaaaa cgctgcatg 19

<210> SEQ ID NO 126
<211> LENGTH: 19
<212> TYPE: DNA
<213> ORGANISM: Artificial Sequence
<220> FEATURE:
<223> OTHER INFORMATION: SAMi-hDKK1#126

<400> SEQUENCE: 126
cgccgaaaac gctgcatgc 19

<210> SEQ ID NO 127
<211> LENGTH: 19
<212> TYPE: DNA
<213> ORGANISM: Artificial Sequence
<220> FEATURE:
<223> OTHER INFORMATION: SAMi-hDKK1#127

<400> SEQUENCE: 127
gccgaaaacg ctgcatgcg 19

<210> SEQ ID NO 128
<211> LENGTH: 19
<212> TYPE: DNA
<213> ORGANISM: Artificial Sequence
<220> FEATURE:
<223> OTHER INFORMATION: SAMi-hDKK1#128

<400> SEQUENCE: 128
ccgaaaacgc tgcatgcgt 19

<210> SEQ ID NO 129
<211> LENGTH: 19
<212> TYPE: DNA
<213> ORGANISM: Artificial Sequence
<220> FEATURE:
<223> OTHER INFORMATION: SAMi-hDKK1#129

<400> SEQUENCE: 129
aaacgctgca tgcgtcacg 19

<210> SEQ ID NO 130
<211> LENGTH: 19
<212> TYPE: DNA
<213> ORGANISM: Artificial Sequence
<220> FEATURE:
<223> OTHER INFORMATION: SAMi-hDKK1#130

<400> SEQUENCE: 130
aacgctgcat gcgtcacgc 19

<210> SEQ ID NO 131
<211> LENGTH: 19
<212> TYPE: DNA
<213> ORGANISM: Artificial Sequence
<220> FEATURE:
<223> OTHER INFORMATION: SAMi-hDKK1#131

<400> SEQUENCE: 131
acgctgcatg cgtcacgct 19

<210> SEQ ID NO 132
<211> LENGTH: 19
<212> TYPE: DNA
<213> ORGANISM: Artificial Sequence
<220> FEATURE:
<223> OTHER INFORMATION: SAMi-hDKK1#132

<400> SEQUENCE: 132
cgctgcatgc gtcacgcta 19

<210> SEQ ID NO 133
<211> LENGTH: 19
<212> TYPE: DNA
<213> ORGANISM: Artificial Sequence
<220> FEATURE:
<223> OTHER INFORMATION: SAMi-hDKK1#133

<400> SEQUENCE: 133
gctgcatgcg tcacgctat 19

<210> SEQ ID NO 134
<211> LENGTH: 19
<212> TYPE: DNA
<213> ORGANISM: Artificial Sequence
<220> FEATURE:
<223> OTHER INFORMATION: SAMi-hDKK1#134

<400> SEQUENCE: 134
ctgcatgcgt cacgctatg 19

<210> SEQ ID NO 135
<211> LENGTH: 19
<212> TYPE: DNA
<213> ORGANISM: Artificial Sequence
<220> FEATURE:
<223> OTHER INFORMATION: SAMi-hDKK1#135

<400> SEQUENCE: 135
tgcatgcgtc acgctatgt 19

<210> SEQ ID NO 136
<211> LENGTH: 19
<212> TYPE: DNA
<213> ORGANISM: Artificial Sequence
<220> FEATURE:
<223> OTHER INFORMATION: SAMi-hDKK1#136

<400> SEQUENCE: 136
gcatgcgtca cgctatgtg 19

<210> SEQ ID NO 137
<211> LENGTH: 19
<212> TYPE: DNA
<213> ORGANISM: Artificial Sequence
<220> FEATURE:
<223> OTHER INFORMATION: SAMi-hDKK1#137

<400> SEQUENCE: 137
catgcgtcac gctatgtgc 19

<210> SEQ ID NO 138
<211> LENGTH: 19
<212> TYPE: DNA
<213> ORGANISM: Artificial Sequence
<220> FEATURE:
<223> OTHER INFORMATION: SAMi-hDKK1#138

<400> SEQUENCE: 138
atgcgtcacg ctatgtgct 19

<210> SEQ ID NO 139
<211> LENGTH: 19
<212> TYPE: DNA
<213> ORGANISM: Artificial Sequence
<220> FEATURE:
<223> OTHER INFORMATION: SAMi-hDKK1#139

<400> SEQUENCE: 139
tgcgtcacgc tatgtgctg 19

<210> SEQ ID NO 140
<211> LENGTH: 19
<212> TYPE: DNA
<213> ORGANISM: Artificial Sequence
<220> FEATURE:
<223> OTHER INFORMATION: SAMi-hDKK1#140

<400> SEQUENCE: 140
gcgtcacgct atgtgctgc 19

<210> SEQ ID NO 141
<211> LENGTH: 19
<212> TYPE: DNA
<213> ORGANISM: Artificial Sequence
<220> FEATURE:
<223> OTHER INFORMATION: SAMi-hDKK1#141

<400> SEQUENCE: 141
cgtcacgcta tgtgctgcc 19

<210> SEQ ID NO 142
<211> LENGTH: 19
<212> TYPE: DNA
<213> ORGANISM: Artificial Sequence
<220> FEATURE:
<223> OTHER INFORMATION: SAMi-hDKK1#142

<400> SEQUENCE: 142
gtcacgctat gtgctgccc 19

<210> SEQ ID NO 143

<211> LENGTH: 19
<212> TYPE: DNA
<213> ORGANISM: Artificial Sequence
<220> FEATURE:
<223> OTHER INFORMATION: SAMi-hDKK1#143

<400> SEQUENCE: 143
tcacgctatg tgctgcccc 19

<210> SEQ ID NO 144
<211> LENGTH: 19
<212> TYPE: DNA
<213> ORGANISM: Artificial Sequence
<220> FEATURE:
<223> OTHER INFORMATION: SAMi-hDKK1#144

<400> SEQUENCE: 144
cacgctatgt gctgccccg 19

<210> SEQ ID NO 145
<211> LENGTH: 19
<212> TYPE: DNA
<213> ORGANISM: Artificial Sequence
<220> FEATURE:
<223> OTHER INFORMATION: SAMi-hDKK1#145

<400> SEQUENCE: 145
acgctatgtg ctgccccgg 19

<210> SEQ ID NO 146
<211> LENGTH: 19
<212> TYPE: DNA
<213> ORGANISM: Artificial Sequence
<220> FEATURE:
<223> OTHER INFORMATION: SAMi-hDKK1#146

<400> SEQUENCE: 146
cgctatgtgc tgccccggg 19

<210> SEQ ID NO 147
<211> LENGTH: 19
<212> TYPE: DNA
<213> ORGANISM: Artificial Sequence
<220> FEATURE:
<223> OTHER INFORMATION: SAMi-hDKK1#147

<400> SEQUENCE: 147
gctatgtgct gccccggga 19

<210> SEQ ID NO 148
<211> LENGTH: 19
<212> TYPE: DNA
<213> ORGANISM: Artificial Sequence
<220> FEATURE:
<223> OTHER INFORMATION: SAMi-hDKK1#148

<400> SEQUENCE: 148
gtgctgcccc gggaattac 19

<210> SEQ ID NO 149
<211> LENGTH: 19
<212> TYPE: DNA
<213> ORGANISM: Artificial Sequence
<220> FEATURE:
<223> OTHER INFORMATION: SAMi-hDKK1#149

<400> SEQUENCE: 149
tgctgccccg ggaattact 19

<210> SEQ ID NO 150
<211> LENGTH: 19
<212> TYPE: DNA
<213> ORGANISM: Artificial Sequence
<220> FEATURE:
<223> OTHER INFORMATION: SAMi-hDKK1#150

<400> SEQUENCE: 150
gctgccccgg gaattactg 19

<210> SEQ ID NO 151
<211> LENGTH: 19
<212> TYPE: DNA
<213> ORGANISM: Artificial Sequence
<220> FEATURE:
<223> OTHER INFORMATION: SAMi-hDKK1#151

<400> SEQUENCE: 151
ctgccccggg aattactgc 19

<210> SEQ ID NO 152
<211> LENGTH: 19
<212> TYPE: DNA
<213> ORGANISM: Artificial Sequence
<220> FEATURE:
<223> OTHER INFORMATION: SAMi-hDKK1#152

<400> SEQUENCE: 152
tgccccggga attactgca 19

<210> SEQ ID NO 153
<211> LENGTH: 19
<212> TYPE: DNA
<213> ORGANISM: Artificial Sequence
<220> FEATURE:
<223> OTHER INFORMATION: SAMi-hDKK1#153

<400> SEQUENCE: 153
gccccgggaa ttactgcaa 19

<210> SEQ ID NO 154
<211> LENGTH: 19
<212> TYPE: DNA
<213> ORGANISM: Artificial Sequence
<220> FEATURE:
<223> OTHER INFORMATION: SAMi-hDKK1#154

<400> SEQUENCE: 154
ccccgggaat tactgcaaa 19

<210> SEQ ID NO 155
<211> LENGTH: 19
<212> TYPE: DNA
<213> ORGANISM: Artificial Sequence
<220> FEATURE:
<223> OTHER INFORMATION: SAMi-hDKK1#155

<400> SEQUENCE: 155
ggaatatgtg tgtcttctg 19

<210> SEQ ID NO 156
<211> LENGTH: 19
<212> TYPE: DNA

<213> ORGANISM: Artificial Sequence
<220> FEATURE:
<223> OTHER INFORMATION: SAMi-hDKK1#156

<400> SEQUENCE: 156
ctttggtaat gatcatagc 19

<210> SEQ ID NO 157
<211> LENGTH: 19
<212> TYPE: DNA
<213> ORGANISM: Artificial Sequence
<220> FEATURE:
<223> OTHER INFORMATION: SAMi-hDKK1#157

<400> SEQUENCE: 157
tttggtaatg atcatagca 19

<210> SEQ ID NO 158
<211> LENGTH: 19
<212> TYPE: DNA
<213> ORGANISM: Artificial Sequence
<220> FEATURE:
<223> OTHER INFORMATION: SAMi-hDKK1#158

<400> SEQUENCE: 158
ttggtaatga tcatagcac 19

<210> SEQ ID NO 159
<211> LENGTH: 19
<212> TYPE: DNA
<213> ORGANISM: Artificial Sequence
<220> FEATURE:
<223> OTHER INFORMATION: SAMi-hDKK1#159

<400> SEQUENCE: 159
tggtaatgat catagcacc 19

<210> SEQ ID NO 160
<211> LENGTH: 19
<212> TYPE: DNA
<213> ORGANISM: Artificial Sequence
<220> FEATURE:
<223> OTHER INFORMATION: SAMi-hDKK1#160

<400> SEQUENCE: 160
tgatcatagc accttggat 19

<210> SEQ ID NO 161
<211> LENGTH: 19
<212> TYPE: DNA
<213> ORGANISM: Artificial Sequence
<220> FEATURE:
<223> OTHER INFORMATION: SAMi-hDKK1#161

<400> SEQUENCE: 161
gatcatagca ccttggatg 19

<210> SEQ ID NO 162
<211> LENGTH: 19
<212> TYPE: DNA
<213> ORGANISM: Artificial Sequence
<220> FEATURE:
<223> OTHER INFORMATION: SAMi-hDKK1#162

<400> SEQUENCE: 162
atcatagcac cttggatgg 19

<210> SEQ ID NO 163
<211> LENGTH: 19
<212> TYPE: DNA
<213> ORGANISM: Artificial Sequence
<220> FEATURE:
<223> OTHER INFORMATION: SAMi-hDKK1#163

<400> SEQUENCE: 163
tcatagcacc ttggatggg 19

<210> SEQ ID NO 164
<211> LENGTH: 19
<212> TYPE: DNA
<213> ORGANISM: Artificial Sequence
<220> FEATURE:
<223> OTHER INFORMATION: SAMi-hDKK1#164

<400> SEQUENCE: 164
catagcacct tggatgggt 19

<210> SEQ ID NO 165
<211> LENGTH: 19
<212> TYPE: DNA
<213> ORGANISM: Artificial Sequence
<220> FEATURE:
<223> OTHER INFORMATION: SAMi-hDKK1#165

<400> SEQUENCE: 165
gcaccttgga tgggtattc 19

<210> SEQ ID NO 166
<211> LENGTH: 19
<212> TYPE: DNA
<213> ORGANISM: Artificial Sequence
<220> FEATURE:
<223> OTHER INFORMATION: SAMi-hDKK1#166

<400> SEQUENCE: 166
caccttggat gggtattcc 19

<210> SEQ ID NO 167
<211> LENGTH: 19
<212> TYPE: DNA
<213> ORGANISM: Artificial Sequence
<220> FEATURE:
<223> OTHER INFORMATION: SAMi-hDKK1#167

<400> SEQUENCE: 167
accttggatg ggtattcca 19

<210> SEQ ID NO 168
<211> LENGTH: 19
<212> TYPE: DNA
<213> ORGANISM: Artificial Sequence
<220> FEATURE:
<223> OTHER INFORMATION: SAMi-hDKK1#168

<400> SEQUENCE: 168
tggatgggta ttccagaag 19

<210> SEQ ID NO 169
<211> LENGTH: 19
<212> TYPE: DNA
<213> ORGANISM: Artificial Sequence
<220> FEATURE:

<223> OTHER INFORMATION: SAMi-hDKK1#169

<400> SEQUENCE: 169
ggatgggtat tccagaaga 19

<210> SEQ ID NO 170
<211> LENGTH: 19
<212> TYPE: DNA
<213> ORGANISM: Artificial Sequence
<220> FEATURE:
<223> OTHER INFORMATION: SAMi-hDKK1#170

<400> SEQUENCE: 170
caaaggacaa gaaggttct 19

<210> SEQ ID NO 171
<211> LENGTH: 19
<212> TYPE: DNA
<213> ORGANISM: Artificial Sequence
<220> FEATURE:
<223> OTHER INFORMATION: SAMi-hDKK1#171

<400> SEQUENCE: 171
tctgtttgtc tccggtcat 19

<210> SEQ ID NO 172
<211> LENGTH: 19
<212> TYPE: DNA
<213> ORGANISM: Artificial Sequence
<220> FEATURE:
<223> OTHER INFORMATION: SAMi-hDKK1#172

<400> SEQUENCE: 172
ctgtttgtct ccggtcatc 19

<210> SEQ ID NO 173
<211> LENGTH: 19
<212> TYPE: DNA
<213> ORGANISM: Artificial Sequence
<220> FEATURE:
<223> OTHER INFORMATION: SAMi-hDKK1#173

<400> SEQUENCE: 173
tgtttgtctc cggtcatca 19

<210> SEQ ID NO 174
<211> LENGTH: 19
<212> TYPE: DNA
<213> ORGANISM: Artificial Sequence
<220> FEATURE:
<223> OTHER INFORMATION: SAMi-hDKK1#174

<400> SEQUENCE: 174
tccggtcatc agactgtgc 19

<210> SEQ ID NO 175
<211> LENGTH: 19
<212> TYPE: DNA
<213> ORGANISM: Artificial Sequence
<220> FEATURE:
<223> OTHER INFORMATION: SAMi-hDKK1#175

<400> SEQUENCE: 175
gattgtgttg tgctagaca 19

<210> SEQ ID NO 176
<211> LENGTH: 19
<212> TYPE: DNA
<213> ORGANISM: Artificial Sequence
<220> FEATURE:
<223> OTHER INFORMATION: SAMi-hDKK1#176

<400> SEQUENCE: 176
attgtgttgt gctagacac 19

<210> SEQ ID NO 177
<211> LENGTH: 19
<212> TYPE: DNA
<213> ORGANISM: Artificial Sequence
<220> FEATURE:
<223> OTHER INFORMATION: SAMi-hDKK1#177

<400> SEQUENCE: 177
ttgtgttgtg ctagacact 19

<210> SEQ ID NO 178
<211> LENGTH: 19
<212> TYPE: DNA
<213> ORGANISM: Artificial Sequence
<220> FEATURE:
<223> OTHER INFORMATION: SAMi-hDKK1#178

<400> SEQUENCE: 178
tgtgttgtgc tagacactt 19

<210> SEQ ID NO 179
<211> LENGTH: 19
<212> TYPE: DNA
<213> ORGANISM: Artificial Sequence
<220> FEATURE:
<223> OTHER INFORMATION: SAMi-hDKK1#179

<400> SEQUENCE: 179
gtgttgtgct agacacttc 19

<210> SEQ ID NO 180
<211> LENGTH: 19
<212> TYPE: DNA
<213> ORGANISM: Artificial Sequence
<220> FEATURE:
<223> OTHER INFORMATION: SAMi-hDKK1#180

<400> SEQUENCE: 180
tgttgtgcta gacacttct 19

<210> SEQ ID NO 181
<211> LENGTH: 19
<212> TYPE: DNA
<213> ORGANISM: Artificial Sequence
<220> FEATURE:
<223> OTHER INFORMATION: SAMi-hDKK1#181

<400> SEQUENCE: 181
gttgtgctag acacttctg 19

<210> SEQ ID NO 182
<211> LENGTH: 19
<212> TYPE: DNA
<213> ORGANISM: Artificial Sequence
<220> FEATURE:
<223> OTHER INFORMATION: SAMi-hDKK1#182

<400> SEQUENCE: 182
ttgtgctaga cacttctgg 19

<210> SEQ ID NO 183
<211> LENGTH: 19
<212> TYPE: DNA
<213> ORGANISM: Artificial Sequence
<220> FEATURE:
<223> OTHER INFORMATION: SAMi-hDKK1#183

<400> SEQUENCE: 183
agacacttct ggtccaaga 19

<210> SEQ ID NO 184
<211> LENGTH: 19
<212> TYPE: DNA
<213> ORGANISM: Artificial Sequence
<220> FEATURE:
<223> OTHER INFORMATION: SAMi-hDKK1#184

<400> SEQUENCE: 184
gacacttctg gtccaagat 19

<210> SEQ ID NO 185
<211> LENGTH: 19
<212> TYPE: DNA
<213> ORGANISM: Artificial Sequence
<220> FEATURE:
<223> OTHER INFORMATION: SAMi-hDKK1#185

<400> SEQUENCE: 185
ggtccaagat ctgtaaacc 19

<210> SEQ ID NO 186
<211> LENGTH: 19
<212> TYPE: DNA
<213> ORGANISM: Artificial Sequence
<220> FEATURE:
<223> OTHER INFORMATION: SAMi-hDKK1#186

<400> SEQUENCE: 186
gtccaagatc tgtaaacct 19

<210> SEQ ID NO 187
<211> LENGTH: 19
<212> TYPE: DNA
<213> ORGANISM: Artificial Sequence
<220> FEATURE:
<223> OTHER INFORMATION: SAMi-hDKK1#187

<400> SEQUENCE: 187
tccaagatct gtaaacctg 19

<210> SEQ ID NO 188
<211> LENGTH: 19
<212> TYPE: DNA
<213> ORGANISM: Artificial Sequence
<220> FEATURE:
<223> OTHER INFORMATION: SAMi-hDKK1#188

<400> SEQUENCE: 188
gcataggaga aaaggctct 19

<210> SEQ ID NO 189
<211> LENGTH: 19

-continued

<212> TYPE: DNA
<213> ORGANISM: Artificial Sequence
<220> FEATURE:
<223> OTHER INFORMATION: SAMi-hDKK1#189

<400> SEQUENCE: 189
agcgttgtta ctgtggaga 19

<210> SEQ ID NO 190
<211> LENGTH: 19
<212> TYPE: DNA
<213> ORGANISM: Artificial Sequence
<220> FEATURE:
<223> OTHER INFORMATION: SAMi-hDKK1#190

<400> SEQUENCE: 190
ggagaaggtc tgtcttgcc 19

<210> SEQ ID NO 191
<211> LENGTH: 19
<212> TYPE: DNA
<213> ORGANISM: Artificial Sequence
<220> FEATURE:
<223> OTHER INFORMATION: SAMi-hDKK1#191

<400> SEQUENCE: 191
gagaaggtct gtcttgccg 19

<210> SEQ ID NO 192
<211> LENGTH: 19
<212> TYPE: DNA
<213> ORGANISM: Artificial Sequence
<220> FEATURE:
<223> OTHER INFORMATION: SAMi-hDKK1#192

<400> SEQUENCE: 192
agaaggtctg tcttgccgg 19

<210> SEQ ID NO 193
<211> LENGTH: 19
<212> TYPE: DNA
<213> ORGANISM: Artificial Sequence
<220> FEATURE:
<223> OTHER INFORMATION: SAMi-hDKK1#193

<400> SEQUENCE: 193
gaaggtctgt cttgccgga 19

<210> SEQ ID NO 194
<211> LENGTH: 19
<212> TYPE: DNA
<213> ORGANISM: Artificial Sequence
<220> FEATURE:
<223> OTHER INFORMATION: SAMi-hDKK1#194

<400> SEQUENCE: 194
aaggtctgtc ttgccggat 19

<210> SEQ ID NO 195
<211> LENGTH: 19
<212> TYPE: DNA
<213> ORGANISM: Artificial Sequence
<220> FEATURE:
<223> OTHER INFORMATION: SAMi-hDKK1#195

<400> SEQUENCE: 195

-continued tctgtcttgc cggatacag 19

<210> SEQ ID NO 196
<211> LENGTH: 19
<212> TYPE: DNA
<213> ORGANISM: Artificial Sequence
<220> FEATURE:
<223> OTHER INFORMATION: SAMi-hDKK1#196

<400> SEQUENCE: 196
ctgtcttgcc ggatacaga 19

<210> SEQ ID NO 197
<211> LENGTH: 19
<212> TYPE: DNA
<213> ORGANISM: Artificial Sequence
<220> FEATURE:
<223> OTHER INFORMATION: SAMi-hDKK1#197

<400> SEQUENCE: 197
tgtcttgccg gatacagaa 19

<210> SEQ ID NO 198
<211> LENGTH: 19
<212> TYPE: DNA
<213> ORGANISM: Artificial Sequence
<220> FEATURE:
<223> OTHER INFORMATION: SAMi-hDKK1#198

<400> SEQUENCE: 198
gtcttgccgg atacagaaa 19

<210> SEQ ID NO 199
<211> LENGTH: 19
<212> TYPE: DNA
<213> ORGANISM: Artificial Sequence
<220> FEATURE:
<223> OTHER INFORMATION: SAMi-hDKK1#199

<400> SEQUENCE: 199
tcttgccgga tacagaaag 19

<210> SEQ ID NO 200
<211> LENGTH: 19
<212> TYPE: DNA
<213> ORGANISM: Artificial Sequence
<220> FEATURE:
<223> OTHER INFORMATION: SAMi-hDKK1#200

<400> SEQUENCE: 200
cttgccggat acagaaaga 19

<210> SEQ ID NO 201
<211> LENGTH: 19
<212> TYPE: DNA
<213> ORGANISM: Artificial Sequence
<220> FEATURE:
<223> OTHER INFORMATION: SAMi-hDKK1#201

<400> SEQUENCE: 201
ttgccggata cagaaagat 19

<210> SEQ ID NO 202
<211> LENGTH: 19
<212> TYPE: DNA
<213> ORGANISM: Artificial Sequence
<220> FEATURE:
<223> OTHER INFORMATION: SAMi-hDKK1#202

<400> SEQUENCE: 202
tgccggatac agaaagatc 19

<210> SEQ ID NO 203
<211> LENGTH: 19
<212> TYPE: DNA
<213> ORGANISM: Artificial Sequence
<220> FEATURE:
<223> OTHER INFORMATION: SAMi-hDKK1#203

<400> SEQUENCE: 203
gccggataca gaaagatca 19

<210> SEQ ID NO 204
<211> LENGTH: 19
<212> TYPE: DNA
<213> ORGANISM: Artificial Sequence
<220> FEATURE:
<223> OTHER INFORMATION: SAMi-hDKK1#204

<400> SEQUENCE: 204
cagaaagatc accatcaag 19

<210> SEQ ID NO 205
<211> LENGTH: 19
<212> TYPE: DNA
<213> ORGANISM: Artificial Sequence
<220> FEATURE:
<223> OTHER INFORMATION: SAMi-hDKK1#205

<400> SEQUENCE: 205
ccagtaattc ttctaggct 19

<210> SEQ ID NO 206
<211> LENGTH: 19
<212> TYPE: DNA
<213> ORGANISM: Artificial Sequence
<220> FEATURE:
<223> OTHER INFORMATION: SAMi-hDKK1#206

<400> SEQUENCE: 206
cagtaattct tctaggctt 19

<210> SEQ ID NO 207
<211> LENGTH: 19
<212> TYPE: DNA
<213> ORGANISM: Artificial Sequence
<220> FEATURE:
<223> OTHER INFORMATION: SAMi-hDKK1#207

<400> SEQUENCE: 207
attcttctag gcttcacac 19

<210> SEQ ID NO 208
<211> LENGTH: 19
<212> TYPE: DNA
<213> ORGANISM: Artificial Sequence
<220> FEATURE:
<223> OTHER INFORMATION: SAMi-hDKK1#208

<400> SEQUENCE: 208
agacactaaa ccagctatc 19

<210> SEQ ID NO 209
<211> LENGTH: 19
<212> TYPE: DNA
<213> ORGANISM: Artificial Sequence
<220> FEATURE:
<223> OTHER INFORMATION: SAMi-hDKK1#209

<400> SEQUENCE: 209
gcagtgaact ccttttata 19

<210> SEQ ID NO 210
<211> LENGTH: 19
<212> TYPE: DNA
<213> ORGANISM: Artificial Sequence
<220> FEATURE:
<223> OTHER INFORMATION: SAMi-hDKK1#210

<400> SEQUENCE: 210
cagtgaactc cttttatat 19

<210> SEQ ID NO 211
<211> LENGTH: 19
<212> TYPE: DNA
<213> ORGANISM: Artificial Sequence
<220> FEATURE:
<223> OTHER INFORMATION: SAMi-hDKK1#211

<400> SEQUENCE: 211
ccttcatcaa ctcaatcct 19

<210> SEQ ID NO 212
<211> LENGTH: 19
<212> TYPE: DNA
<213> ORGANISM: Artificial Sequence
<220> FEATURE:
<223> OTHER INFORMATION: SAMi-hDKK1#212

<400> SEQUENCE: 212
cttcatcaac tcaatccta 19

<210> SEQ ID NO 213
<211> LENGTH: 19
<212> TYPE: DNA
<213> ORGANISM: Artificial Sequence
<220> FEATURE:
<223> OTHER INFORMATION: SAMi-hDKK1#213

<400> SEQUENCE: 213
atcaactcaa tcctaagga 19

<210> SEQ ID NO 214
<211> LENGTH: 19
<212> TYPE: DNA
<213> ORGANISM: Artificial Sequence
<220> FEATURE:
<223> OTHER INFORMATION: SAMi-hDKK1#214

<400> SEQUENCE: 214
tcaactcaat cctaaggat 19

<210> SEQ ID NO 215
<211> LENGTH: 19
<212> TYPE: DNA
<213> ORGANISM: Artificial Sequence
<220> FEATURE:
<223> OTHER INFORMATION: SAMi-hDKK1#215

<400> SEQUENCE: 215
caactcaatc ctaaggata 19

<210> SEQ ID NO 216
<211> LENGTH: 19
<212> TYPE: DNA
<213> ORGANISM: Artificial Sequence
<220> FEATURE:
<223> OTHER INFORMATION: SAMi-hDKK1#216

<400> SEQUENCE: 216
aactcaatcc taaggatat 19

<210> SEQ ID NO 217
<211> LENGTH: 19
<212> TYPE: DNA
<213> ORGANISM: Artificial Sequence
<220> FEATURE:
<223> OTHER INFORMATION: SAMi-hDKK1#217

<400> SEQUENCE: 217
actcaatcct aaggatata 19

<210> SEQ ID NO 218
<211> LENGTH: 19
<212> TYPE: DNA
<213> ORGANISM: Artificial Sequence
<220> FEATURE:
<223> OTHER INFORMATION: SAMi-hDKK1#218

<400> SEQUENCE: 218
ctcaatccta aggatatac 19

<210> SEQ ID NO 219
<211> LENGTH: 19
<212> TYPE: DNA
<213> ORGANISM: Artificial Sequence
<220> FEATURE:
<223> OTHER INFORMATION: SAMi-hDKK1#219

<400> SEQUENCE: 219
gatatacaag ttctgtggt 19

<210> SEQ ID NO 220
<211> LENGTH: 19
<212> TYPE: DNA
<213> ORGANISM: Artificial Sequence
<220> FEATURE:
<223> OTHER INFORMATION: SAMi-hDKK1#220

<400> SEQUENCE: 220
gcattccaat aacaccttc 19

<210> SEQ ID NO 221
<211> LENGTH: 19
<212> TYPE: DNA
<213> ORGANISM: Artificial Sequence
<220> FEATURE:
<223> OTHER INFORMATION: SAMi-hDKK1#221

<400> SEQUENCE: 221
cattccaata acaccttcc 19

<210> SEQ ID NO 222

<211> LENGTH: 19
<212> TYPE: DNA
<213> ORGANISM: Artificial Sequence
<220> FEATURE:
<223> OTHER INFORMATION: SAMi-hDKK1#222

<400> SEQUENCE: 222
ggagtgtaag agctttgtt 19

<210> SEQ ID NO 223
<211> LENGTH: 19
<212> TYPE: DNA
<213> ORGANISM: Artificial Sequence
<220> FEATURE:
<223> OTHER INFORMATION: SAMi-hDKK1#223

<400> SEQUENCE: 223
gagtgtaaga gctttgttt 19

<210> SEQ ID NO 224
<211> LENGTH: 19
<212> TYPE: DNA
<213> ORGANISM: Artificial Sequence
<220> FEATURE:
<223> OTHER INFORMATION: SAMi-hDKK1#224

<400> SEQUENCE: 224
tttatggaac tcccctgtg 19

<210> SEQ ID NO 225
<211> LENGTH: 19
<212> TYPE: DNA
<213> ORGANISM: Artificial Sequence
<220> FEATURE:
<223> OTHER INFORMATION: SAMi-hDKK1#225

<400> SEQUENCE: 225
ttatggaact cccctgtga 19

<210> SEQ ID NO 226
<211> LENGTH: 19
<212> TYPE: DNA
<213> ORGANISM: Artificial Sequence
<220> FEATURE:
<223> OTHER INFORMATION: SAMi-hDKK1#226

<400> SEQUENCE: 226
gtgattgcag taaattact 19

<210> SEQ ID NO 227
<211> LENGTH: 19
<212> TYPE: DNA
<213> ORGANISM: Artificial Sequence
<220> FEATURE:
<223> OTHER INFORMATION: SAMi-hDKK1#227

<400> SEQUENCE: 227
tgattgcagt aaattactg 19

<210> SEQ ID NO 228
<211> LENGTH: 19
<212> TYPE: DNA
<213> ORGANISM: Artificial Sequence
<220> FEATURE:
<223> OTHER INFORMATION: SAMi-hDKK1#228

<400> SEQUENCE: 228
gattgcagta aattactgt 19

<210> SEQ ID NO 229
<211> LENGTH: 19
<212> TYPE: DNA
<213> ORGANISM: Artificial Sequence
<220> FEATURE:
<223> OTHER INFORMATION: SAMi-hDKK1#229

<400> SEQUENCE: 229
attgcagtaa attactgta 19

<210> SEQ ID NO 230
<211> LENGTH: 19
<212> TYPE: DNA
<213> ORGANISM: Artificial Sequence
<220> FEATURE:
<223> OTHER INFORMATION: SAMi-hDKK1#230

<400> SEQUENCE: 230
gtaaattctc agtgtggca 19

<210> SEQ ID NO 231
<211> LENGTH: 19
<212> TYPE: DNA
<213> ORGANISM: Artificial Sequence
<220> FEATURE:
<223> OTHER INFORMATION: SAMi-hDKK1#231

<400> SEQUENCE: 231
taaattctca gtgtggcac 19

<210> SEQ ID NO 232
<211> LENGTH: 19
<212> TYPE: DNA
<213> ORGANISM: Artificial Sequence
<220> FEATURE:
<223> OTHER INFORMATION: SAMi-hDKK1#232

<400> SEQUENCE: 232
aaattctcag tgtggcact 19

<210> SEQ ID NO 233
<211> LENGTH: 19
<212> TYPE: DNA
<213> ORGANISM: Artificial Sequence
<220> FEATURE:
<223> OTHER INFORMATION: SAMi-hDKK1#233

<400> SEQUENCE: 233
tggcacttac ctgtaaatg 19

<210> SEQ ID NO 234
<211> LENGTH: 19
<212> TYPE: DNA
<213> ORGANISM: Artificial Sequence
<220> FEATURE:
<223> OTHER INFORMATION: SAMi-hDKK1#234

<400> SEQUENCE: 234
ggcacttacc tgtaaatgc 19

<210> SEQ ID NO 235
<211> LENGTH: 19
<212> TYPE: DNA

<213> ORGANISM: Artificial Sequence
<220> FEATURE:
<223> OTHER INFORMATION: SAMi-hDKK1#235

<400> SEQUENCE: 235
gcacttacct gtaaatgca 19

<210> SEQ ID NO 236
<211> LENGTH: 19
<212> TYPE: DNA
<213> ORGANISM: Artificial Sequence
<220> FEATURE:
<223> OTHER INFORMATION: SAMi-hDKK1#236

<400> SEQUENCE: 236
cacttacctg taaatgcaa 19

<210> SEQ ID NO 237
<211> LENGTH: 19
<212> TYPE: DNA
<213> ORGANISM: Artificial Sequence
<220> FEATURE:
<223> OTHER INFORMATION: SAMi-hDKK1#237

<400> SEQUENCE: 237
ggtgctgcac tgcctattt 19

<210> SEQ ID NO 238
<211> LENGTH: 19
<212> TYPE: DNA
<213> ORGANISM: Artificial Sequence
<220> FEATURE:
<223> OTHER INFORMATION: SAMi-hDKK1#238

<400> SEQUENCE: 238
gtgctgcact gcctatttt 19

<210> SEQ ID NO 239
<211> LENGTH: 19
<212> TYPE: DNA
<213> ORGANISM: Artificial Sequence
<220> FEATURE:
<223> OTHER INFORMATION: SAMi-hDKK1#239

<400> SEQUENCE: 239
tgtacacatt gattgttat 19

<210> SEQ ID NO 240
<211> LENGTH: 19
<212> TYPE: DNA
<213> ORGANISM: Artificial Sequence
<220> FEATURE:
<223> OTHER INFORMATION: SAMi-hDKK1#240

<400> SEQUENCE: 240
gtacacattg attgttatc 19

<210> SEQ ID NO 241
<211> LENGTH: 19
<212> TYPE: DNA
<213> ORGANISM: Artificial Sequence
<220> FEATURE:
<223> OTHER INFORMATION: SAMi-hDKK1#241

<400> SEQUENCE: 241
tacacattga ttgttatct 19

<210> SEQ ID NO 242
<211> LENGTH: 19
<212> TYPE: DNA
<213> ORGANISM: Artificial Sequence
<220> FEATURE:
<223> OTHER INFORMATION: SAMi-hDKK1#242

<400> SEQUENCE: 242
cattgattgt tatcttgac 19

<210> SEQ ID NO 243
<211> LENGTH: 19
<212> TYPE: DNA
<213> ORGANISM: Artificial Sequence
<220> FEATURE:
<223> OTHER INFORMATION: SAMi-hDKK1#243

<400> SEQUENCE: 243
attgttatct tgactgaca 19

<210> SEQ ID NO 244
<211> LENGTH: 19
<212> TYPE: DNA
<213> ORGANISM: Artificial Sequence
<220> FEATURE:
<223> OTHER INFORMATION: SAMi-hDKK1#244

<400> SEQUENCE: 244
tatcttgact gacaaatat 19

<210> SEQ ID NO 245
<211> LENGTH: 19
<212> TYPE: DNA
<213> ORGANISM: Artificial Sequence
<220> FEATURE:
<223> OTHER INFORMATION: SAMi-hDKK1#245

<400> SEQUENCE: 245
catttcagct tatagttct 19

<210> SEQ ID NO 246
<211> LENGTH: 19
<212> TYPE: DNA
<213> ORGANISM: Artificial Sequence
<220> FEATURE:
<223> OTHER INFORMATION: SAMi-hDKK1#246

<400> SEQUENCE: 246
aagcataacc ctttacccc 19

<210> SEQ ID NO 247
<211> LENGTH: 19
<212> TYPE: DNA
<213> ORGANISM: Artificial Sequence
<220> FEATURE:
<223> OTHER INFORMATION: SAMi-hDKK1#247

<400> SEQUENCE: 247
agcataaccc tttacccca 19

<210> SEQ ID NO 248
<211> LENGTH: 19
<212> TYPE: DNA
<213> ORGANISM: Artificial Sequence
<220> FEATURE:

<223> OTHER INFORMATION: SAMi-hDKK1#248

<400> SEQUENCE: 248
gcataaccct ttaccccat 19

<210> SEQ ID NO 249
<211> LENGTH: 19
<212> TYPE: DNA
<213> ORGANISM: Artificial Sequence
<220> FEATURE:
<223> OTHER INFORMATION: SAMi-hDKK1#249

<400> SEQUENCE: 249
cataaccctt taccccatt 19

<210> SEQ ID NO 250
<211> LENGTH: 19
<212> TYPE: DNA
<213> ORGANISM: Artificial Sequence
<220> FEATURE:
<223> OTHER INFORMATION: SAMi-hDKK1#250

<400> SEQUENCE: 250
accctttacc ccatttaat 19

<210> SEQ ID NO 251
<211> LENGTH: 19
<212> TYPE: DNA
<213> ORGANISM: Artificial Sequence
<220> FEATURE:
<223> OTHER INFORMATION: SAMi-hDKK1#251

<400> SEQUENCE: 251
ccatttaatt ctagagtct 19

<210> SEQ ID NO 252
<211> LENGTH: 19
<212> TYPE: DNA
<213> ORGANISM: Artificial Sequence
<220> FEATURE:
<223> OTHER INFORMATION: SAMi-hDKK1#252

<400> SEQUENCE: 252
catttaattc tagagtcta 19

<210> SEQ ID NO 253
<211> LENGTH: 19
<212> TYPE: DNA
<213> ORGANISM: Artificial Sequence
<220> FEATURE:
<223> OTHER INFORMATION: SAMi-hDKK1#253

<400> SEQUENCE: 253
atttaattct agagtctag 19

<210> SEQ ID NO 254
<211> LENGTH: 19
<212> TYPE: DNA
<213> ORGANISM: Artificial Sequence
<220> FEATURE:
<223> OTHER INFORMATION: SAMi-hDKK1#254

<400> SEQUENCE: 254
ttctagagtc tagaacgca 19

<210> SEQ ID NO 255
<211> LENGTH: 19
<212> TYPE: DNA
<213> ORGANISM: Artificial Sequence
<220> FEATURE:
<223> OTHER INFORMATION: SAMi-hDKK1#255

<400> SEQUENCE: 255
tctagagtct agaacgcaa 19

<210> SEQ ID NO 256
<211> LENGTH: 19
<212> TYPE: DNA
<213> ORGANISM: Artificial Sequence
<220> FEATURE:
<223> OTHER INFORMATION: SAMi-hDKK1#256

<400> SEQUENCE: 256
ctagagtcta gaacgcaag 19

<210> SEQ ID NO 257
<211> LENGTH: 19
<212> TYPE: DNA
<213> ORGANISM: Artificial Sequence
<220> FEATURE:
<223> OTHER INFORMATION: SAMi-hDKK1#257

<400> SEQUENCE: 257
tagagtctag aacgcaagg 19

<210> SEQ ID NO 258
<211> LENGTH: 19
<212> TYPE: DNA
<213> ORGANISM: Artificial Sequence
<220> FEATURE:
<223> OTHER INFORMATION: SAMi-hDKK1#258

<400> SEQUENCE: 258
agagtctaga acgcaagga 19

<210> SEQ ID NO 259
<211> LENGTH: 19
<212> TYPE: DNA
<213> ORGANISM: Artificial Sequence
<220> FEATURE:
<223> OTHER INFORMATION: SAMi-hDKK1#259

<400> SEQUENCE: 259
gagtctagaa cgcaaggat 19

<210> SEQ ID NO 260
<211> LENGTH: 19
<212> TYPE: DNA
<213> ORGANISM: Artificial Sequence
<220> FEATURE:
<223> OTHER INFORMATION: SAMi-hDKK1#260

<400> SEQUENCE: 260
caaggatctc ttggaatga 19

<210> SEQ ID NO 261
<211> LENGTH: 19
<212> TYPE: DNA
<213> ORGANISM: Artificial Sequence
<220> FEATURE:
<223> OTHER INFORMATION: SAMi-hDKK1#261

<400> SEQUENCE: 261
tggaatgaca aatgatagg 19

<210> SEQ ID NO 262
<211> LENGTH: 19
<212> TYPE: DNA
<213> ORGANISM: Artificial Sequence
<220> FEATURE:
<223> OTHER INFORMATION: SAMi-hDKK1#262

<400> SEQUENCE: 262
taggtaccta aaatgtaac 19

<210> SEQ ID NO 263
<211> LENGTH: 19
<212> TYPE: DNA
<213> ORGANISM: Artificial Sequence
<220> FEATURE:
<223> OTHER INFORMATION: SAMi-hDKK1#263

<400> SEQUENCE: 263
aggtacctaa aatgtaaca 19

<210> SEQ ID NO 264
<211> LENGTH: 19
<212> TYPE: DNA
<213> ORGANISM: Artificial Sequence
<220> FEATURE:
<223> OTHER INFORMATION: SAMi-hDKK1#264

<400> SEQUENCE: 264
ggtacctaaa atgtaacat 19

<210> SEQ ID NO 265
<211> LENGTH: 19
<212> TYPE: DNA
<213> ORGANISM: Artificial Sequence
<220> FEATURE:
<223> OTHER INFORMATION: SAMi-hDKK1#265

<400> SEQUENCE: 265
aatactagct tattttctg 19

<210> SEQ ID NO 266
<211> LENGTH: 19
<212> TYPE: DNA
<213> ORGANISM: Artificial Sequence
<220> FEATURE:
<223> OTHER INFORMATION: SAMi-hDKK1#266

<400> SEQUENCE: 266
atactagctt attttctga 19

<210> SEQ ID NO 267
<211> LENGTH: 19
<212> TYPE: DNA
<213> ORGANISM: Artificial Sequence
<220> FEATURE:
<223> OTHER INFORMATION: SAMi-hDKK1#267

<400> SEQUENCE: 267
ctgaaatgta ctatcttaa 19

<210> SEQ ID NO 268
<211> LENGTH: 19

<212> TYPE: DNA
<213> ORGANISM: Artificial Sequence
<220> FEATURE:
<223> OTHER INFORMATION: SAMi-hDKK1#268

<400> SEQUENCE: 268
aatgtactat cttaatgct 19

<210> SEQ ID NO 269
<211> LENGTH: 19
<212> TYPE: DNA
<213> ORGANISM: Artificial Sequence
<220> FEATURE:
<223> OTHER INFORMATION: SAMi-hDKK1#269

<400> SEQUENCE: 269
atgtactatc ttaatgctt 19

<210> SEQ ID NO 270
<211> LENGTH: 19
<212> TYPE: DNA
<213> ORGANISM: Artificial Sequence
<220> FEATURE:
<223> OTHER INFORMATION: SAMi-hDKK1#270

<400> SEQUENCE: 270
tgtactatct taatgctta 19

<210> SEQ ID NO 271
<211> LENGTH: 19
<212> TYPE: DNA
<213> ORGANISM: Artificial Sequence
<220> FEATURE:
<223> OTHER INFORMATION: SAMi-hDKK1#271

<400> SEQUENCE: 271
ttaggctgtg atagttttt 19

<210> SEQ ID NO 272
<211> LENGTH: 19
<212> TYPE: DNA
<213> ORGANISM: Artificial Sequence
<220> FEATURE:
<223> OTHER INFORMATION: SAMi-hDKK1#272

<400> SEQUENCE: 272
taggctgtga tagtttttg 19

<210> SEQ ID NO 273
<211> LENGTH: 19
<212> TYPE: DNA
<213> ORGANISM: Artificial Sequence
<220> FEATURE:
<223> OTHER INFORMATION: SAMi-hDKK1#273

<400> SEQUENCE: 273
aaatgttata agtagacat 19

<210> SEQ ID NO 274
<211> LENGTH: 19
<212> TYPE: DNA
<213> ORGANISM: Artificial Sequence
<220> FEATURE:
<223> OTHER INFORMATION: SAMi-hDKK1#274

<400> SEQUENCE: 274
aatgttataa gtagacata 19

<210> SEQ ID NO 275
<211> LENGTH: 19
<212> TYPE: DNA
<213> ORGANISM: Artificial Sequence
<220> FEATURE:
<223> OTHER INFORMATION: SAMi-hDKK1#275

<400> SEQUENCE: 275
atgttataag tagacatac 19

<210> SEQ ID NO 276
<211> LENGTH: 19
<212> TYPE: DNA
<213> ORGANISM: Artificial Sequence
<220> FEATURE:
<223> OTHER INFORMATION: SAMi-hDKK1#276

<400> SEQUENCE: 276
tgtgatctta gaggtttgt 19

<210> SEQ ID NO 277
<211> LENGTH: 19
<212> TYPE: DNA
<213> ORGANISM: Artificial Sequence
<220> FEATURE:
<223> OTHER INFORMATION: SAMi-hDKK1#277

<400> SEQUENCE: 277
gtgatcttag aggtttgtg 19

<210> SEQ ID NO 278
<211> LENGTH: 19
<212> TYPE: DNA
<213> ORGANISM: Artificial Sequence
<220> FEATURE:
<223> OTHER INFORMATION: SAMi-hDKK1#278

<400> SEQUENCE: 278
tgatcttaga ggtttgtgt 19

<210> SEQ ID NO 279
<211> LENGTH: 19
<212> TYPE: DNA
<213> ORGANISM: Artificial Sequence
<220> FEATURE:
<223> OTHER INFORMATION: SAMi-hDKK1#279

<400> SEQUENCE: 279
gatcttagag gtttgtgtg 19

<210> SEQ ID NO 280
<211> LENGTH: 19
<212> TYPE: DNA
<213> ORGANISM: Artificial Sequence
<220> FEATURE:
<223> OTHER INFORMATION: SAMi-hDKK1#280

<400> SEQUENCE: 280
gtgtgttcta caagaacgg 19

<210> SEQ ID NO 281
<211> LENGTH: 19
<212> TYPE: DNA
<213> ORGANISM: Artificial Sequence
<220> FEATURE:
<223> OTHER INFORMATION: SAMi-hDKK1#281

<400> SEQUENCE: 281
tgtgttctac aagaacgga 19

<210> SEQ ID NO 282
<211> LENGTH: 19
<212> TYPE: DNA
<213> ORGANISM: Artificial Sequence
<220> FEATURE:
<223> OTHER INFORMATION: SAMi-hDKK1#282

<400> SEQUENCE: 282
ttctacaaga acggaagtg 19

<210> SEQ ID NO 283
<211> LENGTH: 19
<212> TYPE: DNA
<213> ORGANISM: Artificial Sequence
<220> FEATURE:
<223> OTHER INFORMATION: SAMi-hDKK1#283

<400> SEQUENCE: 283
tctacaagaa cggaagtgt 19

<210> SEQ ID NO 284
<211> LENGTH: 19
<212> TYPE: DNA
<213> ORGANISM: Artificial Sequence
<220> FEATURE:
<223> OTHER INFORMATION: SAMi-hDKK1#284

<400> SEQUENCE: 284
aacggaagtg tgatatgtt 19

<210> SEQ ID NO 285
<211> LENGTH: 19
<212> TYPE: DNA
<213> ORGANISM: Artificial Sequence
<220> FEATURE:
<223> OTHER INFORMATION: SAMi-hDKK1#285

<400> SEQUENCE: 285
acggaagtgt gatatgttt 19

<210> SEQ ID NO 286
<211> LENGTH: 19
<212> TYPE: DNA
<213> ORGANISM: Artificial Sequence
<220> FEATURE:
<223> OTHER INFORMATION: SAMi-hDKK1#286

<400> SEQUENCE: 286
cagtgtctaa atataagac 19

<210> SEQ ID NO 287
<211> LENGTH: 19
<212> TYPE: DNA
<213> ORGANISM: Artificial Sequence
<220> FEATURE:
<223> OTHER INFORMATION: SAMi-hDKK1#287

<400> SEQUENCE: 287
ataagacaat attgatcag 19

<210> SEQ ID NO 288
<211> LENGTH: 19
<212> TYPE: DNA
<213> ORGANISM: Artificial Sequence
<220> FEATURE:
<223> OTHER INFORMATION: SAMi-hDKK1#288

<400> SEQUENCE: 288
taagacaata ttgatcagc 19

<210> SEQ ID NO 289
<211> LENGTH: 19
<212> TYPE: DNA
<213> ORGANISM: Artificial Sequence
<220> FEATURE:
<223> OTHER INFORMATION: SAMi-hDKK1#289

<400> SEQUENCE: 289
aagacaatat tgatcagct 19

<210> SEQ ID NO 290
<211> LENGTH: 19
<212> TYPE: DNA
<213> ORGANISM: Artificial Sequence
<220> FEATURE:
<223> OTHER INFORMATION: SAMi-hDKK1#290

<400> SEQUENCE: 290
attgatcagc tctagaata 19

<210> SEQ ID NO 291
<211> LENGTH: 19
<212> TYPE: DNA
<213> ORGANISM: Artificial Sequence
<220> FEATURE:
<223> OTHER INFORMATION: SAMi-hDKK1#291

<400> SEQUENCE: 291
ttgatcagct ctagaataa 19

<210> SEQ ID NO 292
<211> LENGTH: 19
<212> TYPE: DNA
<213> ORGANISM: Artificial Sequence
<220> FEATURE:
<223> OTHER INFORMATION: SAMi-hDKK1#292

<400> SEQUENCE: 292
tgatcagctc tagaataac 19

<210> SEQ ID NO 293
<211> LENGTH: 19
<212> TYPE: DNA
<213> ORGANISM: Artificial Sequence
<220> FEATURE:
<223> OTHER INFORMATION: SAMi-hDKK1#293

<400> SEQUENCE: 293
agctctagaa taactttaa 19

<210> SEQ ID NO 294
<211> LENGTH: 19
<212> TYPE: DNA
<213> ORGANISM: Artificial Sequence
<220> FEATURE:
<223> OTHER INFORMATION: SAMi-hDKK1#294

<400> SEQUENCE: 294
tctgcattga taaactcaa 19

<210> SEQ ID NO 295
<211> LENGTH: 19
<212> TYPE: DNA
<213> ORGANISM: Artificial Sequence
<220> FEATURE:
<223> OTHER INFORMATION: SAMi-hDKK1#295

<400> SEQUENCE: 295
ctgcattgat aaactcaaa 19

<210> SEQ ID NO 296
<211> LENGTH: 19
<212> TYPE: DNA
<213> ORGANISM: Artificial Sequence
<220> FEATURE:
<223> OTHER INFORMATION: SAMi-hDKK1#296

<400> SEQUENCE: 296
tgcattgata aactcaaat 19

<210> SEQ ID NO 297
<211> LENGTH: 19
<212> TYPE: DNA
<213> ORGANISM: Artificial Sequence
<220> FEATURE:
<223> OTHER INFORMATION: SAMi-hDKK1#297

<400> SEQUENCE: 297
aaactcaaat gatcatggc 19

<210> SEQ ID NO 298
<211> LENGTH: 19
<212> TYPE: DNA
<213> ORGANISM: Artificial Sequence
<220> FEATURE:
<223> OTHER INFORMATION: SAMi-hDKK1#298

<400> SEQUENCE: 298
aactcaaatg atcatggca 19

<210> SEQ ID NO 299
<211> LENGTH: 19
<212> TYPE: DNA
<213> ORGANISM: Artificial Sequence
<220> FEATURE:
<223> OTHER INFORMATION: SAMi-hDKK1#299

<400> SEQUENCE: 299
atgagagtga atcttacat 19

<210> SEQ ID NO 300
<211> LENGTH: 19
<212> TYPE: DNA
<213> ORGANISM: Artificial Sequence
<220> FEATURE:
<223> OTHER INFORMATION: SAMi-hDKK1#300

<400> SEQUENCE: 300
tgagagtgaa tcttacatt 19

<210> SEQ ID NO 301

<211> LENGTH: 19
<212> TYPE: DNA
<213> ORGANISM: Artificial Sequence
<220> FEATURE:
<223> OTHER INFORMATION: SAMi-hDKK1#301

<400> SEQUENCE: 301
gagagtgaat cttacatta 19

<210> SEQ ID NO 302
<211> LENGTH: 19
<212> TYPE: DNA
<213> ORGANISM: Artificial Sequence
<220> FEATURE:
<223> OTHER INFORMATION: SAMi-hDKK1#302

<400> SEQUENCE: 302
agagtgaatc ttacattac 19

<210> SEQ ID NO 303
<211> LENGTH: 19
<212> TYPE: DNA
<213> ORGANISM: Artificial Sequence
<220> FEATURE:
<223> OTHER INFORMATION: SAMi-hDKK1#303

<400> SEQUENCE: 303
gagtgaatct tacattact 19

<210> SEQ ID NO 304
<211> LENGTH: 19
<212> TYPE: DNA
<213> ORGANISM: Artificial Sequence
<220> FEATURE:
<223> OTHER INFORMATION: SAMi-hDKK1#304

<400> SEQUENCE: 304
tcttacatta ctactttca 19

<210> SEQ ID NO 305
<211> LENGTH: 19
<212> TYPE: DNA
<213> ORGANISM: Artificial Sequence
<220> FEATURE:
<223> OTHER INFORMATION: SAMi-hDKK1#305

<400> SEQUENCE: 305
cttacattac tactttcaa 19

<210> SEQ ID NO 306
<211> LENGTH: 19
<212> TYPE: DNA
<213> ORGANISM: Artificial Sequence
<220> FEATURE:
<223> OTHER INFORMATION: SAMi-DKK1 patent#1

<400> SEQUENCE: 306
cactaaacca gctatccaa 19

<210> SEQ ID NO 307
<211> LENGTH: 19
<212> TYPE: DNA
<213> ORGANISM: Artificial Sequence
<220> FEATURE:
<223> OTHER INFORMATION: SAMi-DKK1 patent#2

<400> SEQUENCE: 307
ggtaatgatc atagcacct 19

<210> SEQ ID NO 308
<211> LENGTH: 19
<212> TYPE: DNA
<213> ORGANISM: Artificial Sequence
<220> FEATURE:
<223> OTHER INFORMATION: SAMi-DKK1 patent#3

<400> SEQUENCE: 308
gaataagtac cagaccatt 19

<210> SEQ ID NO 309
<211> LENGTH: 19
<212> TYPE: DNA
<213> ORGANISM: Artificial Sequence
<220> FEATURE:
<223> OTHER INFORMATION: SAMi-DKK1 patent#4

<400> SEQUENCE: 309
aggtctgtct tgccggata 19

<210> SEQ ID NO 310
<211> LENGTH: 20
<212> TYPE: DNA
<213> ORGANISM: Artificial Sequence
<220> FEATURE:
<223> OTHER INFORMATION: DKK1-f

<400> SEQUENCE: 310
tgacaactac cagccgtacc 20

<210> SEQ ID NO 311
<211> LENGTH: 20
<212> TYPE: DNA
<213> ORGANISM: Artificial Sequence
<220> FEATURE:
<223> OTHER INFORMATION: DKK1-r

<400> SEQUENCE: 311
caggcgagac agatttgcac 20

<210> SEQ ID NO 312
<211> LENGTH: 20
<212> TYPE: DNA
<213> ORGANISM: Artificial Sequence
<220> FEATURE:
<223> OTHER INFORMATION: RPL13A-f

<400> SEQUENCE: 312
gtgtttgacg gcatcccacc 20

<210> SEQ ID NO 313
<211> LENGTH: 20
<212> TYPE: DNA
<213> ORGANISM: Artificial Sequence
<220> FEATURE:
<223> OTHER INFORMATION: RPL13A-r

<400> SEQUENCE: 313
taggcttcag acgcacgacc 20

<210> SEQ ID NO 314
<211> LENGTH: 101
<212> TYPE: DNA

<213> ORGANISM: Artificial Sequence
<220> FEATURE:
<223> OTHER INFORMATION: Synthetic construct

<400> SEQUENCE: 314
gtggcggtgg cggcgcagag ctctgtgctc cctgcagtca ggactctggg accgcagggg 60
gctcccggac cctgactctg cagccgaacc ggcacggttt c 101

<210> SEQ ID NO 315
<211> LENGTH: 19
<212> TYPE: DNA
<213> ORGANISM: Artificial Sequence
<220> FEATURE:
<223> OTHER INFORMATION: Synthetic construct

<400> SEQUENCE: 315
tcaggactct gggaccgca 19

<210> SEQ ID NO 316
<211> LENGTH: 19
<212> TYPE: DNA
<213> ORGANISM: Artificial Sequence
<220> FEATURE:
<223> OTHER INFORMATION: Synthetic construct

<400> SEQUENCE: 316
caggactctg ggaccgcag 19

<210> SEQ ID NO 317
<211> LENGTH: 19
<212> TYPE: DNA
<213> ORGANISM: Artificial Sequence
<220> FEATURE:
<223> OTHER INFORMATION: Synthetic construct

<400> SEQUENCE: 317
aggactctgg gaccgcagg 19

<210> SEQ ID NO 318
<211> LENGTH: 19
<212> TYPE: DNA
<213> ORGANISM: Artificial Sequence
<220> FEATURE:
<223> OTHER INFORMATION: Synthetic construct

<400> SEQUENCE: 318
ggactctggg accgcaggg 19

<210> SEQ ID NO 319
<211> LENGTH: 19
<212> TYPE: DNA
<213> ORGANISM: Artificial Sequence
<220> FEATURE:
<223> OTHER INFORMATION: Synthetic construct

<400> SEQUENCE: 319
gactctggga ccgcagggg 19

<210> SEQ ID NO 320
<211> LENGTH: 19
<212> TYPE: DNA
<213> ORGANISM: Artificial Sequence
<220> FEATURE:
<223> OTHER INFORMATION: Synthetic construct

<400> SEQUENCE: 320

-continued

```
actctgggac cgcagggggg                                                   19


<210> SEQ ID NO 321
<211> LENGTH: 19
<212> TYPE: DNA
<213> ORGANISM: Artificial Sequence
<220> FEATURE:
<223> OTHER INFORMATION: Synthetic constant

<400> SEQUENCE: 321

ctctgggacc gcagggggc                                                    19


<210> SEQ ID NO 322
<211> LENGTH: 19
<212> TYPE: DNA
<213> ORGANISM: Artificial Sequence
<220> FEATURE:
<223> OTHER INFORMATION: Synthetic construct

<400> SEQUENCE: 322

tctgggaccg cagggggct                                                    19


<210> SEQ ID NO 323
<211> LENGTH: 19
<212> TYPE: DNA
<213> ORGANISM: Artificial Sequence
<220> FEATURE:
<223> OTHER INFORMATION: Synthetic construct

<400> SEQUENCE: 323

ctgggaccgc agggggctc                                                    19


<210> SEQ ID NO 324
<211> LENGTH: 19
<212> TYPE: DNA
<213> ORGANISM: Artificial Sequence
<220> FEATURE:
<223> OTHER INFORMATION: Synthetic construct

<400> SEQUENCE: 324

tgggaccgca gggggctcc                                                    19


<210> SEQ ID NO 325
<211> LENGTH: 19
<212> TYPE: DNA
<213> ORGANISM: Artificial Sequence
<220> FEATURE:
<223> OTHER INFORMATION: Synthetic construct

<400> SEQUENCE: 325

gggaccgcag ggggctccc                                                    19
```

DOUBLE-STRANDED OLIGONUCLEOTIDE TARGETING DKK1 GENE, CONSTRUCT INCLUDING SAME, AND HAIR LOSS PREVENTION OR HAIR GROWTH COMPOSITION CONTAINING SAME

CROSS-REFERENCE TO RELATED APPLICATIONS

This is a U.S. national phase under 35 USC § 371 of International Patent Application No. PCT/KR20/00750 filed Jan. 15, 2020, which in turn claims priority under 35 USC § 119 of Korean Patent Application No. 10-2019-0005277 filed Jan. 15, 2019. The disclosures of all such applications are hereby incorporated herein by reference in their respective entireties, for all purposes.

REFERENCE TO SEQUENCE LISTING SUBMITTED VIA PATENT CENTER

This application includes an electronically submitted sequence listing in .txt format. The .txt file contains a sequence listing entitled "570_UpdatedSeqListing_ST25.txt" created on Jul. 27, 2025 and is 61,747 bytes in size. The sequence listing contained in this .txt file is part of the specification and is hereby incorporated by reference herein in its entirety.

TECHNICAL FIELD

The present invention relates to a double-stranded oligonucleotide targeting a DKK1 gene, a construct including the same, nanoparticles including the oligonucleotide or construct, and the use thereof for preventing hair loss or promoting hair growth, and specifically to a DKK1-specific double-stranded oligonucleotide, a double-stranded oligonucleotide construct having a structure in which a hydrophilic substance and a hydrophobic substance are bound to both ends of the double-stranded oligonucleotide through a simple covalent bond or a linker-mediated covalent bond to efficiently deliver the oligonucleotide into cells, nanoparticles that can be produced through self-assembly of the double-stranded oligonucleotide constructs in an aqueous solution via hydrophobic interaction, and a composition for preventing hair loss and promoting hair growth containing the oligonucleotide, construct and/or nanoparticles.

BACKGROUND ART

Hair plays an important role in creating an individual identity and image, and has functions of blocking UV and protecting the scalp in addition to the above aesthetic functions. Hair loss (alopecia) is a disease in which body hair is abnormally reduced, and is not directly related to life, but is often accompanied by serious psychological distress with regard to appearance. Thus, severe hair loss may have very negative effects on the quality of life (Passchier J. et al., *Dermatology,* 197:217, 1998; McDonagh, A. J. and Messenger, A. G., *Dermatol Clin.,* 14:661, 1996). The incidence of alopecia, which is conventionally considered a genetic disease affecting men, has recently risen in women as well as in men due to external factors such as work-related stress, environmental pollution, exposure to harmful environments, and unhealthy eating habits, and thus the demand for prophylactic or therapeutic agents for alopecia is increasing. Alopecia is classified into scarring alopecia, in which hair follicles are destroyed and restored to fibrous tissue to make hair loss permanent, and non-scarring alopecia, in which the hair follicles are preserved without being converted to fibrous tissue. Non-scarring alopecia includes telogen effluvium, hereditary androgenetic alopecia, alopecia areata, and anagen effluvium (Jand I W et al., *J. Korean Med. Ophthal. Otol. Dermatol.* 2015).

Hair growth follows a cycle, also called a "hair cycle", including a growing stage, a degenerating stage, a resting stage, and an exogen stage. The growing stage is usually 2-8 years long, accounting for about 90% of the total hair cycle, and hair mother cells are continuously divided in the lower part of the hair bulb, which is in contact with follicular papilla, to produce hair. The degenerating stage is a stage during which hair growth stops for a while after the growing stage. The degenerating stage is a period of transition to the resting stage, when production and growth of hair stop. Hair growth stops due to changes in the hair roots, inactivation of hair mother cells and pigment cells and thus failure of keratin production. In the resting phase, the hair bulb contracts. Hair only falls out starting at the exogen stage, which is known to be mediated by a protease (Kim Eun-Hwa et al., *Journal of the Korean Society of Skin and Beauty*, Vol. 5, No. 2, 45; Naito et al., *Br. J. Dermatol.* 159:300-305, 2008). Factors regulating hair growth, such as androgens, estrogen, thyroid hormones, steroids, prolactin, and growth hormones, are considered to be involved in hair growth. Among them, androgens are known to be the most potent regulators. The most common example showing that hormones are involved in hair loss is temporary hair loss after childbirth. During pregnancy, the amount of estrogen increases and thus progression of the hair cycle from the growing stage to the resting stage is suppressed. After childbirth, the amount of estrogen rapidly decreases and progression to the resting stage is accelerated, resulting in hair loss during the resting stage. In other words, alopecia depends on hormones. However, other causes of hair loss include genetic factors, male hormones, aging, blood circulatory disorders, stress, superoxide radicals, and the like, and countermeasures may vary depending on these causes. DHT blockers are used as therapeutic agents for hair loss caused by male hormones, and these blockers are based on the basic mechanism by which conversion of testosterone to highly active dihydrotestosterone (hereinafter referred to as "DHT") is inhibited by 5-α-reductase. Meanwhile, DHT is able to bind with androgen receptor (AR) more than 5 times as strongly as testosterone, so substances that block the binding to the androgen receptor by delaying protein synthesis in hair follicles to prevent overproduction of DHT are used as therapeutic agents (Dallob A. L. et al., *J. Clin. Endocrinol. Metab.* 79:703-709, 1994; Ellsworth, K. and Harris G., *Biochem. Biophys. Res. Commun.* 215:774-780, 1995; Kaufman K. D., *Mol. and Cell. Endocrinology.* 198: 85-59, 2002).

Therapeutic agents for hair loss developed to date are mainly single compounds, examples of which include finasteride, targeting 5-alpha reductase to suppress overproduction of DHT, minoxidil for promoting blood circulation, and JAK inhibitors (ruxolitinib, tofacitinib), which have been recently approved by the US FDA, are sold as anticancer drugs, and have been found to have the effect of promoting hair growth. However, research with the goal of finding a substance that is more effective than the above substances is ongoing.

Dickkopf 1 (DKK1) is the most upregulated hair loss gene in androgenic alopecia, and the expression thereof is induced in dermal papilla cells at the hair loss site by DHT, which is known to be the main cause of hair loss. It is known that when DKK1 is strongly expressed, it interferes with the growth of hair follicles and promotes progression to the hair degenerating stage by inducing apoptosis of the outer root sheath, which directly envelops and protects the hair, and transports the same to the epidermis (Kwack et al., *J. Invest. Dermatol.* 132(6):1554-60. 2012). This is based on the Wnt antagonism of DKK1, which inhibits the low-density lipoprotein-receptor-related protein (LRP)-5/6 co-receptor required for Wnt/Bsignaling, which plays a key role in maintaining the hair growing stage. Interest in hair loss treatment targeting DKK1 has increased since DKK1 was found to greatly affect the progression of hair cells from the growing stage to the degenerating stage.

Technologies that suppress gene expression are an important means in the development of drugs for treating diseases and validating targets. Among such technologies, RNA interference (RNAi) has been found to act on sequence-specific mRNA in various types of mammalian cells since the role thereof was discovered (Barik, *J Mol Med* 83:764-773, 2005). When the long-chain RNA double-strand is delivered to cells, the delivered RNA double-strand is converted into small interfering RNA (siRNA) processed to 21 to 23 base pairs (bp) by an endonuclease called a "dicer", and siRNA binds to an RISC (RNA-induced silencing complex) and inhibits the expression of a target gene in a sequence-specific manner through a process whereby the guide (antisense) strand recognizes and degrades the target mRNA (Opalinska et al., *Nature Reviews Drug Discovery.* 1:503-514, 2002).

Bertrand's research team discovered that siRNA for the same target gene has a superior inhibitory effect on mRNA expression in vitro and in vivo compared to antisense oligonucleotide (ASO), and that the effect lasts for a long time (*Biochem. Biophys. Res. Commun.* 296:1000-1004, 2002). In addition, siRNA has a mechanism for binding complementarily to the target mRNA and regulating the expression of the target gene in a sequence-specific manner, and thus is widely applicable compared to conventional antibody-based drugs or chemical drugs (small molecule drugs) (Behlke, *MOLECULAR THERAPY.* 13(4):664-670, 2006).

Despite the excellent effects and wide application range of siRNA, siRNA must be effectively delivered to target cells by improving the in-vivo stability and cell delivery efficiency of siRNA in order for the siRNA to be developed into a therapeutic agent (Xie et al., Drug Discov. Today. 11(1-2):67-73, 2006).

In an attempt to solve this problem, research is being actively conducted on modification of some nucleotides or backbones of siRNA to impart nuclease resistance thereto in order to improve in-vivo stability and on the use of carriers such as viral vectors, liposomes, or nanoparticles.

Delivery systems using viral vectors such as adenoviral or retroviral vectors have high transfection efficacy, but also high immunogenicity and oncogenicity. On the other hand, nonviral delivery systems including nanoparticles have lower cell delivery efficiency than viral delivery systems, but have advantages of having high in-vivo stability, providing target-specific delivery, having improved delivery effects such as uptake and internalization of RNAi oligonucleotides contained therein into cells or tissues, and causing almost no cytotoxicity or immunity stimulation. Therefore, nonviral delivery systems are currently considered more potent than viral delivery systems (Akhtar et al., *J. Clin. Invest.* 117 (12):3623-3632, 2007).

A method using nanocarriers, among the non-viral delivery systems, is designed such that nanoparticles are formed using various polymers such as liposomes and cationic polymer composites, and siRNA loaded on the nanoparticles, that is, nanocarriers, is delivered to cells. Nanocarriers that are typically used include polymeric nanoparticles, polymer micelles, lipoplexes, and the like. Among them, lipoplexes, which are composed of cationic lipids, interact with anionic lipids of endosomes to induce destabilization of the endosomes and deliver the endosomes into cells (*Proc. Natl. Acad. Sci.* 15; 93(21):11493-8, 1996).

In order to improve the efficiency of delivery of siRNA into cells, technology for securing the stability of siRNA and efficient cell membrane permeability using a siRNA conjugate in which a hydrophilic substance (e.g., polyethylene glycol, PEG), which is a biocompatible polymer, is conjugated to siRNA through a simple covalent bond or a linker-mediated covalent bond has been developed (Korean Patent No. 883471). However, chemical modification of siRNA and conjugation thereof to polyethylene glycol (PEG) (PEGylation) still have disadvantages such as low in-vivo stability and inefficient delivery to target organs. In an attempt to solve these disadvantages, a double-stranded oligo RNA construct in which hydrophilic and hydrophobic substances are bound to oligonucleotides, particularly double-stranded oligo RNA such as siRNA, has been developed. This construct forms self-assembled nanoparticles called "SAMiRNA™ (self-assembled micelle inhibitory RNA" (Korean Patent No. 1224828), and the SAMiRNA™ system can obtain more homogenous and much smaller nanoparticles than conventional delivery systems.

Specific examples of the SAMiRNA™ system involve PEG (polyethylene glycol) and HEG (hexaethylene glycol), which are hydrophilic substances. PEG is a synthetic polymer and is often used to increase the solubility of pharmaceuticals, especially, proteins, and to regulate pharmacokinetics. PEG is a polydisperse substance in which the number of a polymer in one batch corresponds to the sum of different numbers of monomers, so the molecular weight forms a Gaussian curve. A polydisperse value (Mw/Mn) indicates the degree of homogeneity of a substance. That is, PEG having a low molecular weight (3-5 kDa) exhibits a polydispersity index of about 1.01, and PEG having a high molecular weight (20 kDa) exhibits a high polydispersity index of about 1.2. In other words, as the molecular weight of a substance increases, the homogeneity of the substance decreases (F. M. Veronese. *Biomaterials* 22:405-417, 2001). Therefore, when PEG is conjugated with pharmaceuticals, the polydispersity of PEG is reflected in the resulting conjugate, disadvantageously making it difficult to verify a single substance. Therefore, in recent years, a substance having a low polydispersity index has been produced through improvement of the PEG synthesis and purification process. However, a conjugate of PEG with a substance having a low molecular weight has problems associated with the polydispersity characteristics of the substance, such as inconvenience in that it is not easy to verify whether or not binding is achieved effectively (Francesco M. DRUG DISCOVERY TODAY 10(21):1451-1458, 2005).

Accordingly, recently, as an improved form of the conventional self-assembled nanoparticle, SAMIRNA™, a novel delivery system having a smaller size and remarkably improved polydispersity compared to conventional SAMiRNA™, was developed by blocking a hydrophilic substance of the double-stranded RNA construct constituting SAMIRNA™ into basic units, each including 1 to 15 uniform monomers having a constant molecular weight and optionally including a linker, and using an appropriate number of basic units as needed.

Meanwhile, it has been reported that the global hair loss market will grow to $11.8 billion by 2024 (Grand View Research, Inc.), 4 out of 7 American men and 1 out of 5 Chinese men are bald, and 90% or more of the cause thereof is known to be androgenetic alopecia. However, most therapeutic agents for hair loss developed to date target DHT and 5-alpha reductase (5-α-reductase), but no agents for treating hair loss or promoting hair growth that target DKK1, which is an important hair loss gene related to androgenetic alopecia, have been developed.

Accordingly, as a result of intensive efforts to develop products for preventing hair loss or promoting hair growth that target DKK1, which is directly related to hair growth, the present inventors have found that DKK1-specific double-stranded oligonucleotides can effectively inhibit the expression of DKK1, and that a double-stranded oligonucleotide construct including the same and a composition containing the same can exhibit excellent effects of preventing hair loss and promoting hair growth. Based on this finding, the present invention has been completed.

Disclosure

Therefore, it is one object of the present invention to provide a double-stranded oligonucleotide enabling highly specific and highly efficient inhibition of DKK1 expression, preferably a double-stranded oligonucleotide including RNA/RNA, DNA/DNA, or a DNA/RNA hybrid form, most preferably a DNA/RNA hybrid form, a double-stranded oligonucleotide construct including the double-stranded oligonucleotide, and nanoparticles including the double-stranded oligonucleotide or the double-stranded oligonucleotide construct.

It is another object of the present invention to provide a pharmaceutical composition or cosmetic composition for preventing hair loss or promoting hair growth containing the DKK1-specific double-stranded oligonucleotide, the double-stranded oligonucleotide construct including the double-stranded oligonucleotide, or nanoparticles including the double-stranded oligonucleotide or the double-stranded oligonucleotide construct as an active ingredient.

It is another object of the present invention to provide the use of the DKK1-specific double-stranded oligonucleotide, the double-stranded oligonucleotide construct including the double-stranded oligonucleotide, or nanoparticles including the double-stranded oligonucleotide or the double-stranded oligonucleotide construct for the prevention of hair loss or promotion of hair growth.

It is another object of the present invention to provide the use of the DKK1-specific double-stranded oligonucleotide, the double-stranded oligonucleotide construct including the double-stranded oligonucleotide, or nanoparticles including the double-stranded oligonucleotide or the double-stranded oligonucleotide construct for the preparation of a drug or cosmetic for preventing hair loss or promoting hair growth.

It is another object of the present invention to provide a method for preventing hair loss or promoting hair growth including administering the DKK1-specific double-stranded oligonucleotide, the double-stranded oligonucleotide construct including the double-stranded oligonucleotide, nanoparticles including the double-stranded oligonucleotide or the double-stranded oligonucleotide construct, or the composition to a subject in need of prevention of hair loss or promotion of hair growth.

In accordance with one aspect of the present invention, the above and other objects can be accomplished by the provision of a double-stranded oligonucleotide including a sense strand having any one sequence selected from the group consisting of SEQ ID NOS: 72, 80, 81, 209, 214, 215, 216, 217, 254 and 256 and an anti-sense strand having a sequence complementary thereto.

In accordance with another aspect of the present invention, provided is a double-stranded oligonucleotide construct having a structure represented by the following Structural Formula (1):

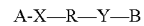

A-X—R—Y—B    Structural Formula (1)

wherein A is a hydrophilic substance, B is a hydrophobic substance, X and Y are each independently a simple covalent bond or a linker-mediated covalent bond, and R is a DKK1-specific double-stranded oligonucleotide including a sense strand having any one sequence selected from the group consisting of SEQ ID NOS: 72, 80, 81, 209, 214, 215, 216, 217, 254 and 256, and an anti-sense strand having a sequence complementary thereto.

In accordance with another aspect of the present invention, provided are nanoparticles including the double-stranded oligonucleotide construct.

In accordance with another aspect of the present invention, provided is a pharmaceutical composition for preventing hair loss or promoting hair growth containing the double-stranded oligonucleotide construct or the nanoparticles as an active ingredient.

In accordance with another aspect of the present invention, provided is a cosmetic composition for preventing hair loss or promoting hair growth containing the double-stranded oligonucleotide construct or the nanoparticles as an active ingredient.

In accordance with another aspect of the present invention, provided is the use of the DKK1-specific double-stranded oligonucleotide, the double-stranded oligonucleotide construct including the double-stranded oligonucleotide, or nanoparticles including the double-stranded oligonucleotide or the double-stranded oligonucleotide construct for the prevention of hair loss or promotion of hair growth.

In accordance with another aspect of the present invention, provided is the use of the DKK1-specific double-stranded oligonucleotide, the double-stranded oligonucleotide construct including the double-stranded oligonucleotide, or nanoparticles including the double-stranded oligonucleotide or the double-stranded oligonucleotide construct for the preparation of a drug for preventing hair loss or promoting hair growth.

In accordance with another aspect of the present invention, provided is the use of the DKK1-specific double-stranded oligonucleotide, the double-stranded oligonucleotide construct including the double-stranded oligonucleotide, or nanoparticles including the double-stranded oligonucleotide or the double-stranded oligonucleotide construct for the preparation of a cosmetic for preventing hair loss or promoting hair growth.

In accordance with another aspect of the present invention, provided is a method for preventing hair loss or promoting hair growth including administering the DKK1-specific double-stranded oligonucleotide, the double-stranded oligonucleotide construct including the double-stranded oligonucleotide, nanoparticles including the double-stranded oligonucleotide or the double-stranded oligonucleotide construct, or the composition to a subject in need of prevention of hair loss or promotion of hair growth.

DESCRIPTION OF DRAWINGS

FIG. 1 shows a process of selecting a candidate sequence including 19 nucleotides by applying a 1-base sliding-window algorithm to a DKK1 mRNA sequence to design a human-DKK1-specific double-stranded oligonucleotide candidate sequence, wherein the following nucleotide sequences are illustrated: GTGGCGGTGGCGGCGCAGAGCTCTGTGCTCCCT-GCAGTCAGGACTCTGGGACCGCAGGG GGCTCCCGGACCCTGACTCTGCAGCCGAACC-GGCACGGTTTC (SEQ ID NO: 314); TCAGGACTCTGGGACCGCA (SEQ ID NO: 315); CAGGACTCTGGGACCGCAG (SEQ ID NO: 316); AGGACTCTGGGACCGCAGG (SEQ ID NO: 317); GGACTCTGGGACCGCAGGG (SEQ ID NO: 318); GACTCTGGGACCGCAGGGG (SEQ ID NO: 319); ACTCTGGGACCGCAGGGGG (SEQ ID NO: 320); CTCTGGGACCGCAGGGGGC (SEQ ID NO: 321); TCTGGGACCGCAGGGGGCT (SEQ ID NO: 322); CTGGGACCGCAGGGGGCTC (SEQ ID NO: 323); TGGGACCGCAGGGGGCTCC (SEQ ID NO: 324); and GGGACCGCAGGGGGCTCCC (SEQ ID NO: 325).

FIG. 4 shows 10 sequences finally selected by treating A549 cells with the 18 sequences having the highest DKK1 expression inhibitory effect.

FIG. 6 shows the nanoparticle size distribution of double-stranded oligonucleotides including randomly selected DKK1-specific oligonucleotides.

FIG. 7 shows the ability of SAMiRNA to inhibit mRNA expression with regard to sequence #72, which was found to have the highest DKK1 expression inhibitory effect.

BEST MODE

Figure 2A:
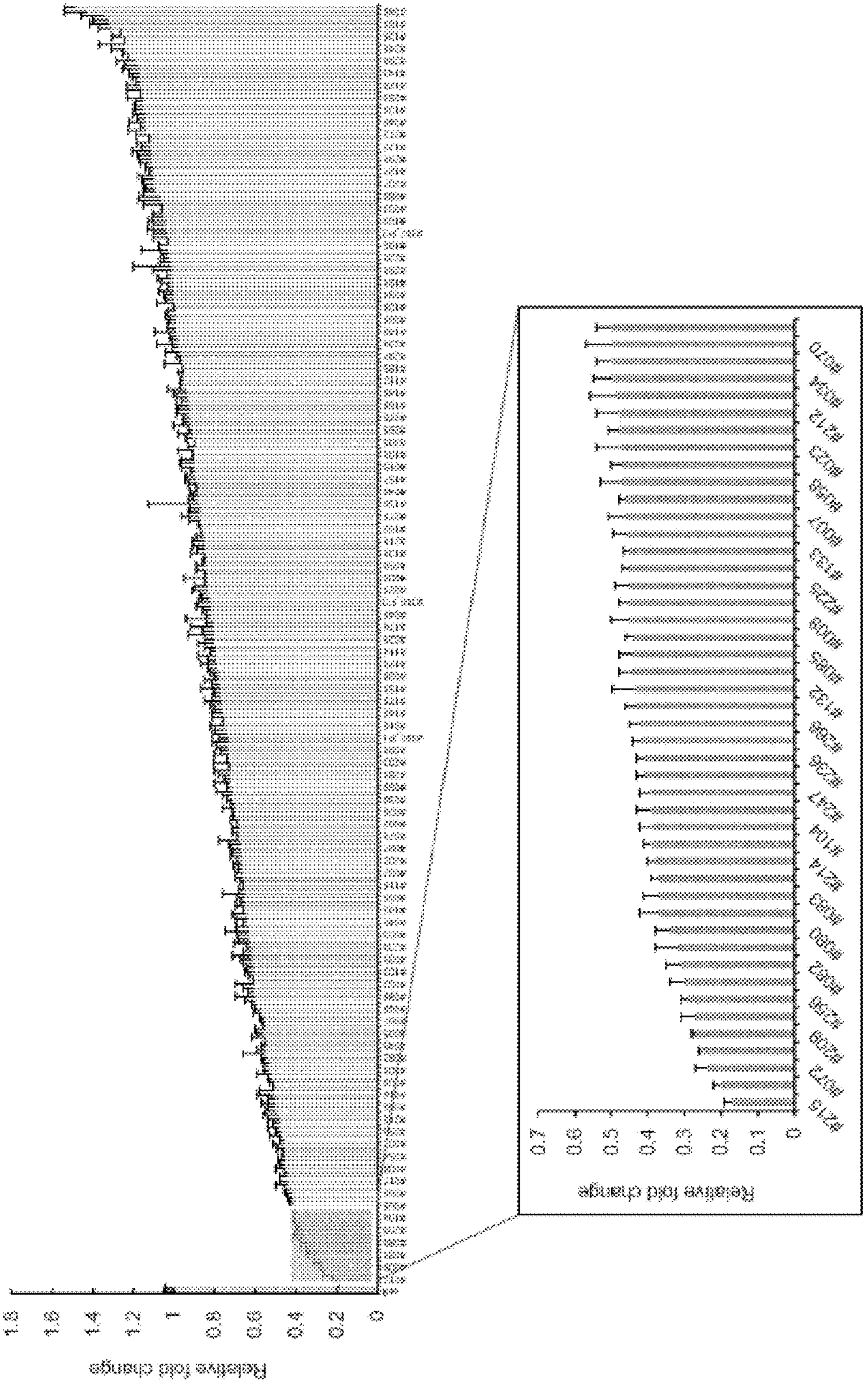
FIGS. 2A and 2B show the results of primary and secondary screening for 312 double-stranded oligo RNAs targeting DKK1.

Unless defined otherwise, all technical and scientific terms used herein have the same meanings as appreciated by those skilled in the field to which the present invention pertains. In general, the nomenclature used herein is well-known in the art and is ordinarily used.

DKK1 is a type of Dickkopf, which is a Wnt inhibitory protein, and was first known as an important protein involved in the formation of amphibian heads. DKK1 is an inhibitor of the Wnt/β-catenin signaling pathway, and has been reported to be involved in Wnt upstream signaling to block Wnt signaling to thereby inhibit the growth of cancer cells (Mao et al., Nature 411:321, 2001; Niida A. et al., *Oncogene* 4:23, 2004). Studies have reported functions of DKK1 including degeneration of neurons in the brain of Alzheimer's disease patients, inhibition of melanocyte growth and differentiation, and stem cell cycle regulation (Caricasole A. et al., J. Neurosci. 24, 2004); Yamaguchi Y. et al., J. Cell. Biol. 165, 2004), and studies have also reported involvement in adipogenesis, chondrogenesis, proliferation of the gastrointestinal epithelium, bone loss associated with rheumatism, and formation of follicular placodes.

There are many reports of an association between cancer and the DKK1 gene because Wnt/P signaling can regulate the epithelial-mesenchymal transition, which is involved in the binding and maintenance of epithelial cells, and thus may affect epithelial cell infiltration and cell differentiation required for the process of cancer cell metastasis. Therefore, DKK1 as an antagonist of Wnt/R signaling can limit the invasiveness of cancer cells in various types of cancer. Recently, it was found that there was a difference in the expression level of DKK1 among non-small cell lung cancer cell lines depending on radiation sensitivity, and that the expression of DKK1 was increased in the A549 and H1299 cell lines, which are highly radiation-resistant cell lines. As a result of inhibition of DKK1 expression in A549 or H1299 using siRNA of DKK1, it was observed that sensitivity to radiation was significantly increased. Therefore, it was also reported that inhibition of DKK1 expression or activity may be important for anticancer treatment (Korean Patent No. 10-1167675).

In addition, interest in hair loss treatment targeting DKK1 has increased since it was discovered that DKK1 plays a very important role in hair growing and degenerating stages.

Most therapeutic agents for hair loss developed to date target DHT and 5-α-reductase. Finasteride, which is an FDA-approved ingredient, is an oral therapeutic agent for hair loss that is used only for male hair loss and is limitedly used because side effects related to reduced male hormone levels have been reported, and the hair growth effect is not maintained upon non-continuous administration. For this reason, finasteride is often used in combination with minoxidil. Finasteride has disadvantages in that it must be administered at a certain time every day, which is inconvenient, due to the drug efficacy period of 24 hours, and is expensive and thus economically inefficient. Minoxidil, which is a therapeutic agent for the scalp, is known to have a negative effect on blood pressure because it has been developed as an antihypertensive, and is used in different contents for men and women. Therapeutic agents for hair loss using the Wnt signaling pathway associated with androgenetic alopecia have already begun to be developed, but therapeutic agents for hair loss and products for promoting hair growth that target DKK1, which is an important hair loss-related gene in the Wnt signaling pathway, have not been developed.

In the present invention, siRNA candidate sequences specific for DKK1 were designed using a 1-base sliding-window algorithm, 312 siRNAs were selected, and among them, 10 siRNAs having particularly excellent effects were selected. In addition, the intracellular delivery efficiency can be increased, and the effects of preventing hair loss and promoting hair growth can be improved by producing the double-stranded oligonucleotide construct (SAMiRNA) and nanoparticles from the siRNA.

In one aspect, the present invention is directed to a double-stranded oligonucleotide including a sense strand having any one sequence selected from the group consisting of SEQ ID NOS: 72, 80, 81, 209, 214, 215, 216, 217, 254 and 256, and an anti-sense strand having a sequence complementary thereto.

As used herein, the term "oligonucleotide" includes all substances having a general RNAi (RNA interference) action, and it will be obvious to those skilled in the art that the DKK1-specific double-stranded oligonucleotide includes DKK1-specific siRNA, shRNA, and the like.

In addition, it will be obvious to those skilled in the art that DKK1-specific siRNA including a sense strand and an antisense strand having a sequence obtained by substituting, deleting or inserting one or more nucleotides in the sense strand having any one sequence selected from the group consisting of SEQ ID NO: 1 to SEQ ID NO: 305 or in the antisense strand complementary thereto also falls within the scope of the present invention, as long as the DKK1-specific siRNA maintains specificity for DKK1.

SEQ ID NOS: 1 to 305 represent human-DKK1-specific sequences, and are siRNA sense strand sequences having homology of 15 nucleotides or less with genes other than DKK1 mRNA (see Table 2). Meanwhile, SEQ ID NOS: 306 to 309 represent human-DKK1-specific siRNA sequences known from related patents (KR 10-1167675, KR 10-2010-0051195) (see Table 3).

An siRNA sequence having superior efficiency and low homology with other human mRNAs according to the present invention was conceived based on a comparison of intracellular activity with the DKK1-specific siRNA sequence disclosed in the related patents. The oligonucleotide according to the present invention is preferably a DKK1-specific double-stranded oligonucleotide having any one sequence selected from the group consisting of SEQ ID NOS: 72, 80, 81, 209, 214, 215, 216, 217, 254 and 256, more preferably a DKK1-specific double-stranded oligonucleotide having the sequence of SEQ ID NO: 72 as a sense strand.

The sense strand or antisense strand of the oligonucleotide according to the present invention preferably consists of 19 to 31 nucleotides, and includes a sense strand having any one sequence selected from SEQ ID NOS: 1 to 305 and an antisense strand complementary thereto.

In the present invention, the oligonucleotide may be siRNA, shRNA, or miRNA.

In addition, in the present invention, the sense or antisense strand may independently be DNA or RNA.

The DKK1-specific double-stranded oligonucleotide provided by the present invention has a nucleotide sequence designed to complementarily bind to the mRNA encoding the gene, and thus can effectively suppress the expression of the gene. In addition, the double-stranded oligonucleotide may include an overhang, which is a structure including one or more unpaired nucleotides at the 3' end of the oligonucleotide.

In addition, in order to improve the in-vivo stability of the double-stranded oligonucleotide, the double-stranded oligonucleotide may include various modifications to provide nuclease resistance and reduce non-specific immune responses. For example, the sense strand or the antisense strand of the double-stranded oligonucleotide may include a chemical modification. The modification of the first or second oligonucleotide constituting the double-stranded oligonucleotide may include one or more selected from the group consisting of: modification through substitution, with methyl ($—CH_3$), methoxy ($—OCH_3$), amine ($—NH_2$), fluorine (—F), —O-2-methoxyethyl, —O-propyl, —O-2 -methylthioethyl, —O-3-aminopropyl, —O-3-dimethylaminopropyl, —O—N-methylacetamido or —O-dimethylamidooxyethyl, of a hydroxyl group (—OH) at the position of a 2' carbon of the sugar structure in at least one nucleotide; modification through substitution, with sulfur, of the oxygen in the sugar structure of the nucleotide; modification of a nucleotide bond into a phosphorothioate, boranophosphate or methyl phosphonate bond; modification into a PNA (peptide nucleic acid), locked nucleic acid (LNA) or unlocked nucleic acid (UNA) form; and modification into a DNA-RNA hybrid form, but is not limited thereto (*Ann. Rev. Med.* 55, 61-65 2004; U.S. Pat. Nos. 5,660,985; 5,958,691; 6,531,584; 5,808,023; 6,326,358; 6,175,001; *Bioorg. Med. Chem. Lett.* 14:1139-1143, 2003; *RNA,* 9:1034-1048, 2003; *Nucleic Acid Res.* 31:589-595, 2003; *Nucleic Acids Research,* 38(17) 5761-5773, 2010; *Nucleic Acids Research,* 39(5) 1823-1832, 2011).

In the present invention, one or more phosphate groups may be bound to the 5' end of the antisense strand of the double-stranded oligonucleotide.

The DKK1-specific double-stranded oligonucleotide provided by the present invention not only inhibits expression of the corresponding gene, but also remarkably inhibits expression of the corresponding protein.

In the present invention, a conjugate in which a hydrophilic substance and a hydrophobic substance are respectively conjugated to both ends of the oligonucleotide was prepared in order to provide efficient in-vivo delivery and improved stability of the DKK1-specific double-stranded oligonucleotide.

The siRNA conjugate in which the hydrophilic substance and the hydrophobic substance are bound to the oligonucleotide as described above forms self-assembled nanoparticles through the hydrophobic interaction of the hydrophobic substance (Korean Patent No. 1224828), and such nanoparticles exhibit extremely excellent in-vivo delivery efficiency and in-vivo stability, and facilitate quality control due to the excellent particle size uniformity, thus being prepared into a drug through a simple process.

That is, in the present invention, the double-stranded oligonucleotide construct (SAMiRNA) and nanoparticles including the prepared DKK1-specific oligonucleotide were prepared.

In another aspect, the present invention is directed to a double-stranded oligonucleotide construct having a structure represented by the following Structural Formula (1):

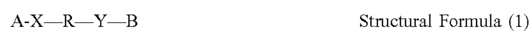

A-X—R—Y—B  Structural Formula (1)

wherein A is a hydrophilic substance, B is a hydrophobic substance, X and Y are each independently a simple covalent bond or a linker-mediated covalent bond, and R is the DKK1-specific double-stranded oligonucleotide described above. In an embodiment, R is a DKK1-specific oligonucleotide including a sense strand having any one sequence selected from the group consisting of SEQ ID NOS: 72, 80, 81, 209, 214, 215, 216, 217, 254 and 256, and an anti-sense strand having a sequence complementary thereto.

Hereinafter, the double-stranded oligonucleotide according to the present invention will be described with a focus on RNA. However, it will be obvious to those skilled in the art that the double-stranded oligonucleotide can be embodied as other kinds of double-stranded oligonucleotides (e.g., DNA/RNA hybrids) having the same properties as the double-stranded oligonucleotide of the present invention.

More preferably, the double-stranded oligonucleotide construct including the DKK1-specific double-stranded oligonucleotide according to the present invention has the structure of the following Structural Formula (2):

Structural Formula (2)

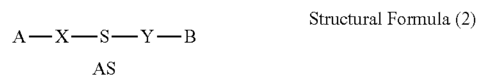

wherein A, B, X and Y are as defined in Structural Formula (1), S is a sense strand of the DKK1-specific double-stranded oligonucleotide, and AS is an antisense strand of the DKK1-specific double-stranded oligonucleotide.

More preferably, the double-stranded oligonucleotide construct including the DKK1-specific double-stranded oligonucleotide has the structure represented by the following Structural Formula (3) or (4):

Structural Formula (3)

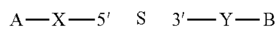

Structural Formula (4)

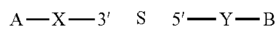

wherein A, B, S, AS, X and Y are as defined in Structural Formula (1), and 5' and 3' represent the 5' and 3' ends of the DKK1-specific double-stranded oligonucleotide sense strand.

It will be obvious to those skilled in the art that the double-stranded oligonucleotide construct including the DKK1-specific double-stranded oligonucleotide in Structural Formulas (1) to (4) may have a structure in which one to three phosphate groups are bound to the 5' end of the antisense strand, and that shRNA may be used instead of siRNA.

The hydrophilic substance in Structural Formulas (1) to (4) is preferably a polymer substance having a molecular weight of 200 to 10,000, and more preferably a polymer material having a molecular weight of 1,000 to 2,000. For example, the hydrophilic polymer substance is preferably a nonionic hydrophilic polymer compound such as polyethylene glycol, polyvinylpyrrolidone, or polyoxazoline, but is not necessarily limited thereto.

In particular, the hydrophilic substance (A) in Structural Formulas (1) to (4) may be used in the form of a hydrophilic substance block represented by the following Structural Formula (5) or Structural Formula (6). By using such a hydrophilic substance block in an appropriate number (n in Structural Formula (5) or Structural Formula (6) below) as necessary, problems resulting from polydispersity that may occur when using general synthetic polymer substances and the like can be greatly improved.

Structural Formula (5)

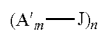

Structural Formula (6)

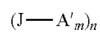

wherein A' is a hydrophilic substance monomer, J is a linker connecting m hydrophilic substance monomers or m hydrophilic substance monomers and siRNA, m is an integer from 1 to 15, n is an integer from 1 to 10, and a repeating unit represented by ($A'_m$-J) or (J-$A'_m$) corresponds to a basic unit of the hydrophilic substance block.

When the hydrophilic substance A has the hydrophilic substance block shown in Structural Formula (5) or Structural Formula (6), the double-stranded oligonucleotide construct including the DKK1-specific double-stranded oligonucleotide according to the present invention has the structure represented by the following Structural Formula (7) or Structural Formula (8):

Structural Formula (7)

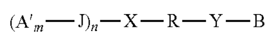

-continued

Structural Formula (8)

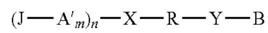

wherein X, R, Y, and B are as defined in Structural Formula (1), and A', J, m, and n are as defined in Structural Formulas (5) and (6).

In Structural Formulas (5) and (6), any of the monomers of the nonionic hydrophilic polymer, preferably a monomer selected from compounds (1) to (3) shown in Table 1, more preferably a monomer of compound (1), may be used as the hydrophilic substance monomer (A') without limitation, as long as it satisfies the objects of the present invention, and G in compound (1) is preferably selected from O, S and NH.

In particular, among hydrophilic substance monomers, the monomer represented by compound (1) has advantages of introducing various functional groups, exhibiting excellent bio-compatibility, such as exhibiting excellent bio-affinity and reduced immune response, and increasing in-vivo stability and efficiency of delivery of the oligonucleotide included in the construct according to Structural Formula (7) or Structural Formula (8), thus being very suitable for the preparation of the construct according to the present invention.

TABLE 1

| Structure of hydrophilic substance monomer according to present invention | | |
|---|---|---|
| Compound (1) | Compound (2) | Compound (3) |
| 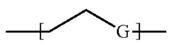 | 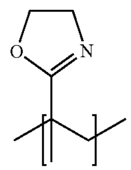 | 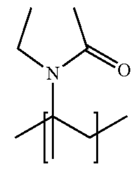 |
| wherein G is O, S or NH. | | |

It is particularly preferred that the hydrophilic substances in Structural Formulas (5) to (8) have a total molecular weight in the range of 1,000 to 2,000. Thus, for example, when a hydrophilic substance wherein hexaethylene glycol, that is, G, according to compound (1) in Structural Formulas (7) and (8), is 0 and m is 6, is used, the molecular weight of a hexaethylene glycol spacer is 344, and thus the number (n) of repetitions is 3 to 5. In particular, in the present invention, the repeating unit of the hydrophilic group represented by ($A'_m$-J) or $(J\text{-}A'_m)_n$ in Structural Formulas (5) and (6), that is, the hydrophilic substance block, is used in an appropriate number, represented by "n" as needed. The hydrophilic substance monomer A and the linker J included in one hydrophilic substance block may be independently the same as or different from those of another hydrophilic substance block. That is, when three hydrophilic substance blocks are used (n=3), different hydrophilic substance monomers may be used for respective hydrophilic substance blocks, for example, the first block contains the hydrophilic substance monomer according to compound (1), the second block contains the hydrophilic substance monomer according to compound (2), and the third block contains the hydrophilic substance monomer according to compound (3), or any one hydrophilic substance monomer selected from the hydrophilic substance monomers according to compounds (1) to (3) may be used for all hydrophilic substance blocks. Similarly, each hydrophilic substance block may use the same different linkers to mediate the binding of the hydrophilic substance monomer. Also, m, indicating the number of hydrophilic substance monomers, may be the same or different between the hydrophilic substance blocks. That is, a different number of hydrophilic substance monomers may be used for all hydrophilic substance blocks; for example, three hydrophilic substance monomers may be linked (m=3) in the first hydrophilic substance block, five hydrophilic substance monomers may be linked (m=5) in the second hydrophilic substance block, and four hydrophilic substance monomers may be linked (m=4) in the third hydrophilic substance block, and the same number of hydrophilic substance monomers may be used for all of the hydrophilic substance blocks. In addition, in the present invention, the linker (J) is preferably selected from the group consisting of $PO_3$—, $SO_3$ and $CO_2$, but is not limited thereto. It will be apparent to those skilled in the art that any linker may be used as long as it satisfies the objects of the present invention according to the monomer of the hydrophilic substance that is used.

The hydrophobic substances (B) in Structural Formulas (1) to (4), Structural Formula (7) and Structural Formula (8) function to form nanoparticles composed of the oligonucleotide constructs according to Structural Formulas (1) to Structural Formulas (4), Structural Formulas (7) and Structural Formulas (8) through hydrophobic interaction. The hydrophobic substance preferably has a molecular weight of 250 to 1,000, and may be a steroid derivative, glyceride derivative, glycerol ether, polypropylene glycol, $C_{12}$ to $C_{50}$ unsaturated or saturated hydrocarbon, diacylphosphatidylcholine, fatty acid, phospholipid, lipopolyamine, lipid, tocopherol, tocotrienol, or the like, but is not limited thereto. It will be obvious to those skilled in the art that any hydrophobic substance can be used, as long as it satisfies the objects of the present invention.

The steroid derivative may be selected from the group consisting of cholesterol, cholestanol, cholic acid, cholesteryl formate, cholestanyl formate, and cholesteryl amine, and the glyceride derivative may be selected from mono-, di- and tri-glycerides and the like. In this case, the fatty acid of the glyceride is preferably a $C_{12}$ to $C_{50}$ unsaturated or saturated fatty acid.

In particular, among the hydrophobic substances, saturated or unsaturated hydrocarbon or cholesterol is preferred in that they have advantages of being easily bound in the step of synthesizing the oligonucleotide construct according to the present invention, and $C_{24}$ hydrocarbon, particularly a form thereof containing a disulfide bond, is most preferred.

The hydrophobic substance is bound to the distal end of the hydrophilic substance, and may be bound to any position of the sense strand or the antisense strand of the double-stranded oligonucleotide or siRNA.

The hydrophilic or hydrophobic substance in Structural Formulas (1) to (4), Structural Formula (7) and Structural Formula (8) according to the present invention is bound to the DKK1-specific double-stranded oligonucleotide through a simple covalent bond or linker-mediated covalent bond (X or Y). The linker mediating the covalent bond is not particularly limited, as long as it covalently bonds with a hydrophilic substance or a hydrophobic substance at the end of the DKK1-receptor-specific double-stranded oligonucleotide, and provides a bond that can be degraded in a specific environment if necessary. Therefore, any compound that mediates binding so as to activate the DKK1-receptor-specific double-stranded oligonucleotide and/or the hydrophilic substance (or the hydrophobic substance) may be used as the linker during the preparation of the double-stranded oligonucleotide construct according to the present invention. The covalent bond may be either a non-degradable bond or a degradable bond. In this case, the non-degradable bond includes an amide bond or a phosphate bond, and the degradable bond includes a disulfide bond, an acid-degradable bond, an ester bond, an anhydride bond, a biodegradable bond or an enzyme-degradable bond, but is not limited thereto.

In addition, any oligonucleotide may be used as the DKK1-specific double-stranded oligonucleotide represented by R (or S and AS) in Structural Formulas (1) to (4) and Structural Formulas (7) and (8) without limitation, as long as it can bind specifically to the mRNA of DKK1, and preferably includes a sense strand having any one sequence selected from the group consisting of SEQ ID NOS: 72, 80, 81, 209, 214, 215, 216, 217, 254 and 256, and an antisense strand having a sequence complementary thereto.

In particular, the double-stranded oligonucleotide included in Structural Formulas (1) to (4) and Structural Formulas (7) and (8) according to the present invention is preferably a DKK1-specific double-stranded oligonucleotide including a sense strand having any one sequence selected from the group consisting of 72, 80, 81, 209, 214, 215, 216, 217, 254 and 256, and an antisense strand having a sequence complementary thereto.

An amine group or polyhistidine group may be further introduced at the distal end of the oligonucleotide of the hydrophilic substance in the double-stranded oligonucleotide construct including the DKK1-specific double-stranded oligonucleotide according to the present invention.

This aims at facilitating the intracellular introduction of carriers of the double-stranded oligonucleotide construct including the DKK1-specific double-stranded oligonucleotide according to the present invention and endosomal escape. The introduction of amine groups, the use of polyhistidine groups, and the effects thereof in order to facilitate the intercellular introduction of carriers, such as quantum dots, dendrimers, and liposomes, and endosomal escape have been reported.

Specifically, it is known that the modified primary amine group at the end or the outside of the carrier is protonated at an in-vivo pH and forms a conjugate with a negatively charged gene through electrostatic interaction, and the carriers can be protected from degradation of lysosomes, because endosomal escape is facilitated due to the internal tertiary amine, which has a buffering effect at a low endosomal pH after intracellular introduction (Gene transfer and expression inhibition using a polymer-based hybrid substance. *Polymer Sci. Technol*., Vol. 23, No. 3, pp254-259).

It is known that histidine, which is a non-essential amino acid, has imidazole (pKa3 of 6.04) at a residue thereof (—R), and thus has the effect of increasing the buffering capacity in endosomes and lysosomes, and thus modification of histidine can be used in order to increase the efficiency of endosomal escape in non-viral gene carriers including liposomes (Novel histidine-conjugated galactosylated cationic liposomes for efficient hepatocyte selective gene transfer in human hepatoma HepG2 cells. *J. Controlled Release* 118, pp262-270).

The amine group or polyhistidine group may be bound to the hydrophilic substance or the hydrophilic substance block through one or more linkers.

In the case where the amine group or polyhistidine group is introduced into the hydrophilic substance of the double-stranded oligonucleotide construct according to Structural Formula (1) of the present invention, the structure shown in Structural Formula (9) is obtained.

Structural Formula (9)

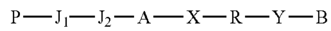

wherein A, B, R, X, and Y are as defined in Structural Formula (1), P is an amine group or a polyhistidine group, and $J_1$ and $J_2$ are linkers and are each independently selected from a simple covalent bond, $PO_3^-$, $SO_3$, $CO_2$, $C_{2-12}$ alkyl, alkenyl, and alkynyl, but are not limited thereto. It will be obvious to those skilled in the art that any linkers satisfying the objects of the present invention depending on the hydrophilic substance that is used may be used as $J_1$ and $J_2$.

When an amine group is introduced, $J_2$ is preferably a simple covalent bond or $PO_3^-$, and $J_1$ is preferably a $C_6$ alkyl, but is not limited thereto.

In addition, when a polyhistidine group is introduced, preferably, in Structural Formula (9), $J_2$ is a simple covalent bond or $PO_3^-$, and $J_1$ is compound (4), but is not limited thereto.

Compound (4)

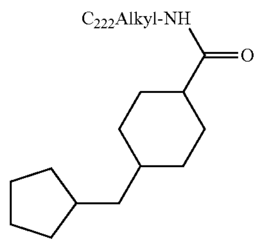

In addition, when the hydrophilic substance of the double-stranded oligonucleotide construct according to Structural Formula (9) is a hydrophilic substance block according to Structural Formula (5) or (6) and an amine group or a polyhistidine group is introduced into the same, the structure represented by the following Structural Formula (10) or Structural Formula (11) is obtained:

Structural Formula (10)

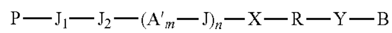

wherein X, R, Y, B, A', J, m, and n are as defined in Structural Formula (5) or (6), and P, $J_1$, and $J_2$ are as defined in Structural Formula (9) above.

In particular, in Structural Formulas (10) and (11), the hydrophilic substance is preferably bound to the 3' end of the sense strand of the DKK1-specific double-stranded oligonucleotide. In this case, Structural Formulas (9) to Structural Formulas (11) may take the form of the following Structural Formulas (12) to (14), respectively.

Structural Formula (12)

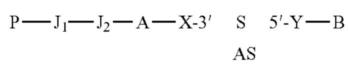

Structural Formula (13)

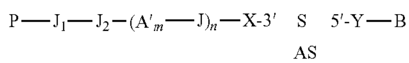

-continued

Structural Formula (14)

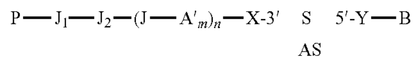

wherein X, R, Y, B, A, A' J, m, n, P, $J_1$, and $J_2$ are as defined in Structural Formulas (9) to (11) above, and 5' and 3' mean the 5' end and 3' end of the sense strand of the DKK1-specific double-stranded oligonucleotide.

The amine group that can be introduced in the present invention may be any of primary to tertiary amine groups, and is particularly preferably a primary amine group. The introduced amine group may be present as an amine salt; for example, the salt of the primary amine group may be present in the form of $NH_3^+$.

In addition, the polyhistidine group that can be introduced in the present invention may include 3 to 10 histidines, particularly preferably 5 to 8 histidines, and most preferably 6 histidines. Additionally, one or more cysteines may be included, in addition to histidine.

Meanwhile, if a targeting moiety is provided in the double-stranded oligonucleotide construct including the DKK1-specific double-stranded oligonucleotide according to the present invention and the nanoparticles formed therefrom, delivery to target cells can be efficiently promoted even at a dose with a relatively low concentration, excellent target gene expression control function can be obtained, and the non-specific delivery of the DKK1-specific double-stranded oligonucleotide to other organs and cells can be prevented.

Accordingly, the present invention provides a double-stranded oligonucleotide in which a ligand (L), in particular, a ligand having the property of specifically binding to a receptor that promotes internalization of target cells through receptor-mediated endocytosis (RME), is further bound to the hydrophilic substance of the constructs according to Structural Formulas (1) to (4) and Structural Formulas (7) and (8). The form in which the ligand is bound to the double-stranded oligonucleotide construct represented by Structural Formula (1) has the structure represented by the following Structural Formula (15)

Structural Formula (15)

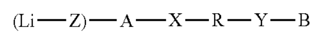

wherein A, B, X, and Y are as defined in Structural Formula (1) above, L is a ligand having the property of specifically binding to a receptor that promotes internalization of target cells through receptor-mediated endocytosis (RME), and i is an integer of 1 to 5, preferably an integer of 1 to 3.

The ligand in Structural Formula (15) is preferably selected from target-receptor-specific antibodies, aptamers, or peptides having the RME property for enhancing internalization in a target-cell-specific manner; or chemicals such as folate (generally "folate" and "folic acid" are used interchangeably, and folate in the present invention refers to folate in a natural state or an activated state in the human body), sugars including hexamines such as N-acetyl galactosamine (NAG), glucose, and mannose, or carbohydrates, but is not limited thereto.

In addition, the hydrophilic substance A in Structural Formula (15) may be used in the form of a hydrophilic substance block according to Structural Formulas (5) and (6).

In another aspect, the present invention is directed to nanoparticles including the double-stranded oligonucleotide construct including the DKK1-specific double-stranded oligonucleotide.

As described above, the double-stranded oligonucleotide construct including the DKK1-specific double-stranded oligonucleotide includes both hydrophobic and hydrophilic substances and thus is amphiphilic, and the hydrophilic substance has affinity to water molecules in the body through interactions such as hydrogen bonds therewith, and thus is directed outwards, and the hydrophobic substance is directed inwards through hydrophobic interaction between hydrophobic molecules, resulting in the formation of thermodynamically stable nanoparticles. That is, the hydrophobic substance is positioned at the center of the nanoparticles, and the hydrophilic substance is positioned at the periphery of the DKK1-specific double-stranded oligonucleotide to thereby form nanoparticles that protect the DKK1-specific double-stranded oligonucleotide. The nanoparticles thus formed improve intracellular delivery and efficacy of DKK1-specific double-stranded oligonucleotides.

The nanoparticles according to the present invention may be formed only with double-stranded oligonucleotide constructs including double-stranded oligonucleotides having the same sequence, or with a mixture of double-stranded oligonucleotide constructs including double-stranded oligonucleotides having different sequences. The double-stranded oligonucleotides having different sequences in the present invention are to be interpreted as including double-stranded oligonucleotides specific for a different target gene, for example, DKK1, and may have the same target gene specificity but different sequences.

Also, in addition to the DKK1-specific double-stranded oligonucleotide, a double-stranded oligonucleotide construct including another hair-loss-associated gene-specific double-stranded oligonucleotide may be included in the nanoparticles according to the present invention.

In the present invention, the nanoparticles may be lyophilized.

It was found in the present invention that the double-stranded oligonucleotide construct (SAMiRNA) and nanoparticles have effects of preventing hair loss and promoting hair growth.

In another aspect, the present invention is directed to a pharmaceutical composition for preventing hair loss, especially androgenic alopecia, or promoting hair growth containing the double-stranded oligonucleotide construct including the DKK1-specific double-stranded oligonucleotide and/or the nanoparticles including the DKK1-specific double-stranded oligonucleotide.

The pharmaceutical composition may be used as a formulation selected from ointments, pastes, gels, jellies, serums, aerosol sprays, non-aerosol sprays, foams, creams, lotions, solutions and suspensions, but is not limited thereto.

In another aspect, the present invention is directed to a cosmetic composition for preventing hair loss, especially androgenic alopecia, or promoting hair growth containing the double-stranded oligonucleotide construct including the DKK1-specific double-stranded oligonucleotide and/or the nanoparticles including the DKK1-specific double-stranded oligonucleotide.

The composition is used as a formulation selected from the group consisting of hair tonics, hair conditioners, hair essences, hair lotions, hair nutrition lotions, hair shampoos, hair conditioners, hair treatments, hair creams, hair nutrition creams, hair moisture creams, hair massage creams, hair waxes, hair aerosols, hair packs, hair nutrition packs, hair soaps, hair cleansing foams, hair oils, hair drying agents, hair preservatives, hair dyes, hair wave creams, hair bleaches, hair gels, hair glazes, hair dressings, hair lacquers, hair moisturizers, hair mousses, and hair sprays.

The composition containing the DKK1-specific double-stranded oligonucleotide, the double-stranded oligonucleotide construct including the same, and/or nanoparticles including the double-stranded oligonucleotide construct according to the present invention as an active ingredient is effective in preventing hair loss or inducing hair growth by suppressing the expression of DKK1, which is a hair loss gene induced by DHT.

In particular, the composition for preventing hair loss or promoting hair growth according to the present invention may contain the double-stranded oligonucleotide construct including a sense strand having any one sequence selected from the group consisting of SEQ ID NOS: 72, 80, 81, 209, 214, 215, 216, 217, 254 and 256, and an antisense strand having a sequence complementary thereto.

In addition, the composition according to the present invention may further contain a double-stranded oligonucleotide specific for a gene associated with a hair loss disease, or a double-stranded oligonucleotide construct including the same, other than the double-stranded oligonucleotide construct including the DKK1-specific double-stranded oligonucleotide.

The composition according to the present invention may be applied to the prevention of hair loss associated with a gene involved in upstream or downstream signaling of DKK1, particularly, androgenic alopecia, but is not limited thereto.

The composition of the present invention may be prepared by incorporating one or more pharmaceutically acceptable carriers, in addition to the active ingredient described above. The pharmaceutically acceptable carrier should be compatible with the active ingredient of the present invention, and may include saline, sterile water, Ringer's solution, buffered saline, a dextrose solution, a maltodextrin solution, glycerol, ethanol, or a combination of two or more thereof. The composition may optionally contain other conventional additives, such as antioxidants, buffers, and bacteriostats. In addition, the composition may be prepared as an injectable formulation, such as an aqueous solution, suspension, or emulsion, by further adding a diluent, dispersant, surfactant, binder or lubricant thereto. In particular, the composition is preferably prepared as a lyophilizate formulation. The lyophilizate formulation may be prepared using a method commonly known in the art to which the present invention pertains, or by further adding a stabilizer for lyophilization. Furthermore, the lyophilizate formulation is preferably prepared according to each disease or component using an appropriate method known in the art or a method disclosed in Remington's Pharmaceutical Science (Mack Publishing company, Easton PA).

The content of the active ingredient or the like included in the composition of the present invention and the administration method thereof may be determined by those skilled in the art based on typical symptoms of individuals and the severity of hair loss. In addition, the composition may be prepared in various forms such as powders, tablets, injections, ointments and functional cosmetics, and may be provided in unit-dose or multi-dose containers, for example sealed ampoules and vials.

In another aspect, the present invention is directed to a method for preventing hair loss or promoting hair growth including administering the DKK1-specific double-stranded oligonucleotide, the double-stranded oligonucleotide construct including the double-stranded oligonucleotide, or nanoparticles including the same to a subject in need of promotion of hair growth. The present invention is directed to a method of preventing a hair loss disease, in particular, androgenic alopecia, alopecia areata or telogen alopecia, or promoting or inducing hair growth.

In another aspect, the present invention is directed to the use of the DKK1-specific double-stranded oligonucleotide, the double-stranded oligonucleotide construct including the double-stranded oligonucleotide, or nanoparticles including the double-stranded oligonucleotide or the double-stranded oligonucleotide construct for the prevention of hair loss or promotion of hair growth.

In another aspect, the present invention is directed to the use of the DKK1-specific double-stranded oligonucleotide, the double-stranded oligonucleotide construct including the double-stranded oligonucleotide, or nanoparticles including the double-stranded oligonucleotide or the double-stranded oligonucleotide construct for the preparation of a drug for preventing hair loss or promoting hair growth.

In another aspect, the present invention is directed to the use of the DKK1-specific double-stranded oligonucleotide, the double-stranded oligonucleotide construct including the double-stranded oligonucleotide, or nanoparticles including the double-stranded oligonucleotide or the double-stranded oligonucleotide construct for the preparation of a cosmetic for preventing hair loss or promoting hair growth.

When the DKK1-specific double-stranded oligonucleotide, the construct including the double-stranded oligonucleotide, the composition containing the same, or nanoparticles including the same are used for the preparation of functional cosmetics or external preparations for skin, the formulation of functional cosmetics or external preparations for skin is selected from creams, lotions, gels, water-soluble liquids and essences, but is not limited thereto.

In the present invention, the hair loss includes all of androgenic alopecia, alopecia areata, and telogen alopecia.

Example

Hereinafter, the present invention will be described in more detail with reference to examples. However, it will be obvious to those skilled in the art that these examples are provided only for illustration of the present invention and should not be construed as limiting the scope of the present invention.

Example 1: Selection of Algorithmic Candidate Sequences for Screening of siRNA Targeting DKK1

312 target nucleotide sequences (sense strands) capable of binding to the mRNA sequence (NM_012242.3, 1913 bp) of the DKK1 (*Homo sapiens*) gene were designed.

More specifically, the design process for the siRNA candidate sequences for DKK1 was performed by reviewing the exon map of human DKK1 mRNA, designing candidate sequences including 19 nucleotides using the 1-base sliding window algorithm, and performing BLAST at an e-value of 100 or less on a list of siRNA candidate sequences compared with human total reference req RNA to select 305 siRNA candidate sequences having RNA sequence identity of 15 nucleotides or less with other genes (Table 2). At this time, a DKK1 inhibition experiment was performed using a total of 312 siRNA sequences, including the four siRNA sequences (Table 4) mentioned in the known literature (KR 10-1167675, KR 10-2010-0051195) (FIG. 1).

TABLE 2

305 DKK1-specific siRNA candidate sequences selected using 1-base sliding window screening

| SEQ ID NO: | Accession No. | Code Name | Sense Strand Sequence |
|---|---|---|---|
| 1 | NM_012242.3 | SAMi-hDKK1#001 | TCAGGACTCTGGGACCGCA |
| 2 | NM_012242.3 | SAMi-hDKK1#002 | CAGGACTCTGGGACCGCAG |
| 3 | NM_012242.3 | SAMi-hDKK1#003 | AGGACTCTGGGACCGCAGG |
| 4 | NM_012242.3 | SAMi-hDKK1#004 | GGACTCTGGGACCGCAGGG |
| 5 | NM_012242.3 | SAMi-hDKK1#005 | CTGCAGCCGAACCGGCACG |
| 6 | NM_012242.3 | SAMi-hDKK1#006 | TGCAGCCGAACCGGCACGG |
| 7 | NM_012242.3 | SAMi-hDKK1#007 | GCAGCCGAACCGGCACGGT |
| 8 | NM_012242.3 | SAMi-hDKK1#008 | CAGCCGAACCGGCACGGTT |
| 9 | NM_012242.3 | SAMi-hDKK1#009 | AGCCGAACCGGCACGGTTT |
| 10 | NM_012242.3 | SAMi-hDKK1#010 | GCCGAACCGGCACGGTTTC |
| 11 | NM_012242.3 | SAMi-hDKK1#011 | CCGAACCGGCACGGTTTCG |
| 12 | NM_012242.3 | SAMi-hDKK1#012 | CGAACCGGCACGGTTTCGT |
| 13 | NM_012242.3 | SAMi-hDKK1#013 | GAACCGGCACGGTTTCGTG |
| 14 | NM_012242.3 | SAMi-hDKK1#014 | AACCGGCACGGTTTCGTGG |
| 15 | NM_012242.3 | SAMi-hDKK1#015 | ACCGGCACGGTTTCGTGGG |
| 16 | NM_012242.3 | SAMi-hDKK1#016 | CCGGCACGGTTTCGTGGGG |
| 17 | NM_012242.3 | SAMi-hDKK1#017 | CGGCACGGTTTCGTGGGGA |
| 18 | NM_012242.3 | SAMi-hDKK1#018 | GGCACGGTTTCGTGGGGAC |
| 19 | NM_012242.3 | SAMi-hDKK1#019 | AGGCTTGCAAAGTGACGGT |
| 20 | NM_012242.3 | SAMi-hDKK1#020 | GGCTTGCAAAGTGACGGTC |
| 21 | NM_012242.3 | SAMi-hDKK1#021 | GCTTGCAAAGTGACGGTCA |
| 22 | NM_012242.3 | SAMi-hDKK1#022 | GCGCAGCGGGAGCTACCCG |
| 23 | NM_012242.3 | SAMi-hDKK1#023 | CGCAGCGGGAGCTACCCGG |
| 24 | NM_012242.3 | SAMi-hDKK1#024 | GAGCTACCCGGGTCTTTGT |

TABLE 2-continued

305 DKK1-specific siRNA candidate sequences selected using 1-base sliding window screening

| SEQ ID NO: | Accession No. | Code Name | Sense Strand Sequence |
|---|---|---|---|
| 25 | NM_012242.3 | SAMi-hDKK1#025 | AGCTACCCGGGTCTTTGTC |
| 26 | NM_012242.3 | SAMi-hDKK1#026 | GCTACCCGGGTCTTTGTCG |
| 27 | NM_312242.3 | SAMi-hDKK1#027 | CTACCCGGGTCTTTGTCGC |
| 28 | NM_012242.3 | SAMi-hDKK1#028 | TACCCGGGTCTTTG1CGCG |
| 29 | NM_012242.3 | SAMi-hDKK1#029 | ACCCGGGTCTTTGTCGCGA |
| 30 | NM_312242.3 | SAMi-hDKK1#030 | CCCGGGTCTTTGTC6CGAT |
| 31 | NM_0122423 | SAMi-hDKK1#031 | CCGGGTCTTTGTCGCGATG |
| 32 | NM_012242.3 | SAMi-hDKK1#032 | CGGGTCTTTGTCGCGATGG |
| 33 | NM_012242.3 | SAMi-hDKK1#033 | GGGTCTTTGTCGCGATGGT |
| 34 | NM_012242.3 | SAMi-hDKK1#034 | GGTCTTTGTCGCGATGGTA |
| 35 | NM_012242.3 | SAMi-hDKK1#035 | GTCTTTGTCGCGATGGTAG |
| 36 | NM_012242.3 | SAMi-hDKK1#036 | TCTTTGTCGCGATGGTAGC |
| 37 | NM_012242.3 | SAMi-hDKK1#037 | CTTTGTCGCGATGGTAGCG |
| 38 | NM_012242.3 | SAMi-hDKK1#038 | TTTGTCGCGATGGTAGCGG |
| 39 | NM_012242.3 | SAMi-hDKK1#039 | TTGTCGCGATGGTAGCGGC |
| 40 | NM_012242.3 | SAMi-hDKK1#040 | TGTCGCGATGGTAGCGGCG |
| 41 | NM_012242.3 | SAMi-hDKK1#041 | GGAGTGAGCGCCACCTTGA |
| 42 | NM_012242.3 | SAMi-hDKK1#042 | CCACCTTGAACTCGGTTCT |
| 43 | NM_012242.3 | SAMi-hDKK1#043 | CACCTTGAACTCGGTTCTC |
| 44 | NM_012242.3 | SAMi-hDKK1#044 | ACCTTGAACTCGGTTCTCA |
| 45 | NM_012242.3 | SAMi-hDKK1#045 | CCTTGAACTCGGTTCTCAA |
| 46 | NM_012242.3 | SAMi-hDKK1#046 | CTTGAACTCGGTTCTCAAT |
| 47 | NM_012242.3 | SAMi-hDKK1#047 | ACTCGGTTCTCAATTCCAA |
| 48 | NM_012242.3 | SAMi-hDKK1#048 | GTTCTCAATTCCAACGCTA |

TABLE 2-continued

305 DKK1-specific siRNA candidate sequences selected using 1-base sliding window screening

| SEQ ID NO: | Accession No. | Code Name | Sense Strand Sequence |
|---|---|---|---|
| 49 | NM_012242.3 | SAMi-hDKK1#049 | ATTCCAACGCTATCAAGAA |
| 50 | NM_012242.3 | SAMi-hDKK1#050 | TTCCAACGCTATCAAGAAC |
| 51 | NM_012242.3 | SAMi-hDKK1#051 | AAGAACCTGCCCCCACCGC |
| 52 | NM_012242.3 | SAMi-hDKK1#052 | AGAACCTGCCCCCACCGCT |
| 53 | NM_012242.3 | SAMi-hDKK1#053 | GCGCCGGGAATCCTGTACC |
| 54 | NM_012242.3 | SAMi-hDKK1#054 | CGCCGGGAATCCTGTACCC |
| 55 | NM_012242.3 | SAMi-hDKK1#055 | GCCGGGAATCCTGTACCCG |
| 56 | NM_012242.3 | SAMi-hDKK1#056 | ATCCTGTACCCGGGCGGGA |
| 57 | NM_012242.3 | SAMi-hDKK1#057 | TCCTGTACCCGGGCGGGAA |
| 53 | NM_0.12242.3 | SAMi-hDKK1#058 | CCTGTACCCGGGCGGGAAT |
| 59 | NM_012242.3 | SAMi-hDKK1#059 | CTGTACCCGGGCGGGAATA |
| 60 | NM_012242.3 | SAMi-hDKK1#060 | TGTACCCGGGCGGGAATAA |
| 61 | NM_012242.3 | SAMi-hDKK1#061 | GTACCCGGGCGGGAATAAG |
| 62 | NM_012242.3 | SAMi-hDKK1#062 | CCGGGCGGGAAfAAGTACC |
| 63 | NM_012242.3 | SAMi-hDKK1#063 | CGGGCGGGAATAAGTACCA |
| 64 | NM_012242.3 | SAMi-hDKK1#064 | GGGCGGGAATAAGTACCAG |
| 65 | NM_012242.3 | SAMi-hDKK1#065 | GGCGGGAATAAGTACCAGA |
| 66 | NM_012242.3 | SAMi-hDKK1#066 | GCGGGAATAAGTACCAGAC |
| 67 | NM_012242.3 | SAMi-hDKK1#067 | CGGGAATAAGTACCAGACC |
| 63 | NM_012242.3 | SAMi-hDKK1#068 | GGGAATAAGTACCAGACCA |
| 69 | NM_012242.3 | SAMi-hDKK1#069 | GGAATAAGTACCAGACCAT |
| 70 | NM_012242.3 | SAMi-hDKK1#070 | GAATAAGTACCAGACCATT |
| 71 | NM_012242.3 | SAMi-hDKK1#071 | AATAAGTACCAGACCATTG |
| 72 | NM_012242.3 | SAMi-hDKK1#072 | ATAAGTACCAGACCATTGA |

TABLE 2-continued

305 DKK1-specific siRNA candidate sequences selected using 1-base sliding window screening

| SEQ ID NO: | Accession No. | Code Name | Sense Strand Sequence |
|---|---|---|---|
| 73 | NM_012242.3 | SAMi-hDKK1#073 | TAAGTACCAGACCATTGAC |
| 74 | NM_012242.3 | SAMi-hDKK1#074 | AAGTACCAGACCATTGACA |
| 75 | NM_012242.3 | SAMi-hDKK1#075 | AGTACCAGACCATTGACAA |
| 76 | NM_012242.3 | SAMi-hDKK1#076 | CCAGACCATTGACAACTAC |
| 77 | NM_012242.3 | SAMi-hDKK1#077 | CAGACCATTGACAACTACC |
| 78 | NM_012242.3 | SAMi-hDKK1#078 | AGACCATTGACAACTACCA |
| 79 | NM_012242.3 | SAMi-hDKK1#079 | CATTGACAACTACCAGCCG |
| 80 | NM_012242.3 | SAMi-hDKK1#080 | ATTGACAACTACCAGCCGT |
| 81 | NM_012242.3 | SAMi-hDKK1#081 | TTGACAACTACCAGCCGTA |
| 82 | NM_012242.3 | SAMi-hDKK1#082 | TGACAACTACCAGCCGTAC |
| 83 | NM_012242.3 | SAMi-hDKK1#083 | GACAACTACCAGCCGTACC |
| S4 | NM_012242.3 | SAMi-hDKK1#084 | ACAACTACCAGCCGTACCC |
| 85 | NM_012242.3 | SAMi-hDKK1#085 | CAACTACCAGCCGTACCCG |
| 86 | NM_012242.3 | SAMi-hDKK1#086 | AACTACCAGCCGTACCCGT |
| 87 | NM_012242.3 | SAMi-hDKK1#087 | AGCCGTACCCGTGCGCAGA |
| 88 | NM_012242.3 | SAMi-hDKK1#088 | GCCGTACCCGTGCGCAGAG |
| 89 | NM_012242.3 | SAMi-hDKK1#089 | CCGTACCCGTGCGCAGAGG |
| 90 | NM_012242.3 | SAMi-hDKK1#090 | CGTACCCGTGCGCAGAGGA |
| 91 | NM_012242.3 | SAMi-hDKK1#091 | GTACCCGTGCGCAGAGGAC |
| 92 | NM_012242.3 | SAMi-hDKK1#092 | TACCCGTGCGCAGAGGACG |
| 93 | NM_012242.3 | SAMi-hDKK1#093 | GACGAGGAGTGCGGCACTG |
| 94 | NM_012242.3 | SAMi-hDKK1#094 | ACGAGGAGTGCGGCACTGA |
| 95 | NM_012242.3 | SAMi-hDKK1#095 | CGAGGAGTGCGGCACTGAT |
| 96 | NM_012242.3 | SAMi-hDKK1#096 | GAGGAGTGCGGCACTGATG |

TABLE 2-continued

305 DKK1-specific siRNA candidate sequences selected using 1-base sliding window screening

| SEQ ID NO: | Accession No. | Code Name | Sense Strand Sequence |
|---|---|---|---|
| 97 | NM_012242.3 | SAMi-hDKK1#097 | AGGAGTGCGGCACTGATGA |
| 98 | NM_012242.3 | SAMi-hDKK1#098 | GGAGTGCGGCACTGATGAG |
| 99 | NM_012242.3 | SAMi-hDKK1#099 | GAGTGCGGCACTGATGAGT |
| 100 | NM_012242.3 | SAMi-hDKK1#100 | AGTGCGGCACTGATGAGTA |
| 101 | NM_012242.3 | SAMi-hDKK1#101 | GTGCGGCACTGATGAGTAC |
| 102 | NM_012242.3 | SAMi-hDKK1#102 | TGCGGCACTGATGAGTACT |
| 103 | NM_012242.3 | SAMi-hDKK1#103 | GCGGCACTGATGAGTACTG |
| 104 | NM_012242.3 | SAMi-hDKK1#104 | CACTGATGAGTACTGCGCT |
| 105 | NM_012242.3 | SAMi-hDKK1#105 | GATGAGTACTGCGCTAGTC |
| 106 | NM_012242.3 | SAMi-hDKK1#106 | AGTACTGCGCTAGTCCCAC |
| 107 | NM_012242.3 | SAMi-hDKK1#107 | CTGCGCTAGTCCCACCCGC |
| 108 | NM_012242.3 | SAMi-hDKK1#108 | TGCGCTAGTCCCACCCGCG |
| 109 | NM_012242.3 | SAMi-hDKK1#109 | GCGCTAGTCCCACCCGCGG |
| 110 | NM_012242.3 | SAMi-hDKK1#110 | CGCTAGTCCCACCCGCGGA |
| 111 | NM_012242.3 | SAMi-hDKK1#111 | AGGGGACGCAGGCGTGCAA |
| 112 | NM_012242.3 | SAMi-hDKK1#112 | GGGGACGCAGGCGTGCAAA |
| 113 | NM_012242.3 | SAMi-hDKK1#113 | GGGACGCAGGCGTGCAAAT |
| 114 | NM_012242.3 | SAMi-hDKK1#114 | GGACGCAGGCGTGCAAATC |
| 115 | NM_012242.3 | SAMi-hDKK1#115 | GACGCAGGCGTGCAAATCT |
| 11G | NM_012242.3 | SAMi-hDKK1#116 | ACGCAGGCGTGCAAATCTG |
| 117 | NM_012242.3 | SAMi-hDKK1#117 | CGCAGGCGTGCAAATCTGT |
| 118 | NM_012242.3 | SAMi-hDKK1#118 | GCAAATCTGTCTCGCCTGC |
| 119 | NM_012242.3 | SAMi-hDKK1#119 | CAAATCTGTCTCGCCTGCA |

TABLE 2-continued

305 DKK1-specific siRNA candidate sequences selected using 1-base sliding window screening

| SEQ ID NO: | Accession No. | Code Name | Sense Strand Sequence |
|---|---|---|---|
| 120 | NM_012242.3 | SAMi-hDKK1#120 | AAATCTGTCTCGCCTGCAG |
| 121 | NM_012242.3 | SAMi-hDKK1#121 | GGAAGCGCCGAAAACGCTG |
| 122 | NM_012242.3 | SAMi-hDKK1#122 | GAAGCGCCGAAAACGCTGC |
| 123 | NM_012242.3 | SAMi-hDKK1#123 | AAGCGCCGAAAACGCTGCA |
| 124 | NM_012242.3 | SAMi-hDKK1#124 | AGCGCCGAAAACGCTGCAT |
| 125 | NM_012242.3 | SAMi-hDKK1#125 | GCGCCGAAAACGCTGCATG |
| 126 | NM_012242.3 | SAMi-hDKK1#126 | CGCCGAAAACGCTGCATGC |
| 127 | NM_012242.3 | SAMi-hDKK1#127 | GCCGAAAACGCTGCATGCG |
| 128 | NM_012242.3 | SAMi-hDKK1#128 | CCGAAAACGCTGCATGCGT |
| 129 | NM_012242.3 | SAMi-hDKK1#123 | AAACGCTGCATGCGTCACG |
| 130 | NM_012242.3 | SAMi-hDKK1#130 | AACGCTGCATGCGTCACGC |
| 131 | NM_012242.3 | SAMi-hDKK1#131 | ACGCTGCATGCGTCACGCT |
| 132 | NM_012242.3 | SAMi-hDKK1#132 | CGCTGCATGCGTCACGCTA |
| 133 | NM_012242.3 | SAMi-hDKK1#133 | GCTGCATGCGTCACGCTAT |
| 134 | NM_012242.3 | SAMi-hDKK1#134 | CTGCATGCGTCACGCTATG |
| 135 | NM_012242.3 | SAMi-hDKK1#135 | TGCATGCGTCACGCTATGT |
| 136 | NM_012242.3 | SAMi-hDKK1#136 | GCATGCGTCACGCTATGTG |
| 137 | NM_012242.3 | SAMi-hDKK1#137 | CATGCGTCACGCTATGTGC |
| 138 | NM_012242.3 | SAMi-bDKK1#133 | ATGCGTCACGCTATGTGCT |
| 139 | NM_012242.3 | SAMi-hDKK1#139 | TGCGTCACGCTATGTGCTG |
| 140 | NM_012242.3 | SAMi-hDKK1#140 | GCGTCACGCTATGTGCTGC |
| 141 | NM_012242.3 | SAMi-hDKK1#141 | CGTCACGCTATGTGCTGCC |
| 142 | NM_012242.3 | SAMi-hDKK1#142 | GTCACGCTATGTGCTGCCC |
| 143 | NM_012242.3 | SAMi-Hdkk1#143 | TCACGCTATGTGCTGCCCC |

TABLE 2-continued

305 DKK1-specific siRNA candidate sequences selected using 1-base sliding window screening

| SEQ ID NO: | Accession No. | Code Name | Sense Strand Sequence |
|---|---|---|---|
| 144 | NM_012242.3 | SAMi-hDKK1#144 | CACGCTATGTGCTGCCCCG |
| 145 | NM_012242.3 | SAMi-hDKK1#145 | ACGCTATGTGCTGCCCCGG |
| 146 | NM_012242.3 | SAMi-hDKK1#146 | CGCTATGTGCTGCCCCGGG |
| 147 | NM_012242.3 | SAMi-hDKK1#147 | GCTATGTGCTGCCCCGGGA |
| 148 | NM_012242.3 | SAMi-hDKK1#143 | GTGCTGCCCCGGGAATTAC |
| 149 | NM_012242.3 | SAMi-hDKK1#149 | TGCTGCCCCGGGAATTACT |
| 150 | NM_012242.3 | SAMi-hDKK1#150 | GCTGCCCCGGGAATTACTG |
| 151 | NM_012242.3 | SAMi-hDKK1#151 | CTGCCCCGGGAATTACTGC |
| 152 | NM_012242.3 | SAMi-hDKK1#152 | TGCCCCGGGAATTACTGCA |
| 153 | NM_012242.3 | SAMi-hDKK1#153 | GCCCCGGGAATTACTGCAA |
| 154 | NM_012242.3 | SAMi-hDKK1#154 | CCCCGGGAATTACTGCAAA |
| 155 | NM_012242.3 | SAMi-hDKK1#155 | GGAATATGTGTGTCTTCTG |
| 156 | NM_012242.3 | SAMi-hDKK1#156 | CTTTGGTAATGATCATAGC |
| 157 | NM_012242.3 | SAMi-hDKK1#157 | TTTGGTAATGATCATAGCA |
| 158 | NM_012242.3 | SAMi-hDKK1#158 | TTGGTAATGATCATAGCAC |
| 159 | NM_012242.3 | SAMi-hDKK1#159 | TGGTAATGATCATAGCACC |
| 160 | NM_012242.3 | SAMi-hDKK1#160 | TGATCATAGCACCTTGGAT |
| 161 | NM_012242.3 | SAMi-hDKK1#K61 | GATCATAGCACCTTGGATG |
| 162 | NM_012242.3 | SAMi-hDKK1#i62 | ATCATAGCACCTTGGATGG |
| 163 | NM_012242.3 | SAMi-hDKK1#163 | TCATAGCACCTTGGATGGG |
| 164 | NM_012242.3 | SAMi-hDKK1#164 | CATAGCACCTTGGATGGGT |
| 165 | NM_012242.3 | SAMi-hDKK1#165 | GCACCTTGGATGGGTATTC |
| 166 | NM_012242.3 | SAMi-hDKK1#166 | CACCTTGGATGGGTATTCC |
| 167 | NM_012242.3 | SAMi-hDKK1#167 | ACCTTGGATGGGTATTCCA |

TABLE 2-continued

305 DKK1-specific siRNA candidate sequences selected using 1-base sliding window screening

| SEQ ID NO: | Accession No. | Code Name | Sense Strand Sequence |
|---|---|---|---|
| 168 | NM_012242.3 | SAMi-hDKK1#168 | TGGATGGGTATTCCAGAAG |
| 169 | NM_012242.3 | SAMi-hDKK1#269 | GGATGGGTATTCCAGAAGA |
| 170 | NM_012242.3 | SAMi-hDKK1#170 | CAAAGGACAAGAAGGTTCT |
| 171 | NM_012242.3 | SAMi-hDKK1#171 | TCTGTTTGTCTCCGGTCAT |
| 172 | NM_012242.3 | SAMi-hDKK1#172 | CTGTTTGTCTCCGGTCATC |
| 173 | NM_012242.3 | SAMi-hDKK1#173 | TGTTTGTCTCCGGTCATCA |
| 174 | NM_012242.3 | SAMi-hDKK1#174 | TCCGGTCATCAGACTGTGC |
| 175 | NM_012242.3 | SAMi-hDKK1#175 | GATTGTGTTGTGCTAGACA |
| 176 | NM_012242.3 | SAMi-hDKK1#176 | ATTGTGTTGTGCTAGACAC |
| 177 | NM_012242.3 | SAMi-hDKK1#177 | TTGTGTTGTGCTAGACACT |
| 178 | NM_012242.3 | SAMi-hDKK1#178 | TGTGTTGTGCTAGACACTT |
| 173 | NM_012242.3 | SAMi-hDKK1#179 | GTGTTGTGCTAGACACTTC |
| 180 | NM_012242.3 | SAMi-hDKK1#180 | TGTTGTGCTAGACACTTCT |
| 181 | NM_012242.3 | SAMi-hDKK1#181 | GTTGTGCTAGACACTTCTG |
| 182 | NM_012242.3 | SAMi-hDKK1#182 | TTGTGCTAGACACTTCTGG |
| 183 | NM_012242.3 | SAMi-hDKK1#183 | AGACACTTCTGGTCCAAGA |
| 184 | NM_012242.3 | SAMi-hDKK1#184 | GACACTTCTGGTCCAAGAT |
| 185 | NM_012242.3 | SAMi-hDKK1#185 | GGTCCAAGATCTGTAAACC |
| 186 | NM_012242.3 | SAMi-hDKK1#186 | GTCCAAGATCTGTAAACCT |
| 187 | NM_012242.3 | SAMi-hDKK1#187 | TCCAAGATCTGTAAACCTG |
| 188 | NM_012242.3 | SAMi-hDKK1#188 | GCATAGGAGAAAAGGCTCT |
| 189 | NM_012242.3 | SAMi-hDKK1#189 | AGCGTTGTTACTGTGGAGA |
| 190 | NM_012242.3 | SAMi-hDKK1#190 | GGAGAAGGTCTGTCTTGCC |
| 191 | NM_012242.3 | SAMi-hDKK1#191 | GAGAAGGTCTGTCTTGCCG |

TABLE 2-continued

305 DKK1-specific siRNA candidate sequences selected using 1-base sliding window screening

| SEQ ID NO: | Accession No. | Code Name | Sense Strand Sequence |
|---|---|---|---|
| 192 | NM_G12242.3 | SAMi-hDKK1#192 | AGAAGGTCTGTCTTGCCGG |
| 193 | NM_012242.3 | SAMi-hDKK1#193 | GAAGGTCTGTCTTGCCGGA |
| 194 | NM_012242.3 | SAMi-hDKK1#194 | AAGGTCTGTCTTGCCGGAT |
| 195 | NM_012242.3 | SAMi-hDKK1#195 | TCTGTCTTGCCGGATACAG |
| 196 | NM_012242.3 | SAMi-hDKK1#196 | CTGTCTTGCCGGATACAGA |
| 197 | NM_012242.3 | SAMi-hDKK1#197 | TGTCTTGCCGGATAGAGAA |
| 198 | NM_012242.3 | SAMi-hDKK1#198 | GTCTTGCCGGATACAGAAA |
| 199 | NM_012242.3 | SAMi-hDKK1#199 | TCTTGCCGGATACAGAAAG |
| 200 | NM_012242.3 | SAMi-hDKK1#200 | CTTGCCGGATACAGAAAGA |
| 201 | NM_012242.3 | SAMi-hDKK1#201 | TTGCCGGATACAGAAAGAT |
| 202 | NM_012242.3 | SAMi-hDKK1#202 | TGCCGGATACAGAAAGATC |
| 203 | NM_012242.3 | SAMi-hDKK1#2G3 | GCGGGATACAGAAAGATCA |
| 204 | NM_012242.3 | SAMi-hDKK1#204 | CAGAAAGATCACCATCAG |
| 205 | NM_012242.3 | SAMi-hDKK1#205 | CCAGTAATTCTTCTAGGCT |
| 206 | NM_012242.3 | SAMi-hDKK1#206 | CAGTAATTCTTCTAGGCTT |
| 207 | NM_012242.3 | SAMi-hDKK1#207 | ATTCTTCTAGGCTTCACAC |
| 208 | NM_012242.3 | SAMi-hDKK1#208 | AGACACTAAACCAGCTATC |
| 209 | NM_012242.3 | SAMi-hDKK1#209 | GCAGTGAACTCCTTTTATA |
| 210 | NM_012242.3 | SAMi-hDKK1#210 | CAGTGAACTCCTTTTATAT |
| 211 | NM_012242.3 | SAMi-hDKK1#211 | CCTTCATCAACTCAATCCT |
| 212 | NM_012242.3 | SAMi-hDKK1#212 | CTTCATCAACTCAATCCTA |
| 213 | NM_012242.3 | SAMi-hDKK1#213 | ATCAACTCAATCCTAAGGA |
| 214 | NM_012242.3 | SAMi-hDKK1#214 | TCAACTCAATCCTAAGGAT |
| 215 | NM_012242.3 | SAMi-hDKK1#215 | CAACTCAATCCTAAGGATA |

TABLE 2-continued

305 DKK1-specific siRNA candidate sequences selected using 1-base sliding window screening

| SEQ ID NO: | Accession No. | Code Name | Sense Strand Sequence |
|---|---|---|---|
| 216 | NM_012242.3 | SAMi-hDKK1#216 | AACTCAATCCTAAGGATAT |
| 217 | NM_012242.3 | SAMi-hDKK1#217 | AGTCAATCCTAAGGATATA |
| 218 | NM_012242.3 | SAMi-hDKK1#218 | CTCAATCCTAAGGATATAC |
| 219 | NM_012242.3 | SAMi-hDKK1#219 | GATATACAAGTTCTGTGGT |
| 220 | NM_012242.3 | SAMi-hDKK1#220 | GCATTCCAATAACACCTTC |
| 221 | NM_012242.3 | SAMi-hDKK1#221 | CATTCCAATAACACCTTCC |
| 222 | NM_012242.3 | SAMi-hDKK1#222 | GGAGTGTAAGAGCTTTGTT |
| 223 | NM_012242.3 | SAMi-hDKK1#223 | GAGTGTAAGAGCTTTGTTT |
| 224 | NM_012242.3 | SAMi-hDKK1#224 | TTTATGGAACTCCCCTGTG |
| 225 | NM_012242.3 | SAMi-hDKK1#225 | TTATGGAACTCCCCTGTGA |
| 226 | NM_012242.3 | SAMi-hDKK1#226 | GTGATTGCAGTAAATTACT |
| 227 | NM_012242.3 | SAMi-hDKK1#227 | TGATTGCAGTAAATTACTG |
| 228 | NM_012242.3 | SAMi-hDKK1#228 | GATTGCAGTAAATTACTGT |
| 229 | NM_012242.3 | SAMi-hDKK1#229 | ATTGCAGTAAATTACTGTA |
| 230 | NM_012242.3 | SAMi-hDKK1#230 | GTAAATTCTCAGTGTGGCA |
| 231 | NM_012242.3 | SAMi-hDKK1#231 | TAAATTCTCAGTGTGGCAC |
| 232 | NM_012242.3 | SAMi-hDKK1#232 | AAATTCTCAGTGTGGCACT |
| 233 | NM_012242.3 | SAMi-hDKK1#233 | TGGCACTTACCTGTAAATG |
| 234 | NM_012242.3 | SAMi-hDKK1#234 | GGCACTTACCTGTAAATGC |
| 235 | NM_012242.3 | SAMi-hDKK1#235 | GCACTTACCTGTAAATGCA |
| 236 | NM_012242.3 | SAMi-hDKK1#236 | CACTTACCTGTAAATGCAA |
| 237 | NM_012242.3 | SAMi-hDKK1#237 | GGTGCTGCACTGCCTATTT |
| 238 | NM_012242.3 | SAMi-hDKK1#238 | GTGCTGCACTGCCTATTTT |
| 239 | NM_012242.3 | SAMi-hDKK1#239 | TGTACACATTGATTGTTAT |

TABLE 2-continued

305 DKK1-specific siRNA candidate sequences selected using 1-base sliding window screening

| SEQ ID NO: | Accession No. | Code Name | Sense Strand Sequence |
|---|---|---|---|
| 240 | NM_012242.3 | SAMi-hDKK1#240 | GTACACATTGATTGTTATC |
| 241 | NM_012242.3 | SAMi-hDKK1#241 | TACACATTGATTGTTATCT |
| 242 | NM_012242.3 | SAMi-hDKK1#242 | CATTGATTGTTATCTTGAC |
| 243 | NM_012242.3 | SAMi-hDKK1#243 | ATTGTTATCTTGACTGACA |
| 244 | NM_012242.3 | SAMi-hDKK1#244 | TATCTTGACTGACAAATAT |
| 245 | NM_012242.3 | SAMi-hDKK1#245 | CATTTCAGCTTATAGTTCT |
| 246 | NM_012242.3 | SAMi-hDKK1#246 | AAGCATAACCCTTTACCCC |
| 247 | NM_012242.3 | SAMi-hDKK1#247 | AGCATAACCCTTTACCCCA |
| 248 | NM_012242.3 | SAMi-hDKK1#248 | GCATAACCCTTTACCCCAT |
| 249 | NM_012242.3 | SAMi-hDKK1#249 | CATAACCCTTTACCCCATT |
| 250 | NM_012242.3 | SAMi-hDKK1#250 | ACCCTTTACCCCATTTAAT |
| 251 | NM_012242.3 | SAMi-hDKK1#251 | CCATTTAATTCTAGAGTCT |
| 252 | NM_012242.3 | SAMi-hDKK1#252 | CATTTAATTCTAGAGTCTA |
| 253 | NM_012242.3 | SAMi-hDKK1#253 | ATTTAATTCTAGAGTCTAG |
| 254 | NM_012242.3 | SAMi-hDKK1#254 | TTCTAGAGTCTAGAACGCA |
| 255 | NM_012242.3 | SAMi-hDKK1#255 | TCTAGAGTCTAGAACGCAA |
| 256 | NM_012242.3 | SAMi-hDKK1#256 | CTAGAGTCTAGAACGCAAG |
| 257 | NM_012242.3 | SAMi-hDKK1#257 | TAGAGTCTAGAACGCAAGG |
| 258 | NM_012242.3 | SAMi-hDKK1#258 | AGAGTCTAGAACGCAAGGA |
| 259 | NM_012242.3 | SAMi-hDKK1#259 | GAGTCTAGAACGCAAGGAT |
| 260 | NM_012242.3 | SAMi-hDKK1#260 | CAAGGATCTCTTGGAATGA |
| 261 | NM_012242.3 | SAMi-hDKK1#261 | TGGAATGACAAATGATAGG |
| 262 | NM_012242.3 | SAMi-hDKK1#262 | TAGGTACCTAAAATGTAAC |
| 263 | NM_012242.3 | SAMi-hDKK1#263 | AGGTACCTAAAATGTAACA |

TABLE 2-continued

305 DKK1-specific siRNA candidate sequences selected using 1-base sliding window screening

| SEQ ID NO: | Accession No. | Code Name | Sense Strand Sequence |
|---|---|---|---|
| 264 | NM_012242.3 | SAMi-hDKK1#264 | GGTACCTAAAATGTAACAT |
| 265 | NM_012242.3 | SAMi-hDKK1#265 | AATACTAGCTTATTTTCTG |
| 266 | NM_012242.3 | SAMi-hDKK1#266 | ATACTAGCTTATTTTCTGA |
| 267 | NM_012242.3 | SAMi-hDKK1#267 | CTGAAATGTACTATCTTAA |
| 268 | NM_012242.3 | SAMi-hDKK1#268 | AATGTACTATCTTAATGCT |
| 269 | NM_012242.3 | SAMi-hDKK1#269 | ATGTACTATCTTAATGCTT |
| 270 | NM_012242.3 | SAMi-hDKK1#270 | TGTACTATCTTAATGCTTA |
| 271 | NM_012242.3 | SAMi-hDKK1#271 | TTAGGCTGTGATAGTTTTT |
| 272 | NM_012242.3 | SAMi-hDKK1#272 | TAGGCTGTGATAGTTTTTG |
| 273 | NM_012242.3 | SAMi-hDKK1#273 | AAATGTTATAAGTAGACAT |
| 274 | NM_012242.3 | SAMi-hDKK1#274 | AATGTTATAAGTAGACATA |
| 275 | NM_012242.3 | SAMi-hDKK1#275 | ATGTTATAAGTAGACATAC |
| 276 | NM_012242.3 | SAMi-hDKK1#276 | TGTGATCTTAGAGGTTTGT |
| 277 | NM_012242.3 | SAMi-hDKK1#277 | GTGATCTTAGAGGTTTGTG |
| 278 | NM_012242.3 | SAMi-hDKK1#278 | TGATCTTAGAGGTTTGTGT |
| 279 | NM_012242.3 | SAMi-hDKK1#279 | GATCTTAGAGGTTTGTGTG |
| 280 | NM_012242.3 | SAMi-hDKK1#280 | GTGTGTTCTACAAGAACGG |
| 281 | NM_012242.3 | SAMi-hDKK1#281 | TGTGTTCTACAAGAACGGA |
| 282 | NM_012242.3 | SAMi-hDKK1#282 | TTCTACAAGAACGGAAGTG |
| 283 | NM_012242.3 | SAMi-hDKK1#283 | TCTACAAGAACGGAAGTGT |
| 284 | NM_012242.3 | SAMi-hDKK1#284 | AACGGAAGTGTGATATGTT |
| 285 | NM_012242.3 | SAMi-hDKK1#285 | ACGGAAGTGTGATATGTTT |
| 286 | NM_012242.3 | SAMi-hDKK1#236 | CAGTGTCTAAATATAAGAC |
| 287 | NM_012242.3 | SAMi-hDKK1#287 | ATAAGACAATATTGATCAG |
| 288 | NM_012242.3 | SAMi-hDKK1#288 | TAAGACAATATTGATCAGC |
| 289 | NM_012242.3 | SAMi-hDKK1#289 | AAGACAATATTGATCAGCT |
| 290 | NM_012242.3 | SAMi-hDKK1#290 | ATTGATCAGCTCTAGAATA |
| 291 | NM_012242.3 | SAMi-hDKK1#291 | TTGATCAGCTCTAGAATAA |
| 292 | NM_012242.3 | SAMi-hDKK1#292 | TGATCAGCTCTAGAATAAC |
| 293 | NM_012242.3 | SAMi-hDKK1#293 | AGCTCTAGAATAACTTTAA |
| 294 | NM_012242.3 | SAMi-hDKK1#294 | TCTGCATTGATAAACTCAA |
| 295 | NM_12242.3 | SAMi-hDKK1#295 | CTGCATTGATAAACTCAAA |
| 296 | NM_012242.3 | SAMi-hDKK1#296 | TGCATTGATAAACTCAAAT |
| 297 | NM_012242.3 | SAMi-hDKK1#297 | AAACTCAAATGATCATGGC |
| 293 | NM_012242.3 | SAMi-hDKK1#298 | AACTCAAATGATCATGGCA |
| 299 | NM_012242.3 | SAMi-hDKK1#299 | ATGAGAGTGAATCTTACAT |
| 300 | NM_012242v3 | SAMi-hDKK1#300 | TGAGAGTGAATCTTACATT |
| 301 | NM_012242.3 | SAMi-hDKK1#301 | GAGAGTGAATCTTACATTA |
| 302 | NM_012242.3 | SAMi-hDKK1#302 | AGAGTGAATCTTACATTAC |
| 303 | NM_012242.3 | SAMi-hDKK1#303 | GAGTGAATCTTACATTACT |
| 304 | NM_012242.3 | SAMi-hDKK1#304 | TCTTACATTACTACTTTCA |
| 305 | NM_012242.3 | SAMi-hDKK1#305 | CTTACATTACTACTTTCAA |

TABLE 3

DKK1-specific siRNA sequences mentioned in related literature KR 10-1167675, KR 10-2010-0051195)

| SEQ ID NO. | Related Patent | Code Name | Sense strand sequence |
|---|---|---|---|
| 306 | KR 10-1167675 | SAMi-DKK1 patent#1 | CACTAAACCA GCTATCCAA |
| 307 | KR 10-1167675 | SAMi-DKK1 patent#2 | GGTAATGATC ATAGCACCT |

TABLE 3-continued

| DKK1-specific siRNA sequences mentioned in related literature KR 10-1167675, KR 10-2010-0051195) | | | |
|---|---|---|---|
| SEQ ID NO. | Related Patent | Code Name | Sense strand sequence |
| 308 | KR 10-1167675 | SAMi-DKK1 patent#3 | GAATAAGTAC CAGACCATT |
| 309 | KR 10-2010-0051195 | SAMi-DKK1 patent#4 | AGGTCTGTCT TGCCGGATA |

Example 2: Screening of siRNA Targeting Human DKK1 Gene

Screening was performed to find sequences that effectively inhibit DKK1 mRNA expression using 312 siRNAs targeting the human DKK1 sequence synthesized in Example 1.

2-1: Transfection of Cells with hDKK1 siRNA

In order to find siRNA sequences that efficiently inhibit human DKK1 expression, A549, which is a human lung cancer cell line, and HFDPC, which is a human follicular dermal papilla cell, were used. The A549 cell line was cultured at 37° C. in the presence of 5% $CO_2$ using RPMI medium (HyClone, US) containing 10% fetal bovine serum (HyClone, US) and 1% penicillin-streptomycin (HyClone, US), and the HFDPC was cultured at 37° C. in the presence of 5% $CO_2$ using follicle dermal papilla cell growth medium (Promo cell, Germany) containing SupplementMix (Promo cell, Germany). The A549 and HFDPC cells were seeded at $4\times10^4$ cells/well on a 12-well plate (Falcon, US), and the next day, the cells were transfected with 20 nM siRNA using Lipofectamine RNAiMAX (Invitrogen, US) according to the manufacturer's protocol.

2-2: Primary and Secondary Screening of 312 siRNAs Through hDKK1 Expression Inhibition Efficacy Analysis The A549 cells were repeatedly transfected 3 times with 312 types of siRNA in the same manner as in Example 2-1. Total RNA was extracted from the cell lysate using a universal RNA extraction kit (Bioneer), and the mRNA expression levels of hDKK1 and hRPL13A (internal control) were measured using the RNA as a template according to the manufacturer's protocol using an AccuPower® GreenStar™ Master Mix (Bioneer) and the relative mRNA expression rate of hDKK1 gene compared to the control sample was analyzed. The primer sequences for each gene are given as follows (Table 4).

TABLE 4

| hDKK1 and RPL13A (internal control) primer sequences | | |
|---|---|---|
| SEQ ID NO: 310 | DKK1-forward | 5'-TGACAACTACCAGCCGTACC-3' |
| SEQ ID NO: 311 | DKK1-reverse | 5'-CAGGCGAGACAGATTTGCAC-3' |
| SEQ ID NO: 312 | RPL13A-forward | 5'-GTGTTTGACGGCATCCCACC-3' |
| SEQ ID NO: 313 | RPL13A-reverse | 5'-TAGGCTTCAGACGCACGACC-3' |

Figure 2B:
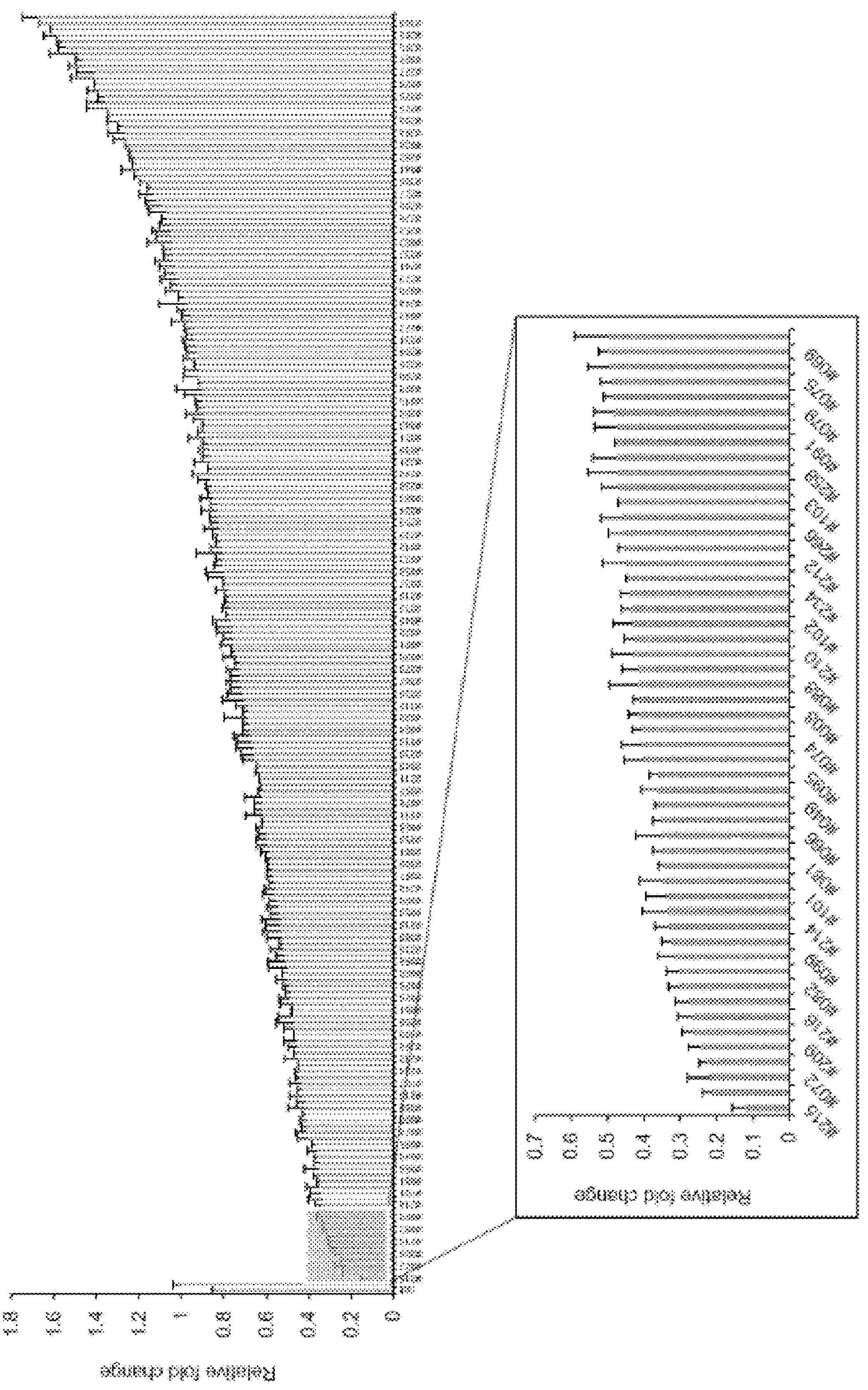

FIGS. 2A and 2B show the results of primary and secondary screening for 312 double-stranded oligo RNAs targeting DKK1. As a result, 46 sequences showing DKK1 mRNA inhibitory activity of 50% or more were identified. 52 sequences showing DKK1 mRNA inhibitory activity of 50% or more were identified through secondary screening to ensure reproducibility in the same manner as above. 18 consensus sequences showing DKK1 mRNA inhibitory activity of 55% or more were selected through repeated primary and secondary screening.

2-3: Evaluation of Reproducibility of Selected hDKK1 siRNA Candidate Sequences

Figure 3:
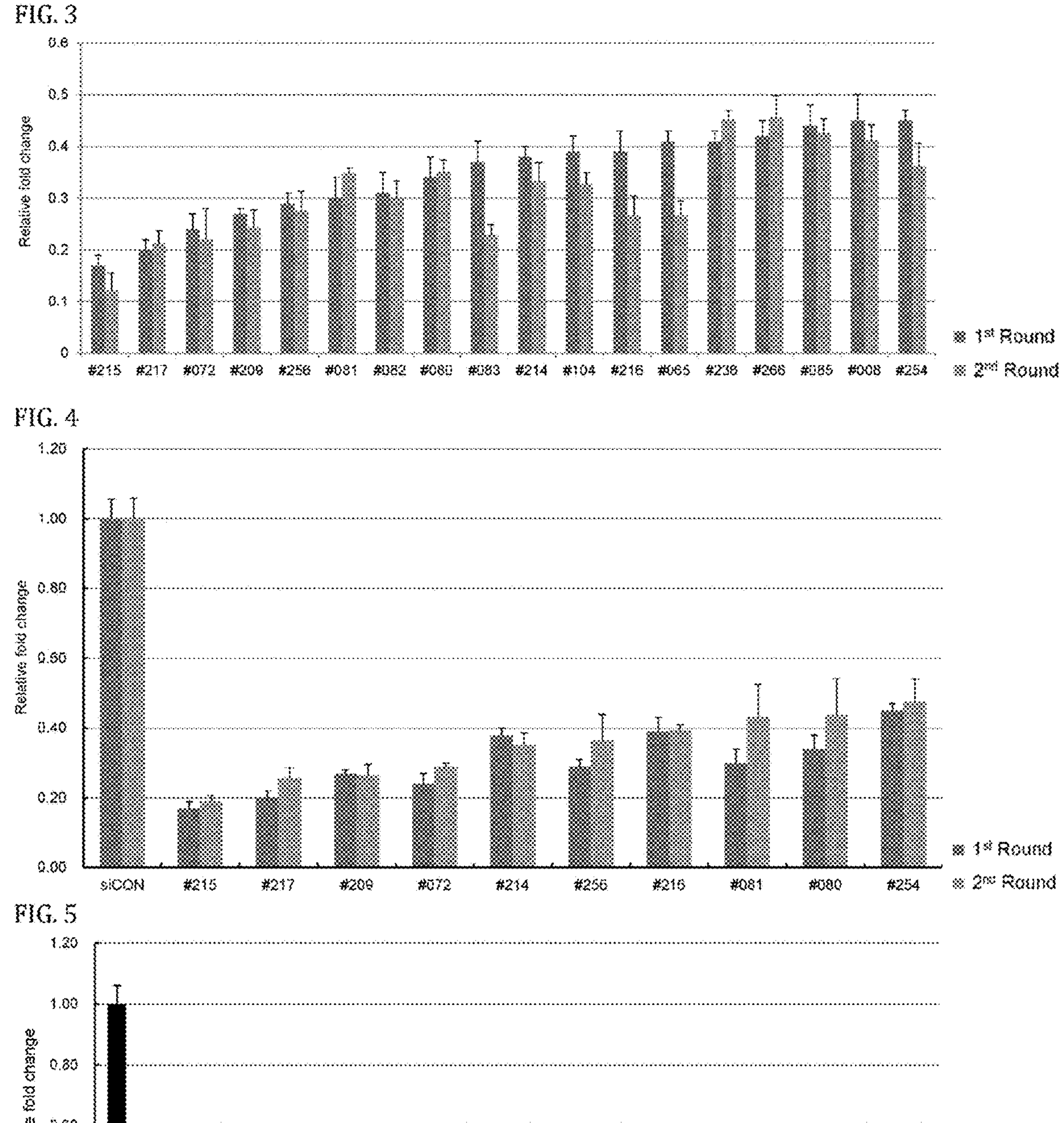
FIG. 3 shows the results of primary and secondary screening for 18 sequences having the highest DKK1 expression inhibitory effect.

In order to evaluate the reproducibility of 10 sequences having excellent inhibitory activity among the 18 hDKK1 siRNA sequences selected in Example 2-2, A549 cells were transfected repeatedly 3 times with 10 different siRNA sequences. The result showed that, similar to the primary and secondary screening, all 10 sequences showed inhibitory activity of 55% or more, and in particular, the #72 sequence showed high inhibitory activity of 70% or more (FIGS. 3 and 4).

Figure 5:
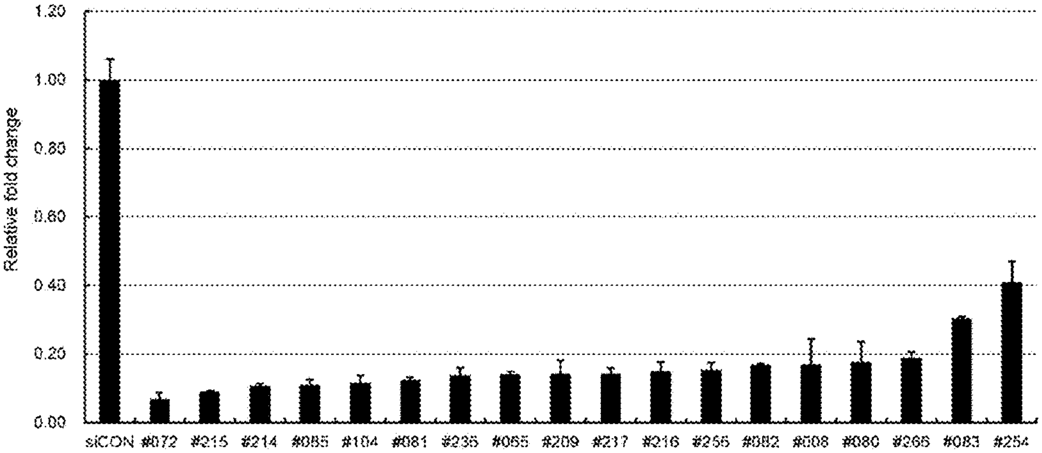
FIG. 5 shows the result of a reproducibility test on 10 finally selected sequences in HFDPC cells, which are human dermal papilla cells.

For secondary reproducibility evaluation, human follicular dermal papilla cells (HFDPC) were repeatedly transfected three times with 10 sequences in the same manner as above, and analysis was performed thereon. The result showed that all 10 sequences showed high DKK1 mRNA inhibitory activity, and like A549 cells, the #72 sequence exhibited high inhibitory activity of 80% or more (FIG. 5).

One sequence that most effectively inhibits expression of human DKK1 genes was finally selected through the repetition and reproducibility evaluation, and the information of the DKK1 siRNA sequence is shown in Table 5 below.

TABLE 5

| siRNA sequences that effectively inhibit hDKK1 gene expression | | | |
|---|---|---|---|
| SEQ ID NO: | Code Name | Position | Sense strand sequence |
| 72 | SAMi-DKK1 #72 | 369-387 | ATAAGTACC AGACCATTGA |

Example 3: Synthesis of Double-Stranded Oligonucleotide Construct Using Selected DKK1 Sequence #72 and Evaluation of DKK1 Expression Inhibition Activity Thereof 3-1: Synthesis of SAMiRNA-DKK1 #72 Construct The double-stranded oligonucleotide construct (SAMiRNA) prepared in the present invention has the structure represented by the following Structural Formula.

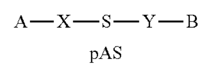

An oligonucleotide single strand having the desired sequence was obtained through a synthesis process accomplished by repeatedly performing a cycle including deblocking, coupling, capping and oxidation using a nucleoside-bound solid support (CPG). The series of processes for synthesizing the double-stranded oligonucleotide was performed using an RNA synthesizer (384 synthesizer, BIONEER, Korea).

The sense strand of the double-stranded oligonucleotide construct was produced by repeatedly linking the phosphodiester bonds constituting the DNA backbone structure using β-cyanoethyl phosphoramidite with polyethylene glycol (PEG)-CPG as a support to synthesize a double-helix oligonucleotide-hydrophilic substance construct including a sense strand in which polyethylene glycol was bound to the 3' end and $C_{24}$ including a disulfide bond was bound to the 5' end. The antisense strand to be annealed with the sense strand was produced by repeatedly linking the phosphodiester bonds constituting the RNA backbone structure using β-cyanoethyl phosphoramidite to produce an antisense strand having a sequence complementary to the sense strand, and then producing an antisense strand having a phosphate group bound to the 5' end using a chemical phosphorylation reagent (CPR).

After synthesis was completed, the oligonucleotide single strand and oligonucleotide-polymer construct synthesized by treatment with 28% (v/v) ammonia in a water bath at 60° C. are separated from the CPG, and then the protective residues were removed by deprotection. Oligo single-stranded RNA and the oligo RNA-polymer construct from which protective residues had been removed were treated in an oven at 70° C. with N-methylpyrrolidone, triethylamine and triethylamine trihydrofluoride at a volume ratio of 10:3:4 to remove the 2' end. The oligonucleotide single strand, the oligonucleotide-polymer construct and the ligand-bound oligonucleotide-polymer construct were separated from the reaction products through high performance liquid chromatography (HPLC), the molecular weight thereof was measured through MALDI-TOF mass spectrometry (MALDI TOF-MS, SHIMADZU, Japan), and whether or not they corresponded to the nucleotide sequence and the oligonucleotide-polymer constructs to be synthesized was determined. Then, to prepare each double-stranded oligonucleotide construct, equal amounts of the sense strand and the antisense strand were mixed, the resulting mixture was reacted at 90° C. in a constant-temperature water bath for 3 minutes in 1×annealing buffer (30 mM HEPES, 100 mM potassium acetate, 2 mM magnesium acetate, at pH of 7.0), and then reacted at 37° C. to produce the desired SAMiRNA, monoSAMiRNA (n=1), monoSAMiRNA (n=2), monoSAMiRNA (n=3), and monoSAMiRNA (n=4). The annealing of the prepared double-stranded oligonucleotide constructs was identified through electrophoresis.

3-2: Analysis of SAMiRNA-DKK1 #72 Nanoparticle Particle Size

The size and polydispersity index of SAMiRNA were measured using a Zetasizer Nano ZS (Malvern, UK) for analysis of the particle size of SAMiRNA-DKK1 #72 synthesized in Example 3-1. The size and polydispersity index of SAMiRNA-DKK1 #72 nanoparticles are shown in Table 6 below, and a representative graph is shown in FIG. 6.

TABLE 6

Size and polydispersity index of SA1VIiRNA-DKK1 #72 nanoparticles

| SEQ ID NO: | Code Name | Size | PDI |
|---|---|---|---|
| 72 | SAMi-DKK1 #72 | 11.43 | 0.403 |

3-3: Transfection of Cells with SAMiRNA-DKK1 #72 Nanoparticles

Human follicle dermal papilla cells (HFDPC) were used to evaluate the DKK1 expression inhibitory activity of the final candidate SAMiRNA-DKK1 #72. The HFDPC line was cultured at 37° C. in the presence of 5% $CO_2$ using follicle dermal papilla cell growth medium (Promo cell, Germany) containing SupplementMix (Promo cell, Germany). HFDPCs were seeded at $4\times10^4$ cells/well on a 12-well plate (Falcon, US), and the next day SAMiRNA-DKK1 #72 was diluted with 1×DPBS and the cells were treated with 5 piM SAMiRNA-DKK1 #72. The cells were treated two or four times in total with SAMiRNA-DKK1 #72 once every 12 hours and cultured at 37° C. in the presence of 5% $CO_2$.

3-4: Evaluation of DKK1 mRNA Expression Inhibitory Activity of SAMiRNA-DKK1 #72 Nanoparticles qRT-PCR analysis was performed to evaluate the DKK1 gene expression inhibitory activity of the final candidate SAMiRNA-DKK1 #72. The HFDPC line was seeded at $4\times10^4$ cells/well on a 12-well plate (Falcon, US) and cultured at 37° C. in the presence of 5% $CO_2$. The next day, the cells were treated two and four times with 5 piM SAMiRNA-DKK1 #72, and were transfected with 20 nM SAMiRNA-DKK1 #72 as a positive control group using lipofectamine RNAiMAX (Invitrogen, US). The cells were cultured for 48 hours, total RNA was extracted from the cell lysate using a Universal RNA extraction kit (Bioneer, KR), and the mRNA expression levels of DKK1 and RPL13A (internal control) were analyzed through qRT-PCR using the RNA as a template according to the manufacturer's protocol using an AccuPower® GreenStar™ Master Mix (Bioneer, KR).

The result showed that SAMiRNA-DKK1 #72 had DKK1 mRNA expression inhibitory activity of about 70% or more, which was higher than that of the positive control group (FIG. 7).

3-5: Evaluation of DKK1 Protein Expression Inhibition Activity of SAMiRNA-DKK1 #72 Nanoparticles The effect of the final candidate SAMiRNA-DKK1 #72 on inhibition of expression of the DKK1 protein in the HFDPC line was determined. The HFDPC line was seeded at $4\times10^4$ cells/well on a 12-well plate (Falcon, US), cultured at 37° C. in the presence of 5% $CO_2$, and, the next day, treated two or four times with 5 μM SAMiRNA. The cells were transfected with 20 nM SAMiRNA as a positive control group using Lipofectamine RNAiMAX (Invitrogen, US). The cells were cultured for 48 hours, the supernatant was collected and sampled, and the expression level of the DKK1 protein was quantitatively analyzed according to the manufacturer's protocol using a human Dkk-1 Quantikine ELISA Kit (R&D systems, US).

Figure 8:
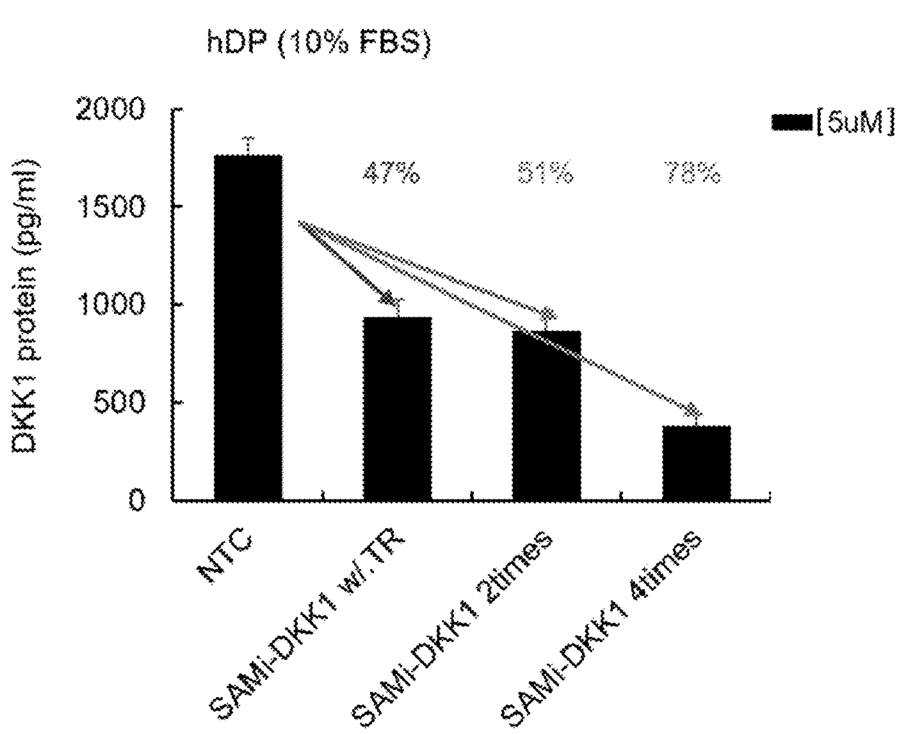
FIG. 8 shows the protein expression level of DKK1 when the HFDPC cell line is treated with SAMiRNA-DKK1 #72.

The result of ELISA analysis showed that the final candidate substance, SAMiRNA-DKK1 #72, exhibited a protein inhibitory activity of about 70% or more, which was similar to the DKK1 mRNA expression inhibitory activity of Examples 3 to 4, and that the protein inhibitory activity of SAMiRNA-DKK1 #72 was comparable to that of the positive control group (FIG. 8).

Example 4: Determination of Delivery of SAMiRNA Nanoparticles into Hair Root

In order to determine the efficiency of delivery of the finally selected SAMiRNA-DKK1 #72 into human hair roots, the delivery effect was tested using human hair. On the day of the experiment, hair was obtained by plucking the hair while holding the tip thereof, cut to a length of about 1 cm from the root, and then cultured in 200 μl of M199 medium (10% FBS+1% penicillin) on a 96-well plate for 1 hour. Then, the hair was cultured for 24 hours in 200 μl of M199 medium containing 10 μM SAMiRNA labeled with FAM fluorescence. After treatment with SAMiRNA for 24 hours, the hair was washed three times with DPBS and the hair root was fixed in PBS containing 3.7% formaldehyde and 2% FBS for 20 minutes. The fixed hair root was planted in a base mold containing an OCT compound and placed on a pre-frozen stainless plate to completely freeze the OCT compound. The frozen tissue was stored at −70° C. and placed at −20° C. for about 30 minutes to facilitate tissue sectioning before cutting with a tissue sectioner. The tissue section with a thickness of 10 μm was placed on a slide and dried for 1 hour. After drying, the tissue section was mounted using a mounting solution containing DAPI.

Figure 9:
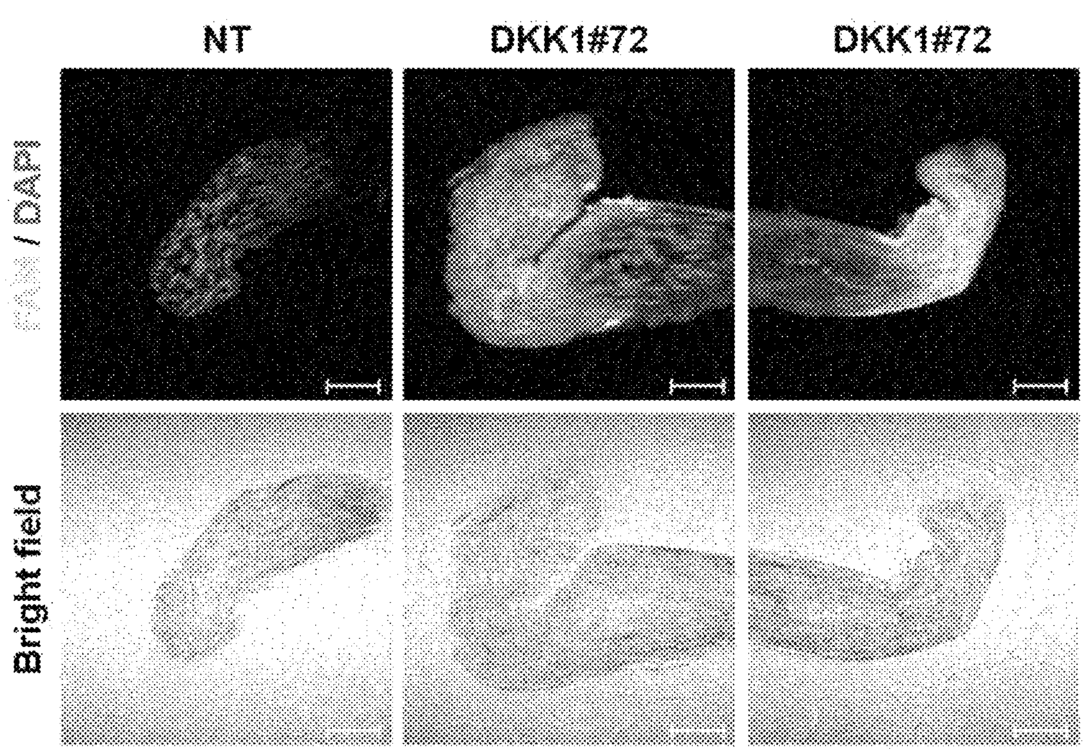
FIG. 9 is a result showing efficient delivery of SAMiRNA-DKK1 #72 to human hair root cells.

Fluorescence was observed with a confocal laser scan microscope (LSM5 LIVE CONFIGURATION VARIOTWO VRGB). The result showed that SAMiRNA was well delivered to cells in the root of the hair tissue (FIG. 9).

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

INDUSTRIAL APPLICABILITY

The DKK1-specific double-stranded oligonucleotide, the double-stranded oligonucleotide construct including the double-stranded oligonucleotide, the nanoparticle including the double-stranded oligonucleotide or the double-stranded oligonucleotide construct, or the composition for preventing hair loss or hair growth containing the double-stranded oligonucleotide, the double-stranded oligonucleotide construct or the nanoparticle as an active ingredient can inhibit the expression of DKK1 with high efficiency without causing side effects, and exhibits excellent effects of preventing hair loss and promoting hair growth, thus being very useful for preventing hair loss and promoting hair growth.

Sequence Free Text

An electronic file is attached.

The invention claimed is:

1. A DKK1-specific double-stranded oligonucleotide comprising:

a sense strand consisting of a sequence selected from the group consisting of SEQ ID NOS: 72, 80, 81, 209, 214, 215, 216, 217, 254 and 256; and an anti-sense strand having a sequence complementary thereto, wherein the DKK1-specific double-stranded oligonucleotide is DNA/RNA, the sense strand is DNA and the anti-sense strand is RNA, and the sense strand and the anti-sense strand each consists of 19 nucleotides.

2. The DKK1-specific double-stranded oligonucleotide according to claim 1, wherein the sense strand or the antisense strand of the double-stranded oligonucleotide comprises a chemical modification.

3. The DKK1-specific double-stranded oligonucleotide according to claim 2, wherein the chemical modification comprises one or more selected from the group consisting of: modification through substitution with any one selected from the group consisting of methyl (—$CH_3$), methoxy (—$OCH_3$), amine (—$NH_2$), fluorine (—F), —O-2-methoxyethyl, —O-propyl, —O-2-methylthioethyl, —O-3-aminopropyl, —O-3-dimethylaminopropyl, —O-N-methylacetamido and —O-dimethylamidooxyethyl, of a hydroxyl group (—OH) at a 2' carbon position of a sugar structure in at least one nucleotide; modification through substitution, with sulfur, of oxygen in the sugar structure of the nucleotide; modification of a nucleotide bond into any bond selected from the group consisting of a phosphorothioate, boranophosphate, and methyl phosphonate bond; and modification into PNA (peptide nucleic acid), locked nucleic acid (LNA) or unlocked nucleic acid (UNA).

4. The DKK1-specific double-stranded oligonucleotide according to claim 1, wherein the double-stranded oligonucleotide has a structure in which one or more phosphate groups are bound to a 5' terminal nucleotide end of the antisense strand of the double-stranded oligonucleotide.

5. A DKK1-specific double-stranded oligonucleotide construct having a structure represented by the following Structural Formula (1):

Structural Formula (1)

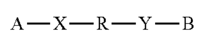

wherein A is a hydrophilic substance, B is a hydrophobic substance, X and Y are each independently a simple covalent bond or a linker-mediated covalent bond, and R is the DKK1-specific double-stranded oligonucleotide according to claim 1.

6. The DKK1-specific double-stranded oligonucleotide construct according to claim 5, wherein the double-stranded oligonucleotide construct has a structure represented by the following Structural Formula (2):

Structural Formula (2)

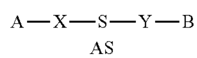

wherein S and AS are a sense strand and an antisense strand, respectively, of the DKK1-specific double-stranded oligonucleotide according to claim 5, and A, B, X and Y are as defined in claim 5.

7. The DKK1-specific double-stranded oligonucleotide construct according to claim 6, wherein the DKK1-specific double-stranded oligonucleotide construct has a structure represented by the following Structural Formula (3) or (4):

Structural Formula (3)

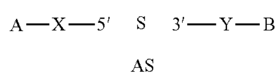

Structural Formula (4)

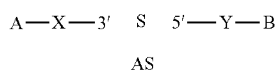

wherein A, B, X, Y, S and AS are as defined in claim 6, and 5' and 3' represent 5' and 3' ends, respectively, of the double-stranded oligonucleotide sense strand.

8. The DKK1-specific double-stranded oligonucleotide construct according to claim 5, wherein the hydrophilic substance is selected from the group consisting of polyethylene glycol (PEG), polyvinylpyrrolidone, and polyoxazoline.

9. The DKK1-specific double-stranded oligonucleotide construct according to claim 5, wherein the hydrophilic substance has a structure represented by the following Structural Formula (5) or Structural Formula (6):

Structural Formula (5)

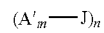

Structural Formula (6)

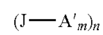

wherein A' is a hydrophilic substance monomer, J is a linker connecting m hydrophilic substance monomers to each other or connecting m hydrophilic substance monomers to the double-stranded oligonucleotide, m is an integer from 1 to 15, and n is an integer from 1 to 10, wherein the hydrophilic substance monomer A' comprises any one compound selected from the following compounds (1) to (3) and the linker J is selected from the group consisting of $—PO_3—$, $—SO_3—$ and $—CO_2—$:

Compound (1)

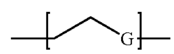

wherein G in Compound (1) is selected from the group consisting of O, S and NH;

Compound (2)

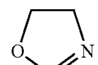

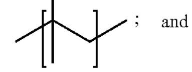

; and

Compound (3)

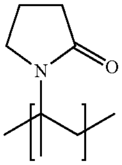

.

10. The DKK1-specific double-stranded oligonucleotide construct according to claim 5, wherein the hydrophobic substance is selected from the group consisting of a steroid derivative selected from the group consisting of cholesterol, cholestanol, cholic acid, cholesteryl formate, cholestanol formate and cholestanol amine, a glyceride derivative selected from the group consisting of mono-glyceride, di-glyceride and tri-glyceride, glycerol ether, polypropylene glycol, C12 to C50 unsaturated or saturated hydrocarbon, diacylphosphatidylcholine, fatty acid, phospholipid, lipopolyamine, lipid, tocopherol, and tocotrienol.

11. The DKK1-specific double-stranded oligonucleotide construct according to claim 5, wherein the covalent bond represented by X and Y is a non-degradable bond or a degradable bond, wherein the non-degradable bond comprises an amide bond or a phosphate bond, and wherein the degradable bond comprises any one selected from the group consisting of a disulfide bond, an acid-degradable bond, an ester bond, an anhydride bond, a biodegradable bond, and an enzyme-degradable bond.

12. The DKK1-specific double-stranded oligonucleotide construct according to claim 5, wherein a ligand having the property of specifically binding to a receptor that promotes internalization of target cells through receptor-mediated endocytosis (RME) is further bound to the hydrophilic substance.

13. The DKK1-specific double-stranded oligonucleotide construct according to claim 12, wherein the ligand is selected from the group consisting of target-receptor-specific antibodies, aptamers and peptides, folate, N-acetyl galactosamine (NAG), glucose and mannose.

14. The DKK1-specific double-stranded oligonucleotide construct according to claim 5, wherein an amine group or polyhistidine group is further introduced at the distal end of the hydrophilic substance, or wherein the amine group or polyhistidine group is bound to the hydrophilic substance through one or more linkers.

15. A nanoparticle comprising the DKK1-specific double-stranded oligonucleotide according to claim 1.

16. The nanoparticle according to claim 15, wherein the nanoparticle comprises a combination of double-stranded oligonucleotide constructs including double-stranded oligonucleotides having different sequences.

17. The nanoparticle according to claim 15, wherein the nanoparticles are lyophilized.

18. A composition for preventing hair loss or promoting hair growth comprising the double-stranded oligonucleotide construct according to claim 5, as an active ingredient.

19. A composition for preventing hair loss or promoting hair growth comprising the nanoparticle according to claim 15, as an active ingredient.

20. The DKK1-specific double-stranded oligonucleotide according to claim 1, wherein the sense strand consists of the sequence of SEQ ID NO: 72.

* * * * *